United States Patent
Kalkum et al.

(10) Patent No.: US 11,726,087 B2
(45) Date of Patent: *Aug. 15, 2023

(54) METHODS, COMPOSITIONS, AND KITS FOR DETECTION OF ASPERGILLOSIS

(71) Applicant: CITY OF HOPE, Duarte, CA (US)

(72) Inventors: Markus Kalkum, Azusa, CA (US); Karine Bagramyan, North Hollywood, CA (US); Diana Diaz-Arevalo, Monrovia, CA (US); James I. Ito, La Verne, CA (US); Sanjeet Dadwal, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 73 days.

This patent is subject to a terminal disclaimer.

(21) Appl. No.: 16/872,156

(22) Filed: May 11, 2020

(65) Prior Publication Data

US 2020/0271651 A1 Aug. 27, 2020

Related U.S. Application Data

(63) Continuation of application No. 15/236,988, filed on Aug. 15, 2016, now Pat. No. 10,648,982, which is a continuation of application No. 14/217,004, filed on Mar. 17, 2014, now Pat. No. 9,416,395.

(60) Provisional application No. 61/798,640, filed on Mar. 15, 2013.

(51) Int. Cl.

| | |
|---|---|
| *A61K 38/08* | (2019.01) |
| *A01N 37/18* | (2006.01) |
| *A61K 38/00* | (2006.01) |
| *A61P 31/10* | (2006.01) |
| *A61K 39/00* | (2006.01) |
| *A61K 39/395* | (2006.01) |
| *G01N 33/53* | (2006.01) |
| *G01N 33/573* | (2006.01) |
| *C12Q 1/37* | (2006.01) |
| *C07K 16/40* | (2006.01) |
| *G01N 33/569* | (2006.01) |
| *C07K 16/14* | (2006.01) |
| *A61K 38/16* | (2006.01) |
| *A61K 38/10* | (2006.01) |
| *A61K 38/06* | (2006.01) |
| *A61K 38/04* | (2006.01) |
| *A61K 38/07* | (2006.01) |
| *G01N 33/543* | (2006.01) |
| *G01N 33/577* | (2006.01) |

(52) U.S. Cl.
CPC .......... *G01N 33/573* (2013.01); *A61K 38/00* (2013.01); *A61K 38/04* (2013.01); *A61K 38/06* (2013.01); *A61K 38/07* (2013.01); *A61K 38/08* (2013.01); *A61K 38/10* (2013.01); *A61K 38/16* (2013.01); *A61K 39/0002* (2013.01); *C07K 16/14* (2013.01); *C07K 16/40* (2013.01); *C12Q 1/37* (2013.01); *G01N 33/54313* (2013.01); *G01N 33/56961* (2013.01); *G01N 33/577* (2013.01); *C07K 2317/622* (2013.01); *C07K 2317/92* (2013.01); *G01N 2333/38* (2013.01); *G01N 2333/962* (2013.01)

(58) Field of Classification Search
None
See application file for complete search history.

(56) References Cited

U.S. PATENT DOCUMENTS

| | | | | |
|---|---|---|---|---|
| 9,416,395 | B2 * | 8/2016 | Kalkum | A61K 38/04 |
| 10,648,982 | B2 * | 5/2020 | Kalkum | A61K 38/00 |
| 2011/0306035 | A1 | 12/2011 | Arad et al. | |

FOREIGN PATENT DOCUMENTS

| | | | | |
|---|---|---|---|---|
| WO | WO-0148209 A2 * | 7/2001 | | C07K 14/245 |

OTHER PUBLICATIONS

GenBank Database, Accession No. KAH1420777, 2 pages at residues 1548-1552 (2021) (Year: 2021).*
GenBank Database, Accession No. TPR11056, 2 pages at residues 1515-1519 (2019) (Year: 2019).*
Abad, A., et al., "What Makes Aspergillus Fumigatus a Successful Pathogen? Genes and Molecules Involved in Invasive Aspergillosis," Rev. Iberoam Micol. 27(4):155-182 (2010).
Amich, J., et al., "Aspergillus Fumigatus Survival in Alkaline and Extreme Zinc-Limiting Environments Relies on the Induction of a Zinc Homeostasis System Encoded by the zrfC and aspf2 Genes," Eukaryotic Cell 9(3):424-437 (2010).
Banerjee, B., et al., "Immunological Characterization of Asp f 2, a Major Allergen from Aspergillus Fumigatus Associated with Allergic Bronchopulmonary Aspergillosis," Infection and Immunity 66(11):5175-5182 (1998).

(Continued)

*Primary Examiner* — Thea D' Ambrosio
(74) *Attorney, Agent, or Firm* — Perkins Coie LLP; Lara J Dueppen; Allison M. Glasunow

(57) ABSTRACT

Provided herein are methods for detecting an *Aspergillus* protease in a sample, diagnosing a subject with aspergillosis caused by an *Aspergillus* infection based on the presence of an *Aspergillus* protease in a sample, and methods of aspergillosis treatment that incorporate these diagnostic methods. In certain embodiments, the *Aspergillus* protease is Asp f2, and the *Aspergillus* infection is caused *A. fumigatus, A. flavus, A. versicolor, A. niger,* or *A. terreus*. Also provided herein are antibodies and kits for use in these methods, including novel antibodies specific for Asp f2.

14 Claims, 39 Drawing Sheets

Specification includes a Sequence Listing.

(56) References Cited

OTHER PUBLICATIONS

De Pauw, B., et al., "Revised Definitions of Invasive Fungal Disease from the European Organization for Research and Treatment of Cancer/Invasive Fungal Infections Cooperative Group and the National Institute of Allergy and Infectious Diseases Mycoses Study Group (EORTC/MSG) Consensus Group," Clin. Infect. Dis. 46(12):1813-1821 (2008).
Kellar, K. L., et al., "Multiplexed Microsphere-Based Flow Cytometric Assays," Exp. Hematol. 30:1227-1237 (2002).
Knutsen, A. P., et al., "IgE Antibody to Aspergillus Fumigatus Recombinant Allergens in Cystic Fibrosis Patients with Allergic Bronchopulmonary Aspergillosis," Allergy 59:198-203 (2004).
Kurup, V. P., et al., "Selected Recombinant Aspergillus Fumigatus Allergens Bind Specifically to IgE in ABPA," Clinical and Experimental Allergy 30:988-993 (2000).
Kurup, V.P., "Aspergillus Antigens: Which are Important?" Medical Mycology Supplement I 43:S189-S196 (2005).
Singh, B., et al., "Immuno-Reactive Molecules Identified from the Secreted Proteome of Aspergillus Fumigatus," Journal of Proteome Research 9:5517-5529 (2010).
Singh, B., et al., "Human Pathogens Utilize Host Extracellular Matrix Proteins Laminin and Collagen for Adhesion and Invasion of the Host," FEMS Microbiol. Rev. 36:1122-1180 (2012).
Stevens, D. A., et al., "Allergic Bronchopulmonary Aspergillosis in Cystic Fibrosis—State of the Art: Cystic Fibrosis Foundation Consensus Conference," Clinical Infectious Diseases 37(Suppl 3):S225-S264 (2003).

* cited by examiner

Monoclonal antibody 5D7A1 VH domain amino acid sequence: (SEQ ID NO: 1)
LPEFEVQLEESGAELARPGASVKMSCKASGYTFTTYTMHWVKQRPGQGLEWIGYINPSS
GYTNYNQKFKDKATLTANKSSSIGYMQLSSLTSEDSALYYCLRRPYRSHGGWFFDVWG
AGTTVTVSSAKTTPPSVYRSSK

Monoclonal antibody 5D7A1 VL domain amino acid sequence: (SEQ ID NO: 2)
MESQTQVFVYMLLWLSGVDGDIVMTQSQKFMSTSVGDRVSVTCKASQNVETNVAWY
QQKLGQSPKALIYSASFRTSGVPDRFTGSGSGTDFTLTINNVQSEDLAEYFCQQYNTYPL
TFGAGTKLELKRADAAPTVSISHHPVLES

FIG. 3

Monoclonal antibody 5D7A1 VH domain DNA sequence: (SEQ ID NO: 3)
cttccggaattcgaggtccagctggaggagtcagggggctgaattggcaagacctggggcctcagtgaagatgtcctgcaaggcttctggct
acacctttacaacctacacgatgcactgggtaaaacagaggcctggacagggtctggaatggattggatacattaatcctagtagtggttata
ctaattacaatcaaaagttcaaagacaaggccacattgactgcaaacaaatcctccagtatcggctacatgcagctgagcagcctaacatctg
aggattctgcactttattattgtttaagaaggccttataggtcccacgggggctggttcttcgatgtctggggcgcagggaccacggtcaccgt
ctcctcagccaaaacgacacccccatctgtctatagatcttccaag

Monoclonal antibody 5D7A1 VL domain DNA sequence: (SEQ ID NO: 4)
atggagtcacagactcaggtctttgtatacatgttgctgtggttgtctggtgttgatggagacattgtgatgacccagtctcaaaaattcatgtcc
acatcagtaggagacagggtcagcgtcacctgcaaggccagtcagaatgtagagactaatgtagcctggtatcaacagaaactagggcaa
tctcctaaagcactgatttactcggcatccttccggaccagtggagtccctgatcgcttcacaggcagtggatctgggacagatttcactctca
ccatcaacaatgtgcagtctgaagacttggcagagtatttctgtcagcaatataacacctatccgctcacgttcggtgctgggaccaagctgg
agctgaaacgggctgatgctgcaccaactgtatccatctcccaccatccagttctagaaagc

FIG. 4

FluHSA2 peptide amino acid sequence (SEQ ID NO: 5):
5-Fam-TKCATESAVNRRPCFSALK-[DABCYL]

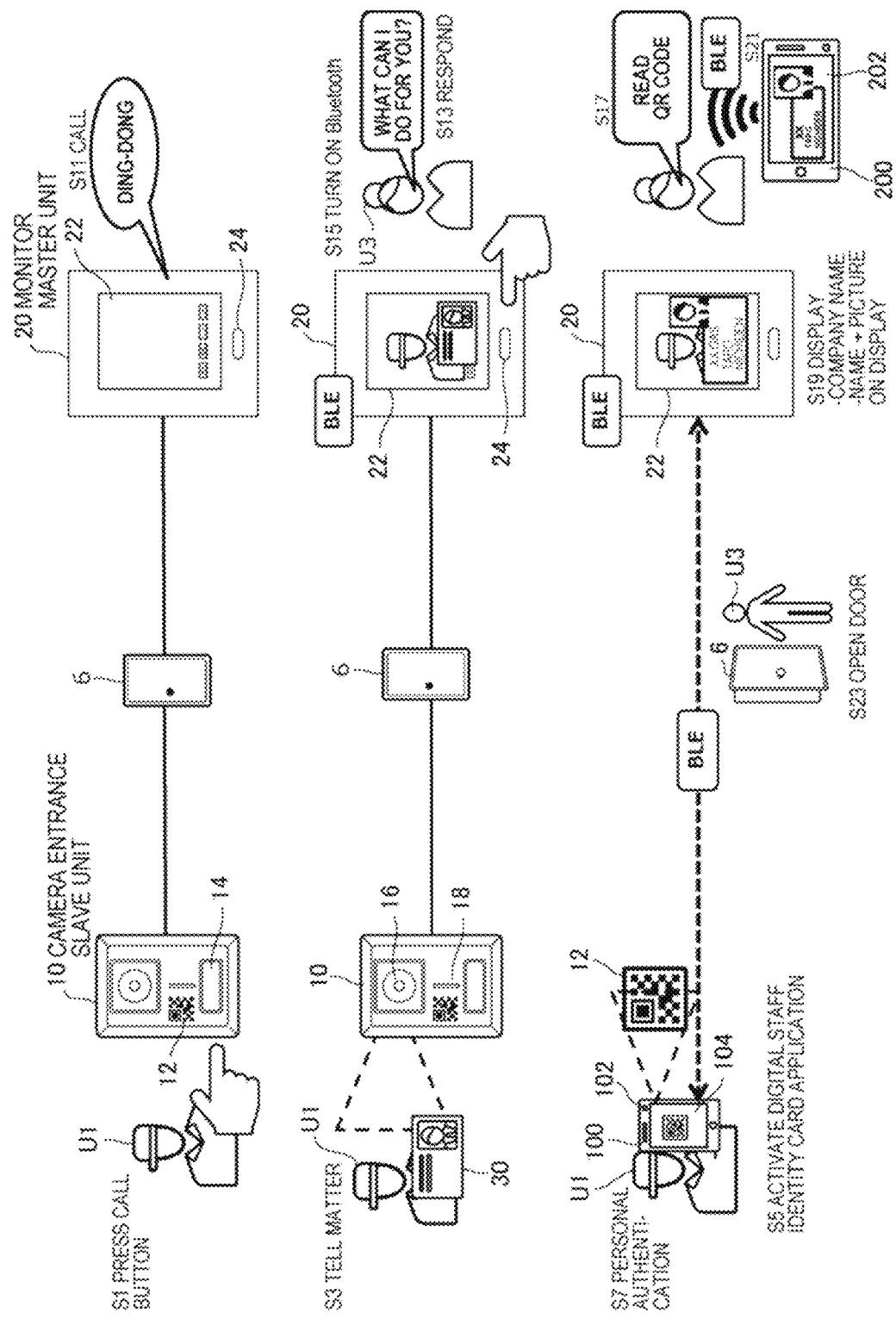

FIG. 7

```
● deuterolysin 179  TDCKGIAESSLTTALSNAAKLANQA-AEAAESGIESK-FEEYFKTTDQQIPTTVAERLPA  236
                    + C       + L+ A +LA A A     G+ES+ + +YF        P T    + A
  ▓ Asp f2     54   SSCNATQRRQIEAGLNEAVELAPHAKAHILPWCNESEIYRKYFCN----PPT----MEA  104

●            237  VAKEAGSTSG---GSTTYRCNDPYGYCEPNVLAYTLPSKN----EIANCDIYYSKLPPLAQK  291
                    V        +G    + + C++P G C            N  E   CD Y+    L
  ▓            105  VGAYDVIVNGDKANVLFRCDNPDGNCALEGWGGHKRGANATSETVICDPSYTTPRWLVSM  164

●            292  CHAQD-----------QATTTLHEFTHAPGVYQPGTEDLSYGYDAATQLSAQDALNKA-D  339
                    C +Q             A+ +H   H P V Q  +   GYD   L+  +  + D
  ▓            165  C-SQGYTVAGSETNTFWASDLMHRLYHVEAVGQGWVDHFADGYDEVIALAKSNGTESTHD  223

●            340  SYALYAHAIE  349
                    S AL    A+E
  ▓            224  SEALQYFALE  233
```

FIG. 8

```
◆ MEP20 176  ASCSSSRASALSTALRNAGSLA-NAAASAASSGSSTR-FQEYFKTTSRRP--ENVGGRFR  231
             +SC+ ++   +   L  A  LA +A A      G+ +  +++YF    RP   E  VG
■ Asp f2  54 SSCHATQRRQIEAGLNEAVELARHAKAHILRNGNESEIYRKYF----GNRPTMEAVGAYDV 110

◆       232  AVGREASSQESGKTTYYCNDPYGYCDSNTLAYTLPSSNLIAN---CDIYYSYLPALTSSC  288
             V    +  ++         + C++P G C          +N   +    CD Y+   L S C
■       111  IVNGERAN-----VLFRCENPDGNCALEGWGGEWRGANATSETVICERSYTTRRWLVSNC 165

◆       289  HAQD-----------QATTTLHEFTHAPAVYSPGTDDYAYGYRASTALSAS           329
             +Q                A+  +H  H PAV    D  +A  GY     AL+  S
■       166  -SQGYTVAGSETNTFWASDLHRLYHVFAVGQGWVDHFALGYDEVIALARS           215
```

FIG. 12

SEQ ID NO:30

```
  1 MAALLRLAVL LPLAAPLVAT LPTSPVPIAA RATPHEPVFF SWDAGAVTSF
 51 PIHSSCNATQ RRQIEAGLNE AVELARHAKA HILRWGNESE IYRKYFGNRP
101 TMEAVGAYDV IVNGDKANVL FRCDNPDGNC ALEGWGGHWR GANATSETVI
151 CDRSYTTRRW LVSMCSQGYT VAGSETNTFW ASDLMHRLYH VPAVGQGWVD
201 HFADGYDEVI ALAKSNGTES THDSEALQYF ALEAYAFDIA APGVGCAGES
251 HGPDQGHDTG SASAPASTST SSSSSGSGSG ATTTPTDSPS ATIDVPSNCH
301 THEGGQLHCT HHHHHH
```

Amino acid sequence of fusion protein Trx-SMT3-Asp f2 [aa 32-310] (SEQ ID NO: 6):
MSDKIIHLTDDSFDTDVLKADGAILVDFWAEWCGPCKMIAPILDEIADEYQGKLTVAKL
NIDQNPGTAPKYGIRGIPTLLLFKNGEVAATKVGALSKGQLKEFLDANLAGSGSGHMHH
HHHHSSGLVPRGSGMKETAAAKFERQHMDSPDLGTDDDDKAMGGHHHHHHGGGGM
SDSEVNQEAKPEVKPEVKPETHINLKVSDGSSEIFFKIKKTTPLRRLMEAFAKRQGKEMD
SLRFLYDGIRIQADQTPEDLDMEDNDIIEAHREQIGGATPHEPVFFSWDAGAVTSFPIHSS
CNATQRRQIEAGLNEAVELARHAKAHILRWGNESEIYRKYFGNRPTMEAVGAYDVIVN
GDKANVLFRCDNPDGNCALEGWGGHWRGANATSETVICDRSYTTRRWLVSMCSQGY
TVAGSETNTFWASDLMHRLYHVPAVGQGWVDHFADGYDEVIALAKSNGTESTHDSEA
LQYFALEAYAFDIAAPGVGCAGESHGPDQGHDTGSASAPASTSTSSSSSGSGSGATTTPT
DSPSATIDVPSNCHTHEGGQLHCT

DNA sequence of fusion protein Trx-SMT3-Asp f2 [aa 32-310] (SEQ ID NO: 7):
atgagcgataaaattattcacctgactgacgacagttttgacacggatgtactcaaagcggacggggcgatcctcgtcgatttctgggcaga
gtggtgcggtccgtgcaaaatgatcgccccgattctggatgaaatcgctgacgaatatcagggcaaactgaccgttgcaaaactgaacatc
gatcaaaaccctggcactgcgccgaaatatggcatccgtggtatcccgactctgctgctgttcaaaaacggtgaagtggcggcaaccaaag
tgggtgcactgtctaaaggtcagttgaaagagttcctcgacgctaacctggccggttctggttctggccatatgcaccatcatcatcatcattct
tctggtctggtgccacgcggttctggtatgaaagaaaccgctgctgctaaattcgaacgccagcacatggacagcccagatctgggtaccg
acgacgacgacaaggccatggggaggtcatcatcatcaccatcatggtggtggcggtatgagcgatagcgaagttaatcaagaagcaaaac
cggaagttaaacctgaagtgaaaccggaaacccatattaacctgaaagttagtgatggcagcagcgagatcttctttaaaatcaaaaaaacc
acaccgctgcgtcgtctgatggaagcatttgcaaaacgtcagggtaaagaaatggatagcctgcgttttctgtatgatggtattcgtattcagg
cagatcagacaccggaagatctggatatggaagataacgatattatcgaagcacatcgtgagcagattggtggtgcaacaccgcatgaacc
ggtgttttttagctgggatgccggtgcagttaccagctttccgattcatagcagctgtaatgcaacccagcgtcgccagattgaagcaggtctg
aatgaagcagttgaactggcacgtcatgcaaaagcacatattctgcgttgggtaatgaaagcgaaatctatcgtaaatactttggcaatcgtc
cgacaatggaagccgttggtgcatatgatgttattgtgaatggtgataaagccaacgttctgtttcgttgtgataatccggatggtaattgtgcac
tggaaggttggggtggtcattggcgtggtgcaaatgcgaccagcgaaaccgttatttgtgatcgtagctataccacccgtcgttggctggtta
gcatgtgtagccagggttataccgttgcaggtagcgaaaccaataccttttgggcaagcgatctgatgcatcgtctgtatcatgttccggcagt
tggtcagggttgggttgatcattttgcagatggctatgatgaagttattgcactggcaaaaagcaatggcaccgaaagcacccatgatagtga
agcactgcagtattttgccctggaagcatatgcctttgatattgcagcaccgggtgttggttgtgccggtgaaagtcatggtccggatcagggt
catgataccggtagcgcaagcgcaccggcaagcaccagcaccagctcaagcagcagcgggagcggttcaggtgcaaccaccacccg
accgatagcccgagcgcaaccattgatgttccgagcaattgtcatacccatgaaggtggtcagctgcattgtacctaa

FIG. 22

Monoclonal antibody 5D7A1 VH CDR1 amino acid sequence (SEQ ID NO: 8):
GYTFTTYT

Monoclonal antibody 5D7A1 VH CDR1 DNA sequence (SEQ ID NO: 9):
ggctacacctttacaacctacacg Monoclonal antibody 5D7A1 VL CDR1 amino acid sequence (SEQ ID NO: 10):
QNVETN Monoclonal antibody 5D7A1 VL CDR1 DNA sequence (SEQ ID NO: 11):
cagaatgtagagactaat

FIG. 23

Monoclonal antibody 5D7A1 VH CDR2 amino acid sequence (SEQ ID NO: 12):
INPSSGYT

Monoclonal antibody 5D7A1 VH CDR2 DNA sequence (SEQ ID NO: 13):
attaatcctagtagtggttatact Monoclonal antibody 5D7A1 VL CDR2 amino acid sequence (SEQ ID NO: 14):
SAS Monoclonal antibody 5D7A1 VL CDR2 DNA sequence (SEQ ID NO: 15):
tcggcatcc

FIG. 24

Monoclonal antibody 5D7A1 VH CDR3 amino acid sequence (SEQ ID NO: 16):
LRRPYRSHGGWFFDV

Monoclonal antibody 5D7A1 VH CDR3 DNA sequence (SEQ ID NO: 17):
ttaagaaggccttataggtcccacgggggctggttcttcgatgtc

Monoclonal antibody 5D7A1 VL CDR3 amino acid sequence (SEQ ID NO: 18):
QQYNTYPLT

Monoclonal antibody 5D7A1 VL CDR3 DNA sequence (SEQ ID NO: 19):
tcagcaatataacacctatccgctcacgtt

V$_L$-GS15-V$_H$-Fc scFv amino acid sequence (SEQ ID NO: 20):
METDTLLLWVLLLWVPGSTGDIVMTQSQKFMSTSVGDRVSVTCKASQNVETNVAWYQ
QKLGQSPKALIYSASFRTSGVPDRFTGSGSGTDFTLTINNVQSEDLAEYFCQQYNTYPLT
FGAGTKLELKAMALQASGGGGSGGGGSGGGGSASEVQLEESGAELARPGASVKMSCK
ASGYTFTTYTMHWVKQRPGQGLEWIGYINPSSGYTNYNQKFKDKATLTANKSSSIGYM
QLSSLTSEDSALYYCLRRPYRSHGGWFFDVWGAGTTVTVSSVEPKSCDKTHTCPPCPAP
ELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVY
TLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGK

V$_L$-GS15-V$_H$-Fc scFv DNA sequence within pEE12.4 vector (SEQ ID NO: 21):
atggaaaccgacaccctgctgctgtgggtgctgctgctgtgggtgccaggatctacaggcgacattgtgatgacccagtctcaaaaattcat
gtccacatcagtaggagacagggtcagcgtcacctgcaaggccagtcagaatgtagagactaatgtagcctggtatcaacagaaactagg
gcaatctcctaaagcactgatttactcggcatccttccggaccagtggagtccctgatcgcttcacaggcagtggatctgggacagatttcact
ctcaccatcaacaatgtgcagtctgaagacttggcagagtatttctgtcagcaatataacacctatccgctcacgttcggtgctgggaccaag
ctggagctgaaagccatggctctgcaggctagtggtggtggtggttctggtggtggtggttctggtggtggtggttctgctagcgaggtcca
gctggaggagtcaggggctgaattggcaagacctggggcctcagtgaagatgtcctgcaaggcttctggctacacctttacaacctacacg
atgcactgggtaaaacagaggcctggacagggtctggaatggattggatacattaatcctagtagtggttatactaattacaatcaaaagttca
agacaaggccacattgactgcaaacaaatcctccagtatcggctacatgcagctgagcagcctaacatctgaggattctgcactttattattg
tttaagaaggccttataggtcccacggggggctggttcttcgatgtctggggcgcagggaccacggtcaccgtctcctctgtagaacccaaat
cttgcgacaaaactcacacatgcccaccgtgcccagcacctgaactcctggggggaccgtcagtcttcctcttccccccaaaacccaagga
caccctcatgatctcccggacccctgaggtcacatgcgtggtggtggacgtgagccacgaagaccctgaggtcaagttcaactggtacgtg
gacggcgtggaggtgcataatgccaagacaaagccgcgggaggagcagtacaacagcacgtaccgtgtggtcagcgtcctcaccgtcct
gcaccaggactggctgaatggcaaggagtacaagtgcaaggtctccaacaaagccctcccagcccccatcgagaaaaccatctccaaag
ccaaagggcagccccgagaaccacaggtgtacaccctgccaccatcacgagatgagctgaccaagaaccaggtcagcctgacctgcct
ggtcaaaggcttctatcccagcgacatcgccgtggagtgggagagcaatgggcagccggagaacaactacaagaccacgcctcccgtg
ctggactccgacggctccttcttcctctacagcaagctcaccgtggacaagagcaggtggcagcaggggaacgtcttctcatgctccgtgat
gcatgaggctctgcacaaccactacacgcagaagagcctctctctgtctccgggaaa FIG. 29 (continued)

FIG. 30

V<sub>H</sub>-GS15-V<sub>L</sub>-Fc scFv amino acid sequence (SEQ ID NO: 22):
METDTLLLWVLLLWVPGSTGEVQLEESGAELARPGASVKMSCKASGYTFTTYTMHWV
KQRPGQGLEWIGYINPSSGYTNYNQKFKDKATLTANKSSSIGYMQLSSLTSEDSALYYC
LRRPYRSHGGWFFDVWGAGTTVTVSSAMALQASGGGGSGGGGSGGGGSASDIVMTQS
QKFMSTSVGDRVSVTCKASQNVETNVAWYQQKLGQSPKALIYSASFRTSGVPDRFTGS
GSGTDFTLTINNVQSEDLAEYFCQQYNTYPLTFGAGTKLELKVEPKSCDKTHTCPPCPAP
ELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVY
TLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGK

V<sub>H</sub>-GS15-V<sub>L</sub>-Fc scFv DNA sequence within pEE12.4 vector (SEQ ID NO: 23):
atggaaaccgacaccctgctgctgtgggtgctgctgctgtgggtgccaggatctacaggcgaggtccagctggaggagtcaggggctga
attggcaagacctggggcctcagtgaagatgtcctgcaaggcttctggctacacctttacaacctacacgatgcactgggtaaaacagagg
cctggacagggtctggaatggattggatacattaatcctagtagtggttatactaattacaatcaaaagttcaaagacaaggccacattgactg
caaacaaatcctccagtatcggctacatgcagctgagcagcctaacatctgaggattctgcactttattattgttaagaaggccttataggtcc
cacggggggctggttcttcgatgtctggggcgcagggaccacggtcaccgtctcctcagccatggctctgcaggctagtggtggtggtggtt
ctggtggtggtggttctggtggtggtggttctgctagcgacattgtgatgacccagtctcaaaaattcatgtccacatcagtaggagacagggt
cagcgtcacctgcaaggccagtcagaatgtagagactaatgtagcctggtatcaacagaaactagggcaatcctaaagcactgatttact
cggcatccttccggaccagtggagtccctgatcgcttcacaggcagtggatctgggacagatttcactctcaccatcaacaatgtgcagtctg
aagacttggcagagtatttctgtcagcaatataacacctatccgctcacgttcggtgctgggaccaagctggagctgaaagtagaacccaaa
tcttgcgacaaaactcacacatgcccaccgtgcccagcacctgaactcctggggggaccgtcagtcttcctcttccccccaaaacccaagg
acaccctcatgatctcccggacccctgaggtcacatgcgtggtggtggacgtgagccacgaagaccctgaggtcaagttcaactggtacgt
ggacggcgtggaggtgcataatgccaagacaaagccgcgggaggagcagtacaacagcacgtaccgtgtggtcagcgtcctcaccgtc
ctgcaccaggactggctgaatggcaaggagtacaagtgcaaggtctccaacaaagccctcccagcccccatcgagaaaaccatctccaa
agccaaagggcagccccgagaaccacaggtgtacaccctgcccccatcccgggatgagctgaccaagaaccaggtcagcctgacctgc
ctggtcaaaggcttctatcccagcgacatcgccgtggagtgggagagcaatgggcagccggagaacaactacaagaccacgcctcccgt
gctggactccgacggctccttcttcctctacagcaagctcaccgtggacaagagcaggtggcagcaggggaacgtcttctcatgctccgtg
atgcatgaggctctgcacaaccactacacgcagaagagcctctctctgtctccgggaaa

SEQUENCE LISTING

<160> NUMBER OF SEQ ID NOS: 39

<210> SEQ ID NO 1
<211> LENGTH: 139
<212> TYPE: PRT
<213> ORGANISM: Artificial Sequence
<220> FEATURE:
<223> OTHER INFORMATION: mAb 5D7A1 VH domain

<400> SEQUENCE: 1

Leu Pro Glu Phe Glu Val Gln Leu Glu Glu Ser Gly Ala Glu Leu Ala
1               5                   10                  15

Arg Pro Gly Ala Ser Val Lys Met Ser Cys Lys Ala Ser Gly Tyr Thr
            20                  25                  30

Phe Thr Thr Tyr Thr Met His Trp Val Lys Gln Arg Pro Gly Gln Gly
        35                  40                  45

Leu Glu Trp Ile Gly Tyr Ile Asn Pro Ser Ser Gly Tyr Thr Asn Tyr
    50                  55                  60

Asn Gln Lys Phe Lys Asp Lys Ala Thr Leu Thr Ala Asn Lys Ser Ser
65                  70                  75                  80

Ser Ile Gly Tyr Met Gln Leu Ser Ser Leu Thr Ser Glu Asp Ser Ala
                85                  90                  95

Leu Tyr Tyr Cys Leu Arg Arg Pro Tyr Arg Ser His Gly Gly Trp Phe
            100                 105                 110

Phe Asp Val Trp Gly Ala Gly Thr Thr Val Thr Val Ser Ser Ala Lys
        115                 120                 125

Thr Thr Pro Pro Ser Val Tyr Arg Ser Ser Lys
    130                 135

<210> SEQ ID NO 2
<211> LENGTH: 145
<212> TYPE: PRT
<213> ORGANISM: Artificial Sequence
<220> FEATURE:
<223> OTHER INFORMATION: mAb 5D7A1 VL domain

<400> SEQUENCE: 2

Met Glu Ser Gln Thr Gln Val Phe Val Tyr Met Leu Leu Trp Leu Ser
1               5                   10                  15

Gly Val Asp Gly Asp Ile Val Met Thr Gln Ser Gln Lys Phe Met Ser
            20                  25                  30

Thr Ser Val Gly Asp Arg Val Ser Val Thr Cys Lys Ala Ser Gln Asn
        35                  40                  45

Val Glu Thr Asn Val Ala Trp Tyr Gln Gln Lys Leu Gly Gln Ser Pro
    50                  55                  60

Lys Ala Leu Ile Tyr Ser Ala Ser Phe Arg Thr Ser Gly Val Pro Asp
65                  70                  75                  80

Arg Phe Thr Gly Ser Gly Ser Gly Thr Asp Phe Thr Leu Thr Ile Asn
                85                  90                  95

Asn Val Gln Ser Glu Asp Leu Ala Glu Tyr Phe Cys Gln Gln Tyr Asn
            100                 105                 110

Thr Tyr Pro Leu Thr Phe Gly Ala Gly Thr Lys Leu Glu Leu Lys Arg
        115                 120                 125

Ala Asp Ala Ala Pro Thr Val Ser Ile Ser His His Pro Val Leu Glu
    130                 135                 140

Ser
145

<210> SEQ ID NO 3
<211> LENGTH: 417
<212> TYPE: DNA
<213> ORGANISM: Artificial Sequence
<220> FEATURE:
<223> OTHER INFORMATION: mAb 5D7A1 VH domain

<400> SEQUENCE: 3

```
cttccggaat tcgaggtcca gctggaggag tcaggggctg aattggcaag acctggggcc        60
tcagtgaaga tgtcctgcaa ggcttctggc tacacctta caacctacac gatgcactgg        120
gtaaaacaga ggcctggaca gggtctggaa tggattggat acattaatcc tagtagtggt       180
tatactaatt acaatcaaaa gttcaaagac aaggccacat tgactgcaaa caaatcctcc       240
agtatcggct acatgcagct gagcagccta acatctgagg attctgcact ttattattgt       300
ttaagaaggc cttataggtc ccacggggc tggttcttcg atgtctgggg cgcagggacc        360
acggtcaccg tctcctcagc caaaacgaca cccccatctg tctatagatc ttccaag          417
```

<210> SEQ ID NO 4
<211> LENGTH: 435
<212> TYPE: DNA
<213> ORGANISM: Artificial Sequence
<220> FEATURE:
<223> OTHER INFORMATION: mAb 5D7A1 VL domain

<400> SEQUENCE: 4

```
atggagtcac agactcaggt ctttgtatac atgttgctgt ggttgtctgg tgttgatgga        60
gacattgtga tgacccagtc tcaaaaattc atgtccacat cagtaggaga cagggtcagc       120
gtcacctgca aggccagtca gaatgtagag actaatgtag cctggtatca acagaaacta      180
gggcaatctc ctaaagcact gatttactcg gcatccttcc ggaccagtgg agtccctgat      240
cgcttcacag gcagtggatc tgggacagat ttcactctca ccatcaacaa tgtgcagtct      300
gaagacttgg cagagtattt ctgtcagcaa tataacacct atccgctcac gttcggtgct      360
gggaccaagc tggagctgaa acgggctgat gctgcaccaa ctgtatccat ctcccaccat     420
ccagttctag aaagc                                                       435
```

<210> SEQ ID NO 5
<211> LENGTH: 19
<212> TYPE: PRT
<213> ORGANISM: Artificial Sequence
<220> FEATURE:
<223> OTHER INFORMATION: FluHSA2 peptide
<220> FEATURE:
<221> NAME/KEY: MISC_FEATURE
<222> LOCATION: (1)..(1)
<223> OTHER INFORMATION: T is a threonine with a 5-carboxyfluorescein
     conjugated to its alpha-amino group
<220> FEATURE:
<221> NAME/KEY: MISC_FEATURE
<222> LOCATION: (19)..(19)
<223> OTHER INFORMATION: K is a lysine with a with 4-(dimethylaminoazo)
     benzene-4-carboxy] (DABCYL) conjugated to its epsilon-amino group
     ("K[DABCYL]")

<400> SEQUENCE: 5

Thr Lys Cys Ala Thr Glu Ser Ala Val Asn Arg Arg Pro Cys Phe Ser
1               5                   10                  15

Ala Leu Lys

<210> SEQ ID NO 6
<211> LENGTH: 549

<212> TYPE: PRT
<213> ORGANISM: Artificial Sequence
<220> FEATURE:
<223> OTHER INFORMATION: Fusion protein construct Trx-SMT3-Asp f2

<400> SEQUENCE: 6

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Lys Ala Met
145                 150                 155                 160

Gly Gly His His His His His His Gly Gly Gly Met Ser Asp Ser
                165                 170                 175

Glu Val Asn Gln Glu Ala Lys Pro Glu Val Lys Pro Glu Val Lys Pro
            180                 185                 190

Glu Thr His Ile Asn Leu Lys Val Ser Asp Gly Ser Ser Glu Ile Phe
            195                 200                 205

Phe Lys Ile Lys Lys Thr Thr Pro Leu Arg Arg Leu Met Glu Ala Phe
210                 215                 220

Ala Lys Arg Gln Gly Lys Glu Met Asp Ser Leu Arg Phe Leu Tyr Asp
225                 230                 235                 240

Gly Ile Arg Ile Gln Ala Asp Gln Thr Pro Glu Asp Leu Asp Met Glu
            245                 250                 255

Asp Asn Asp Ile Ile Glu Ala His Arg Glu Gln Ile Gly Gly Ala Thr
            260                 265                 270

Pro His Glu Pro Val Phe Phe Ser Trp Asp Ala Gly Ala Val Thr Ser
        275                 280                 285

Phe Pro Ile His Ser Ser Cys Asn Ala Thr Gln Arg Arg Gln Ile Glu
290                 295                 300

Ala Gly Leu Asn Glu Ala Val Glu Leu Ala Arg His Ala Lys Ala His
305                 310                 315                 320

Ile Leu Arg Trp Gly Asn Glu Ser Glu Ile Tyr Arg Lys Tyr Phe Gly
            325                 330                 335

Asn Arg Pro Thr Met Glu Ala Val Gly Ala Tyr Asp Val Ile Val Asn
            340                 345                 350

Gly Asp Lys Ala Asn Val Leu Phe Arg Cys Asp Asn Pro Asp Gly Asn
        355                 360                 365

Cys Ala Leu Glu Gly Trp Gly Gly His Trp Arg Gly Ala Asn Ala Thr
370                 375                 380
```

```
Ser Glu Thr Val Ile Cys Asp Arg Ser Tyr Thr Arg Arg Trp Leu
385                 390                 395                 400

Val Ser Met Cys Ser Gln Gly Tyr Thr Val Ala Gly Ser Glu Thr Asn
            405                 410                 415

Thr Phe Trp Ala Ser Asp Leu Met His Arg Leu Tyr His Val Pro Ala
        420                 425                 430

Val Gly Gln Gly Trp Val Asp His Phe Ala Asp Gly Tyr Asp Glu Val
            435                 440                 445

Ile Ala Leu Ala Lys Ser Asn Gly Thr Glu Ser Thr His Asp Ser Glu
        450                 455                 460

Ala Leu Gln Tyr Phe Ala Leu Glu Ala Tyr Ala Phe Asp Ile Ala Ala
465                 470                 475                 480

Pro Gly Val Gly Cys Ala Gly Glu Ser His Gly Pro Asp Gln Gly His
            485                 490                 495

Asp Thr Gly Ser Ala Ser Ala Pro Ala Ser Thr Ser Thr Ser Ser Ser
            500                 505                 510

Ser Ser Gly Ser Gly Ser Gly Ala Thr Thr Pro Thr Asp Ser Pro
            515                 520                 525

Ser Ala Thr Ile Asp Val Pro Ser Asn Cys His Thr His Glu Gly Gly
530                 535                 540

Gln Leu His Cys Thr
545

<210> SEQ ID NO 7
<211> LENGTH: 1650
<212> TYPE: DNA
<213> ORGANISM: Artificial Sequence
<220> FEATURE:
<223> OTHER INFORMATION: Fusion protein construct Trx-SMT3-Asp f2

<400> SEQUENCE: 7
atgagcgata aaattattca cctgactgac gacagttttg acacggatgt actcaaagcg      60
gacggggcga tcctcgtcga tttctgggca gagtggtgcg gtccgtgcaa aatgatcgcc     120
ccgattctgg atgaaatcgc tgacgaatat cagggcaaac tgaccgttgc aaaactgaac     180
atcgatcaaa accctggcac tgcgccgaaa tatggcatcc gtggtatccc gactctgctg     240
ctgttcaaaa acggtgaagt ggcggcaacc aaagtgggtg cactgtctaa aggtcagttg     300
aaagagttcc tcgacgctaa cctggccggt tctggttctg ccatatgca ccatcatcat      360 catcattctt ctggtctggt gccacgcggt tctggtatga agaaaccgc tgctgctaaa      420 ttcgaacgcc agcacatgga cagcccagat ctgggtaccg acgacgacga caaggccatg     480
ggaggtcatc atcatcacca tcatggtggt ggcggtatga gcgatagcga agttaatcaa     540
gaagcaaaac cggaagttaa acctgaagtg aaaccggaaa cccatattaa cctgaaagtt     600
agtgatggca gcagcgagat cttctttaaa atcaaaaaaa ccacaccgct gcgtcgtctg     660
atggaagcat tgcaaaaacg tcagggtaaa gaaatggata gcctgcgttt tctgtatgat     720
ggtattcgta ttcaggcaga tcagacaccg gaagatctgg atatggaaga taacgatatt     780
atcgaagcac atcgtgagca gattggtggt gcaacaccgc atgaaccggt ttttttagc     840 tgggatgccg gtgcagttac cagctttccg attcatagca gctgtaatgc aacccagcgt     900
cgccagattg aagcaggtct gaatgaagca gttgaactgg cacgtcatgc aaaagcacat     960
attctgcgtt ggggtaatga agcgaaaatc tatcgtaaat actttggcaa tcgtccgaca    1020
atggaagccg ttggtgcata tgatgttatt gtgaatggtg ataaagccaa cgttctgttt    1080
```

-continued

```
cgttgtgata atccggatgg taattgtgca ctggaaggtt ggggtggtca ttggcgtggt    1140
gcaaatgcga ccagcgaaac cgttatttgt gatcgtagct ataccacccg tcgttggctg    1200
gttagcatgt gtagccaggg ttataccgtt gcaggtagcg aaaccaatac cttttgggca    1260
agcgatctga tgcatcgtct gtatcatgtt ccggcagttg gtcagggttg ggttgatcat    1320
tttgcagatg gctatgatga agttattgca ctggcaaaaa gcaatggcac cgaaagcacc    1380
catgatagtg aagcactgca gtattttgcc ctggaagcat atgcctttga tattgcagca    1440
ccgggtgttg gttgtgccgg tgaaagtcat ggtccggatc agggtcatga taccggtagc    1500
gcaagcgcac cggcaagcac cagcaccagc tcaagcagca gcggtagcgg ttcaggtgca    1560
accaccaccc cgaccgatag cccgagcgca accattgatg ttccgagcaa ttgtcatacc    1620
catgaaggtg gtcagctgca ttgtacctaa                                    1650
```

<210> SEQ ID NO 8
<211> LENGTH: 8
<212> TYPE: PRT
<213> ORGANISM: Artificial Sequence
<220> FEATURE:
<223> OTHER INFORMATION: mAb 5D7A1 VH CDR1

<400> SEQUENCE: 8

Gly Tyr Thr Phe Thr Thr Tyr Thr
1               5

<210> SEQ ID NO 9
<211> LENGTH: 24
<212> TYPE: DNA
<213> ORGANISM: Artificial Sequence
<220> FEATURE:
<223> OTHER INFORMATION: mAb 5D7A1 VH CDR1

<400> SEQUENCE: 9
ggctacacct ttacaaccta cacg                                            24

<210> SEQ ID NO 10
<211> LENGTH: 6
<212> TYPE: PRT
<213> ORGANISM: Artificial Sequence
<220> FEATURE:
<223> OTHER INFORMATION: mAb 5D7A1 VL CDR1

<400> SEQUENCE: 10

Gln Asn Val Glu Thr Asn
1               5

<210> SEQ ID NO 11
<211> LENGTH: 18
<212> TYPE: DNA
<213> ORGANISM: Artificial Sequence
<220> FEATURE:
<223> OTHER INFORMATION: mAb 5D7A1 VL CDR1

<400> SEQUENCE: 11
cagaatgtag agactaat                                                   18

<210> SEQ ID NO 12
<211> LENGTH: 8
<212> TYPE: PRT
<213> ORGANISM: Artificial Sequence
<220> FEATURE:
<223> OTHER INFORMATION: mAb 5D7A1 VH CDR2

<400> SEQUENCE: 12

Ile Asn Pro Ser Ser Gly Tyr Thr
1               5

<210> SEQ ID NO 13
<211> LENGTH: 24
<212> TYPE: DNA
<213> ORGANISM: Artificial Sequence
<220> FEATURE:
<223> OTHER INFORMATION: mAb 5D7A1 VH CDR2

<400> SEQUENCE: 13
attaatccta gtagtggtta tact                                           24

<210> SEQ ID NO 14
<211> LENGTH: 3
<212> TYPE: PRT
<213> ORGANISM: Artificial Sequence
<220> FEATURE:
<223> OTHER INFORMATION: mAb 5D7A1 VL CDR2

<400> SEQUENCE: 14

Ser Ala Ser
1

<210> SEQ ID NO 15
<211> LENGTH: 9
<212> TYPE: DNA
<213> ORGANISM: Artificial Sequence
<220> FEATURE:
<223> OTHER INFORMATION: mAb 5D7A1 VL CDR2

<400> SEQUENCE: 15 tcggcatcc                                                             9

<210> SEQ ID NO 16
<211> LENGTH: 15
<212> TYPE: PRT
<213> ORGANISM: Artificial Sequence
<220> FEATURE:
<223> OTHER INFORMATION: mAb 5D7A1 VH CDR3

<400> SEQUENCE: 16

Leu Arg Arg Pro Tyr Arg Ser His Gly Gly Trp Phe Phe Asp Val
1               5                   10                  15

<210> SEQ ID NO 17
<211> LENGTH: 45
<212> TYPE: DNA
<213> ORGANISM: Artificial Sequence
<220> FEATURE:
<223> OTHER INFORMATION: mAb 5D7A1 VH CDR3

<400> SEQUENCE: 17
ttaagaaggc cttataggtc ccacgggggc tggttcttcg atgtc                    45

<210> SEQ ID NO 18
<211> LENGTH: 9
<212> TYPE: PRT
<213> ORGANISM: Artificial Sequence
<220> FEATURE:
<223> OTHER INFORMATION: mAb 5D7A1 VL CDR3

<400> SEQUENCE: 18

Gln Gln Tyr Asn Thr Tyr Pro Leu Thr
1               5

<210> SEQ ID NO 19
<211> LENGTH: 30
<212> TYPE: DNA
<213> ORGANISM: Artificial Sequence
<220> FEATURE:
<223> OTHER INFORMATION: mAb 5D7A1 VL CDR3

<400> SEQUENCE: 19
tcagcaatat aacacctatc cgctcacgtt          30

<210> SEQ ID NO 20
<211> LENGTH: 506
<212> TYPE: PRT
<213> ORGANISM: Artificial Sequence
<220> FEATURE:
<223> OTHER INFORMATION: VL-GS15-VH-Fc scFv

<400> SEQUENCE: 20

```
Met Glu Thr Asp Thr Leu Leu Leu Trp Val Leu Leu Leu Trp Val Pro
1               5                   10                  15

Gly Ser Thr Gly Asp Ile Val Met Thr Gln Ser Gln Lys Phe Met Ser
            20                  25                  30

Thr Ser Val Gly Asp Arg Val Ser Val Thr Cys Lys Ala Ser Gln Asn
        35                  40                  45

Val Glu Thr Asn Val Ala Trp Tyr Gln Gln Lys Leu Gly Gln Ser Pro
    50                  55                  60

Lys Ala Leu Ile Tyr Ser Ala Ser Phe Arg Thr Ser Gly Val Pro Asp
65                  70                  75                  80

Arg Phe Thr Gly Ser Gly Ser Gly Thr Asp Phe Thr Leu Thr Ile Asn
                85                  90                  95

Asn Val Gln Ser Glu Asp Leu Ala Glu Tyr Phe Cys Gln Gln Tyr Asn
            100                 105                 110

Thr Tyr Pro Leu Thr Phe Gly Ala Gly Thr Lys Leu Glu Leu Lys Ala
        115                 120                 125

Met Ala Leu Gln Ala Ser Gly Gly Gly Ser Gly Gly Gly Gly Ser
    130                 135                 140

Gly Gly Gly Gly Ser Ala Ser Glu Val Gln Leu Glu Glu Ser Gly Ala
145                 150                 155                 160

Glu Leu Ala Arg Pro Gly Ala Ser Val Lys Met Ser Cys Lys Ala Ser
                165                 170                 175

Gly Tyr Thr Phe Thr Thr Tyr Thr Met His Trp Val Lys Gln Arg Pro
            180                 185                 190

Gly Gln Gly Leu Glu Trp Ile Gly Tyr Ile Asn Pro Ser Ser Gly Tyr
        195                 200                 205

Thr Asn Tyr Asn Gln Lys Phe Lys Asp Lys Ala Thr Leu Thr Ala Asn
    210                 215                 220

Lys Ser Ser Ser Ile Gly Tyr Met Gln Leu Ser Ser Leu Thr Ser Glu
225                 230                 235                 240

Asp Ser Ala Leu Tyr Tyr Cys Leu Arg Arg Pro Tyr Arg Ser His Gly
                245                 250                 255

Gly Trp Phe Phe Asp Val Trp Gly Ala Gly Thr Thr Val Thr Val Ser
            260                 265                 270

Ser Val Glu Pro Lys Ser Cys Asp Lys Thr His Thr Cys Pro Pro Cys
        275                 280                 285

Pro Ala Pro Glu Leu Leu Gly Gly Pro Ser Val Phe Leu Phe Pro Pro
    290                 295                 300
```

| | | | | | | | | | | | |
|---|---|---|---|---|---|---|---|---|---|---|---|
|Lys|Pro|Lys|Asp|Thr|Leu|Met|Ile|Ser|Arg|Thr|Pro|Glu|Val|Thr|Cys|
|305| | | | |310| | | | |315| | | | |320|

Val Val Val Asp Val Ser His Glu Asp Pro Glu Val Lys Phe Asn Trp
              325                        330                        335

Tyr Val Asp Gly Val Glu Val His Asn Ala Lys Thr Lys Pro Arg Glu
              340                        345                        350

Glu Gln Tyr Asn Ser Thr Tyr Arg Val Val Ser Val Leu Thr Val Leu
          355                        360                        365

His Gln Asp Trp Leu Asn Gly Lys Glu Tyr Lys Cys Lys Val Ser Asn
          370                        375                        380

Lys Ala Leu Pro Ala Pro Ile Glu Lys Thr Ile Ser Lys Ala Lys Gly
385                        390                        395                        400

Gln Pro Arg Glu Pro Gln Val Tyr Thr Leu Pro Pro Ser Arg Asp Glu
          405                        410                        415

Leu Thr Lys Asn Gln Val Ser Leu Thr Cys Leu Val Lys Gly Phe Tyr
              420                        425                        430

Pro Ser Asp Ile Ala Val Glu Trp Glu Ser Asn Gly Gln Pro Glu Asn
          435                        440                        445

Asn Tyr Lys Thr Thr Pro Pro Val Leu Asp Ser Asp Gly Ser Phe Phe
450                        455                        460

Leu Tyr Ser Lys Leu Thr Val Asp Lys Ser Arg Trp Gln Gln Gly Asn
465                        470                        475                        480

Val Phe Ser Cys Ser Val Met His Glu Ala Leu His Asn His Tyr Thr
              485                        490                        495

Gln Lys Ser Leu Ser Leu Ser Pro Gly Lys
          500                        505

<210> SEQ ID NO 21
<211> LENGTH: 1518
<212> TYPE: DNA
<213> ORGANISM: Artificial Sequence
<220> FEATURE:
<223> OTHER INFORMATION: VL-GS15-VH-Fc scFv within pEE12.4 vector

<400> SEQUENCE: 21

```
atggaaaccg acaccctgct gctgtgggtg ctgctgctgt gggtgccagg atctacaggc      60
gacattgtga tgacccagtc tcaaaaattc atgtccacat cagtaggaga cagggtcagc     120
gtcacctgca aggccagtca gaatgtagag actaatgtag cctggtatca acagaaacta     180
gggcaatctc ctaaagcact gatttactcg gcatccttcc ggaccagtgg agtccctgat     240
cgcttcacag gcagtggatc tgggacagat ttcactctca ccatcaacaa tgtgcagtct     300
gaagacttgg cagagtattt ctgtcagcaa tataacacct atccgctcac gttcggtgct     360
gggaccaagc tggagctgaa agccatggct ctgcaggcta gtggtggtgg tggttctggt     420
ggtggtggtt ctggtggtgg tggttctgct agcgaggtcc agctggagga gtcaggggct     480
gaattggcaa gacctggggc tcagtgaaga tgtcctgca aggcttctgg ctacaccttt     540
acaacctaca cgatgcactg ggtaaaacag aggcctggac agggtctgga atggattgga     600
tacattaatc ctagtagtgg ttatactaat acaatcaaa agttcaaaga caaggccaca     660
ttgactgcaa acaaatcctc cagtatcggc tacatgcagc tgagcagcct aacatctgag     720
gattctgcac tttattattg tttaagaagg ccttataggt cccacggggg ctggttcttc     780
gatgtctggg gcgcagggac cacggtcacc gtctcctctg tagaacccaa atcttgcgac     840
aaaactcaca catgcccacc gtgcccagca cctgaactcc tggggggacc gtcagtcttc     900
```

```
ctcttccccc caaaacccaa ggacaccctc atgatctccc ggacccctga ggtcacatgc    960
gtggtggtgg acgtgagcca cgaagaccct gaggtcaagt tcaactggta cgtggacggc   1020
gtggaggtgc ataatgccaa gacaaagccg cgggaggagc agtacaacag cacgtaccgt   1080
gtggtcagcg tcctcaccgt cctgcaccag gactggctga atggcaagga gtacaagtgc   1140
aaggtctcca acaaagccct cccagccccc atcgagaaaa ccatctccaa agccaaaggg   1200
cagccccgag aaccacaggt gtacaccctg ccaccatcac gagatgagct gaccaagaac   1260
caggtcagcc tgacctgcct ggtcaaaggc ttctatccca gcgacatcgc cgtggagtgg   1320
gagagcaatg ggcagccgga gaacaactac aagaccacgc ctcccgtgct ggactccgac   1380
ggctccttct tcctctacag caagctcacc gtggacaaga gcaggtggca gcaggggaac   1440
gtcttctcat gctccgtgat gcatgaggct ctgcacaacc actacacgca gaagagcctc   1500
tctctgtctc ccgggaaa                                                 1518
```

<210> SEQ ID NO 22
<211> LENGTH: 506
<212> TYPE: PRT
<213> ORGANISM: Artificial Sequence
<220> FEATURE:
<223> OTHER INFORMATION: VH-GS15-VL-Fc scFv

<400> SEQUENCE: 22

```
Met Glu Thr Asp Thr Leu Leu Leu Trp Val Leu Leu Leu Trp Val Pro
1               5                   10                  15

Gly Ser Thr Gly Glu Val Gln Leu Glu Glu Ser Gly Ala Glu Leu Ala
            20                  25                  30

Arg Pro Gly Ala Ser Val Lys Met Ser Cys Lys Ala Ser Gly Tyr Thr
        35                  40                  45

Phe Thr Thr Tyr Thr Met His Trp Val Lys Gln Arg Pro Gly Gln Gly
    50                  55                  60

Leu Glu Trp Ile Gly Tyr Ile Asn Pro Ser Ser Gly Tyr Thr Asn Tyr
65                  70                  75                  80

Asn Gln Lys Phe Lys Asp Lys Ala Thr Leu Thr Ala Asn Lys Ser Ser
                85                  90                  95

Ser Ile Gly Tyr Met Gln Leu Ser Ser Leu Thr Ser Glu Asp Ser Ala
            100                 105                 110

Leu Tyr Tyr Cys Leu Arg Arg Pro Tyr Arg Ser His Gly Gly Trp Phe
        115                 120                 125

Phe Asp Val Trp Gly Ala Gly Thr Thr Val Thr Val Ser Ser Ala Met
    130                 135                 140

Ala Leu Gln Ala Ser Gly Gly Gly Ser Gly Gly Gly Ser Gly
145                 150                 155                 160

Gly Gly Gly Ser Ala Ser Asp Ile Val Met Thr Gln Ser Gln Lys Phe
                165                 170                 175

Met Ser Thr Ser Val Gly Asp Arg Val Ser Val Thr Cys Lys Ala Ser
            180                 185                 190

Gln Asn Val Glu Thr Asn Val Ala Trp Tyr Gln Gln Lys Leu Gly Gln
        195                 200                 205

Ser Pro Lys Ala Leu Ile Tyr Ser Ala Ser Phe Arg Thr Ser Gly Val
    210                 215                 220

Pro Asp Arg Phe Thr Gly Ser Gly Ser Gly Thr Asp Phe Thr Leu Thr
225                 230                 235                 240

Ile Asn Asn Val Gln Ser Glu Asp Leu Ala Glu Tyr Phe Cys Gln Gln
                245                 250                 255
```

Tyr Asn Thr Tyr Pro Leu Thr Phe Gly Ala Gly Thr Lys Leu Glu Leu
                260                 265                 270

Lys Val Glu Pro Lys Ser Cys Asp Lys Thr His Thr Cys Pro Pro Cys
            275                 280                 285

Pro Ala Pro Glu Leu Leu Gly Gly Pro Ser Val Phe Leu Phe Pro Pro
        290                 295                 300

Lys Pro Lys Asp Thr Leu Met Ile Ser Arg Thr Pro Glu Val Thr Cys
305                 310                 315                 320

Val Val Val Asp Val Ser His Glu Asp Pro Glu Val Lys Phe Asn Trp
                325                 330                 335

Tyr Val Asp Gly Val Glu Val His Asn Ala Lys Thr Lys Pro Arg Glu
            340                 345                 350

Glu Gln Tyr Asn Ser Thr Tyr Arg Val Val Ser Val Leu Thr Val Leu
        355                 360                 365

His Gln Asp Trp Leu Asn Gly Lys Glu Tyr Lys Cys Lys Val Ser Asn
    370                 375                 380

Lys Ala Leu Pro Ala Pro Ile Glu Lys Thr Ile Ser Lys Ala Lys Gly
385                 390                 395                 400

Gln Pro Arg Glu Pro Gln Val Tyr Thr Leu Pro Pro Ser Arg Asp Glu
                405                 410                 415

Leu Thr Lys Asn Gln Val Ser Leu Thr Cys Leu Val Lys Gly Phe Tyr
            420                 425                 430

Pro Ser Asp Ile Ala Val Glu Trp Glu Ser Asn Gly Gln Pro Glu Asn
        435                 440                 445

Asn Tyr Lys Thr Thr Pro Pro Val Leu Asp Ser Asp Gly Ser Phe Phe
    450                 455                 460

Leu Tyr Ser Lys Leu Thr Val Asp Lys Ser Arg Trp Gln Gln Gly Asn
465                 470                 475                 480

Val Phe Ser Cys Ser Val Met His Glu Ala Leu His Asn His Tyr Thr
                485                 490                 495

Gln Lys Ser Leu Ser Leu Ser Pro Gly Lys
            500                 505

<210> SEQ ID NO 23
<211> LENGTH: 1518
<212> TYPE: DNA
<213> ORGANISM: Artificial Sequence
<220> FEATURE:
<223> OTHER INFORMATION: VL-GS15-VH-Fc scFv within pEE12.4 vector

<400> SEQUENCE: 23
atggaaaccg acaccctgct gctgtgggtg ctgctgctgt gggtgccagg atctacaggc      60
gaggtccagc tggaggagtc aggggctgaa ttggcaagac tgggggcctc agtgaagatg     120
tcctgcaagg cttctggcta cacctttaca acctacacga tgcactgggt aaaacagagg     180
cctggacagg gtctggaatg gattggatac attaatccta gtagtggtta tactaattac     240
aatcaaaagt tcaaagacaa ggccacattg actgcaaaca atcctccag tatcggctac      300 atgcagctga gcagcctaac atctgaggat tctgcacttt attattgttt aagaaggcct     360
tataggtccc acgggggctg gttcttcgat gtctggggcg cagggaccac ggtcaccgtc     420
tcctcagcca tggctctgca ggctagtggt ggtggtggtt ctggtggtgg tggttctggt     480
ggtggtggtt ctgctagcga cattgtgatg acccagtctc aaaaattcat gtccacatca     540
gtaggagaca gggtcagcgt cacctgcaag gccagtcaga atgtagagac taatgtagcc     600

```
tggtatcaac agaaactagg gcaatctcct aaagcactga tttactcggc atccttccgg      660
accagtggag tccctgatcg cttcacaggc agtggatctg ggacagattt cactctcacc      720
atcaacaatg tgcagtctga agacttggca gagtatttct gtcagcaata taacacctat      780
ccgctcacgt tcggtgctgg gaccaagctg gagctgaaag tagaacccaa atcttgcgac      840
aaaactcaca catgcccacc gtgcccagca cctgaactcc tggggggacc gtcagtcttc      900
ctcttccccc caaaacccaa ggacaccctc atgatctccc ggacccctga ggtcacatgc      960
gtggtggtgg acgtgagcca cgaagaccct gaggtcaagt tcaactggta cgtggacggc     1020
gtggaggtgc ataatgccaa gacaaagccg cgggaggagc agtacaacag cacgtaccgt     1080
gtggtcagcg tcctcaccgt cctgcaccag gactggctga atggcaagga gtacaagtgc     1140
aaggtctcca acaaagccct cccagccccc atcgagaaaa ccatctccaa agccaaaggg     1200
cagccccgag aaccacaggt gtacaccctg cccccatccc gggatgagct gaccaagaac     1260
caggtcagcc tgacctgcct ggtcaaaggc ttctatccca gcgacatcgc cgtggagtgg     1320
gagagcaatg ggcagccgga gaacaactac aagaccacgc tcccgtgct ggactccgac     1380 ggctccttct cctctacag caagctcacc gtggacaaga gcaggtggca gcaggggaac     1440
gtcttctcat gctccgtgat gcatgaggct ctgcacaacc actacacgca gaagagcctc     1500
tctctgtctc cgggaaa                                                   1518
```

<210> SEQ ID NO 24
<211> LENGTH: 1100
<212> TYPE: DNA
<213> ORGANISM: Artificial Sequence
<220> FEATURE:
<223> OTHER INFORMATION: 5D7A1 Antibody and surrounding vector sequence

<400> SEQUENCE: 24

```
tgattacgcc aagcttggta ccgagctcgg atccactagt aacggccgcc agtgtgctgg       60
aattcggctt cttccggaat tcgaggtcca gctggaggag tcaggggctg aattggcaag      120
acctggggcc tcagtgaaga tgtcctgcaa ggcttctggc tacacctta caacctacac      180 gatgcactgg gtaaaacaga ggcctggaca gggtctggaa tggattggat acattaatcc      240
tagtagtggt tatactaatt acaatcaaaa gttcaaagac aaggccacat tgactgcaaa      300
caaatcctcc agtatcggct acatgcagct gagcagccta acatctgagg attctgcact      360
ttattattgt ttaagaaggc cttataggtc ccacggggc tggttcttcg atgtctgggg      420
cgcagggacc acggtcaccg tctcctcagc caaaacgaca cccccatctg tctatagatc      480
ttccaagccg aattctgcag ctctagatgc atgctcgagc ggccgccagt gtgatggata      540
tctgcagaat tcggcttgat atccaccatg gagtcacaga ctcaggtctt tgtatacatg      600
ttgctgtggt tgtctggtgt tgatggagac attgtgatga cccagtctca aaaattcatg      660
tccacatcag taggagacag ggtcagcgtc acctgcaagg ccagtcagaa tgtagagact      720
aatgtagcct ggtatcaaca gaaactaggg caatctccta aagcactgat ttactcggca      780
tccttccgga ccagtggagt ccctgatcgc ttcacaggca gtggatctgg gacagatttc      840
actctcacca tcaacaatgt gcagtctgaa gacttggcag agtatttctg tcagcaatat      900
aacacctatc cgctcacgtt cggtgctggg accaagctgg agctgaaacg ggctgatgct      960
gcaccaactg tatccatctc ccaccatcca gttctagaaa gccgaattcc agcacactgg     1020
cggccgttac tagtggatcc gagctcggta ccaagcttgg cgtaatcatg gtcatagctg     1080
tttcctgtgt gaaattgtta                                                 1100
```

<210> SEQ ID NO 25
<211> LENGTH: 1100
<212> TYPE: DNA
<213> ORGANISM: Artificial Sequence
<220> FEATURE:
<223> OTHER INFORMATION: 5D7A1 Antibody and surrounding vector sequence
(Reverse Complement DNA)

<400> SEQUENCE: 25

```
taacaatttc acacaggaaa cagctatgac catgattacg ccaagcttgg taccgagctc      60
ggatccacta gtaacggccg ccagtgtgct ggaattcggc tttctagaac tggatggtgg     120
gagatggata cagttggtgc agcatcagcc cgtttcagct ccagcttggt cccagcaccg     180
aacgtgagcg ataggtgtt atattgctga cagaaatact ctgccaagtc ttcagactgc      240
acattgttga tggtgagagt gaaatctgtc ccagatccac tgcctgtgaa gcgatcaggg     300
actccactgg tccggaagga tgccgagtaa atcagtgctt taggagattg ccctagtttc     360
tgttgatacc aggctacatt agtctctaca ttctgactgg ccttgcaggt gacgctgacc     420
ctgtctccta ctgatgtgga catgaatttt tgagactggg tcatcacaat gtctccatca     480
acaccagaca accacagcaa catgtataca aagacctgag tctgtgactc catggtggat     540
atcaagccga attctgcaga tatccatcac actggcggcc gctcgagcat gcatctagag     600
ctgcagaatt cggcttggaa gatctataga cagatggggg tgtcgttttg ctgaggaga     660
cggtgaccgt ggtccctgcg ccccagacat cgaagaacca gccccgtgg gacctataag     720
gccttcttaa acaataataa agtgcagaat cctcagatgt taggctgctc agctgcatgt     780
agccgatact ggaggatttg tttgcagtca atgtggcctt gtctttgaac ttttgattgt     840
aattagtata accactacta ggattaatgt atccaatcca ttccagaccc tgtccaggcc     900
tctgttttac ccagtgcatc gtgtaggttg taaaggtgta gccagaagcc ttgcaggaca     960
tcttcactga ggccccaggt cttgccaatt cagcccctga ctcctccagc tggacctcga    1020
attccggaag aagccgaatt ccagcacact ggcggccgtt actagtggat ccgagctcgg    1080
taccaagctt ggcgtaatca                                                1100
```

<210> SEQ ID NO 26
<211> LENGTH: 171
<212> TYPE: PRT
<213> ORGANISM: Aspergillus oryzae
<220> FEATURE:
<221> NAME/KEY: MISC_FEATURE
<223> OTHER INFORMATION: Portion of Deuterolysin Protein (amino acids
179-349)

<400> SEQUENCE: 26

Thr Asp Cys Lys Gly Asp Ala Glu Ser Ser Leu Thr Thr Ala Leu Ser
1               5                   10                  15

Asn Ala Ala Lys Leu Ala Asn Gln Ala Ala Glu Ala Ala Glu Ser Gly
            20                  25                  30

Asp Glu Ser Lys Phe Glu Glu Tyr Phe Lys Thr Thr Asp Gln Gln Thr
        35                  40                  45

Arg Thr Thr Val Ala Glu Arg Leu Arg Ala Val Ala Lys Glu Ala Gly
    50                  55                  60

Ser Thr Ser Gly Gly Ser Thr Thr Tyr His Cys Asn Asp Pro Tyr Gly
65                  70                  75                  80

Tyr Cys Glu Pro Asn Val Leu Ala Tyr Thr Leu Pro Ser Lys Asn Glu
                85                  90                  95

```
Ile Ala Asn Cys Asp Ile Tyr Tyr Ser Glu Leu Pro Pro Leu Ala Gln
                100                 105                 110

Lys Cys His Ala Gln Asp Gln Ala Thr Thr Leu His Glu Phe Thr
            115                 120                 125

His Ala Pro Gly Val Tyr Gln Pro Gly Thr Glu Asp Leu Gly Tyr Gly
        130                 135                 140

Tyr Asp Ala Ala Thr Gln Leu Ser Ala Gln Asp Ala Leu Asn Asn Ala
145                 150                 155                 160

Asp Ser Tyr Ala Leu Tyr Ala Asn Ala Ile Glu
                165                 170
```

<210> SEQ ID NO 27
<211> LENGTH: 180
<212> TYPE: PRT
<213> ORGANISM: Aspergillus fumigatus
<220> FEATURE:
<221> NAME/KEY: MISC_FEATURE
<223> OTHER INFORMATION: Portion of Asp f2 protein (amino acids 54-233)

<400> SEQUENCE: 27

```
Ser Ser Cys Asn Ala Thr Gln Arg Arg Gln Ile Glu Ala Gly Leu Asn
1               5                   10                  15

Glu Ala Val Glu Leu Ala Arg His Ala Lys Ala His Ile Leu Arg Trp
                20                  25                  30

Gly Asn Glu Ser Glu Ile Tyr Arg Lys Tyr Phe Gly Asn Arg Pro Thr
            35                  40                  45

Met Glu Ala Val Gly Ala Tyr Asp Val Ile Val Asn Gly Asp Lys Ala
 50                 55                  60

Asn Val Leu Phe Arg Cys Asp Asn Pro Asp Gly Asn Cys Ala Leu Glu
65                  70                  75                  80

Gly Trp Gly Gly His Trp Arg Gly Ala Asn Ala Thr Ser Glu Thr Val
                85                  90                  95

Ile Cys Asp Arg Ser Tyr Thr Thr Arg Arg Trp Leu Val Ser Met Cys
            100                 105                 110

Ser Gln Gly Tyr Thr Val Ala Gly Ser Glu Thr Asn Thr Phe Trp Ala
        115                 120                 125

Ser Asp Leu Met His Arg Leu Tyr His Val Pro Ala Val Gly Gln Gly
    130                 135                 140

Trp Val Asp His Phe Ala Asp Gly Tyr Asp Glu Val Ile Ala Leu Ala
145                 150                 155                 160

Lys Ser Asn Gly Thr Glu Ser Thr His Asp Ser Glu Ala Leu Gln Tyr
                165                 170                 175

Phe Ala Leu Glu
        180
```

<210> SEQ ID NO 28
<211> LENGTH: 153
<212> TYPE: PRT
<213> ORGANISM: Aspergillus fumigatus
<220> FEATURE:
<221> NAME/KEY: MISC_FEATURE
<223> OTHER INFORMATION: Portion of MEP20 protein (amino acids 176-328)

<400> SEQUENCE: 28

```
Ala Ser Cys Ser Gly Ser Arg Ala Ser Ala Leu Ser Thr Ala Leu Arg
1               5                   10                  15

Asn Ala Gly Ser Leu Ala Asn Ala Ala Ala Ser Ala Ala Ser Ser Gly
                20                  25                  30
```

```
Ser Ser Thr Arg Phe Gln Glu Tyr Phe Lys Thr Thr Ser Arg Arg Pro
        35                  40                  45

Glu Asn Val Gly Gly Arg Phe Arg Ala Val Gly Arg Glu Ala Ser Ser
 50                  55                  60

Gln Ser Ser Gly Lys Thr Thr Tyr Tyr Cys Asn Asp Pro Tyr Gly Tyr
65                   70                  75                  80

Cys Asp Ser Asn Thr Leu Ala Tyr Thr Leu Pro Ser Ser Asn Leu Ile
                 85                  90                  95

Ala Asn Cys Asp Ile Tyr Tyr Ser Tyr Leu Pro Ala Leu Thr Ser Ser
                100                 105                 110

Cys His Ala Gln Asp Gln Ala Thr Thr Thr Leu His Glu Phe Thr His
                115                 120                 125

Ala Pro Ala Val Tyr Ser Pro Gly Thr Asp Asp Tyr Ala Tyr Gly Tyr
            130                 135                 140

Arg Ala Ser Thr Ala Leu Ser Ala Ser
145                 150
```

<210> SEQ ID NO 29
<211> LENGTH: 162
<212> TYPE: PRT
<213> ORGANISM: Aspergillus fumigatus
<220> FEATURE:
<221> NAME/KEY: MISC_FEATURE
<223> OTHER INFORMATION: Portion of Asp f2 protein (amino acids 54-215)

<400> SEQUENCE: 29

```
Ser Ser Cys Asn Ala Thr Gln Arg Arg Gln Ile Glu Ala Gly Leu Asn
 1               5                  10                  15

Glu Ala Val Glu Leu Ala Arg His Ala Lys Ala His Ile Leu Arg Trp
             20                  25                  30

Gly Asn Glu Ser Glu Ile Tyr Arg Lys Tyr Phe Gly Asn Arg Pro Thr
                 35                  40                  45

Met Glu Ala Val Gly Ala Tyr Asp Val Ile Val Asn Gly Asp Lys Ala
 50                  55                  60

Asn Val Leu Phe Arg Cys Asp Asn Pro Asp Gly Asn Cys Ala Leu Glu
65                   70                  75                  80

Gly Trp Gly Gly His Trp Arg Gly Ala Asn Ala Thr Ser Glu Thr Val
                 85                  90                  95

Ile Cys Asp Arg Ser Tyr Thr Thr Arg Arg Trp Leu Val Ser Met Cys
                100                 105                 110

Ser Gln Gly Tyr Thr Val Ala Gly Ser Glu Thr Asn Thr Phe Trp Ala
            115                 120                 125

Ser Asp Leu Met His Arg Leu Tyr His Val Pro Ala Val Gly Gln Gly
            130                 135                 140

Trp Val Asp His Phe Ala Asp Gly Tyr Asp Glu Val Ile Ala Leu Ala
145                 150                 155                 160

Lys Ser
```

<210> SEQ ID NO 30
<211> LENGTH: 316
<212> TYPE: PRT
<213> ORGANISM: Aspergillus fumigatus
<220> FEATURE:
<221> NAME/KEY: MISC_FEATURE
<223> OTHER INFORMATION: Full length recombinant Asp f2

<400> SEQUENCE: 30

Met Ala Ala Leu Leu Arg Leu Ala Val Leu Leu Pro Leu Ala Ala Pro
1               5                   10                  15

Leu Val Ala Thr Leu Pro Thr Ser Pro Val Pro Ile Ala Ala Arg Ala
            20                  25                  30

Thr Pro His Glu Pro Val Phe Phe Ser Trp Asp Ala Gly Ala Val Thr
            35                  40                  45

Ser Phe Pro Ile His Ser Ser Cys Asn Ala Thr Gln Arg Arg Gln Ile
50                  55                  60

Glu Ala Gly Leu Asn Glu Ala Val Glu Leu Ala Arg His Ala Lys Ala
65                  70                  75                  80

His Ile Leu Arg Trp Gly Asn Glu Ser Glu Ile Tyr Arg Lys Tyr Phe
                85                  90                  95

Gly Asn Arg Pro Thr Met Glu Ala Val Gly Ala Tyr Asp Val Ile Val
                100                 105                 110

Asn Gly Asp Lys Ala Asn Val Leu Phe Arg Cys Asp Asn Pro Asp Gly
            115                 120                 125

Asn Cys Ala Leu Glu Gly Trp Gly Gly His Trp Arg Gly Ala Asn Ala
130                 135                 140

Thr Ser Glu Thr Val Ile Cys Asp Arg Ser Tyr Thr Thr Arg Arg Trp
145                 150                 155                 160

Leu Val Ser Met Cys Ser Gln Gly Tyr Thr Val Ala Gly Ser Glu Thr
                165                 170                 175

Asn Thr Phe Trp Ala Ser Asp Leu Met His Arg Leu Tyr His Val Pro
            180                 185                 190

Ala Val Gly Gln Gly Trp Val Asp His Phe Ala Asp Gly Tyr Asp Glu
            195                 200                 205

Val Ile Ala Leu Ala Lys Ser Asn Gly Thr Glu Ser Thr His Asp Ser
210                 215                 220

Glu Ala Leu Gln Tyr Phe Ala Leu Glu Ala Tyr Ala Phe Asp Ile Ala
225                 230                 235                 240

Ala Pro Gly Val Gly Cys Ala Gly Glu Ser His Gly Pro Asp Gln Gly
                245                 250                 255

His Asp Thr Gly Ser Ala Ser Ala Pro Ala Ser Thr Ser Thr Ser Ser
            260                 265                 270

Ser Ser Ser Gly Ser Gly Ser Gly Ala Thr Thr Pro Thr Asp Ser
            275                 280                 285

Pro Ser Ala Thr Ile Asp Val Pro Ser Asn Cys His Thr His Glu Gly
            290                 295                 300

Gly Gln Leu His Cys Thr His His His His His
305                 310                 315

<210> SEQ ID NO 31
<211> LENGTH: 1650
<212> TYPE: DNA
<213> ORGANISM: Artificial Sequence
<220> FEATURE:
<223> OTHER INFORMATION: Trx-SMT3-Asp f2 fusion protein construct
      (Reverse complement DNA)

<400> SEQUENCE: 31
ttaggtacaa tgcagctgac caccttcatg ggtatgacaa ttgctcggaa catcaatggt    60
tgcgctcggg ctatcggtcg gggtggtggt tgcacctgaa ccgctaccgc tgctgcttga   120
gctggtgctg gtgcttgccg gtgcgcttgc gctaccggta tcatgaccct gatccggacc   180
atgactttca ccggcacaac caacacccgg tgctgcaata tcaaaggcat atgcttccag   240

```
ggcaaaatac tgcagtgctt cactatcatg ggtgctttcg gtgccattgc ttttgccag      300 tgcaataact tcatcatagc catctgcaaa atgatcaacc caaccctgac caactgccgg      360
aacatgatac agacgatgca tcagatcgct tgcccaaaag gtattggttt cgctacctgc      420
aacggtataa ccctggctac acatgctaac cagccaacga cgggtggtat agctacgatc      480
acaaataacg gtttcgctgg tcgcatttgc accacgccaa tgaccacccc aaccttccag      540
tgcacaatta ccatccggat tatcacaacg aaacagaacg ttggctttat caccattcac      600
aataacatca tatgcaccaa cggcttccat tgtcggacga ttgccaaagt atttacgata      660
gatttcgctt tcattacccc aacgcagaat atgtgctttt gcatgacgtg ccagttcaac      720
tgcttcattc agacctgctt caatctggcg acgctgggtt gcattacagc tgctatgaat      780
cggaaagctg gtaactgcac cggcatccca gctaaaaaac accggttcat gcggtgttgc      840
accaccaatc tgctcacgat gtgcttcgat aatatcgtta tcttccatat ccagatcttc      900
cggtgtctga tctgcctgaa tacgaatacc atcatacaga aaacgcaggc tatccatttc      960
tttaccctga cgttttgcaa atgcttccat cagacgacga agcggtgtgg tttttttgat     1020
tttaaagaag atctcgctgc tgccatcact aactttcagg ttaatatggg tttccggttt     1080
cacttcaggt ttaacttccg gttttgcttc ttgattaact tcgctatcgc tcataccgcc     1140
accaccatga tggtgatgat gatgacctcc catggccttg tcgtcgtcgt cggtacccag     1200
atctgggctg tccatgtgct ggcgttcgaa tttagcagca gcggtttctt tcataccaga     1260
accgcgtggc accagaccag aagaatgatg atgatgatgg tgcatatggc cagaaccaga     1320
accggccagg ttagcgtcga ggaactcttt caactgacct ttagacagtg cacccacttt     1380
ggttgccgcc acttcaccgt ttttgaacag cagcagagtc gggataccac ggatgccata     1440
tttcggcgca gtgccagggt tttgatcgat gttcagtttt gcaacggtca gtttgccctg     1500
atattcgtca gcgatttcat ccagaatcgg ggcgatcatt ttgcacggac cgcaccactc     1560
tgcccagaaa tcgacgagga tcgccccgtc cgctttgagt acatccgtgt caaaactgtc     1620
gtcagtcagg tgaataattt tatcgctcat                                      1650
```

<210> SEQ ID NO 32
<211> LENGTH: 1700
<212> TYPE: DNA
<213> ORGANISM: Artificial Sequence
<220> FEATURE:
<223> OTHER INFORMATION: VL-GS15-VH-Fc scFv and surrounding pEE12.4
      vector sequence

<400> SEQUENCE: 32

```
tagctgacag actaacagac tgttcctttc catgggtctt ttctgcagtc accgtccttg       60
acacgaagct tgccgccacc atggaaaccg acaccctgct gctgtgggtg ctgctgctgt      120
gggtgccagg atctacaggc gacattgtga tgacccagtc tcaaaaattc atgtccacat      180
cagtaggaga cagggtcagc gtcacctgca aggccagtca gaatgtagag actaatgtag      240
cctggtatca acagaaacta ggcaatctc ctaaagcact gatttactcg gcatccttcc      300
ggaccagtgg agtccctgat cgcttcacag gcagtggatc tgggacagat ttcactctca      360
ccatcaacaa tgtgcagtct gaagacttgg cagagtattt ctgtcagcaa tataacacct      420
atccgctcac gttcggtgct gggaccaagc tggagctgaa agccatggct ctgcaggcta      480
gtggtggtgg tggttctggt ggtggtggtt ctggtggtgg tggttctgct agcgaggtcc      540
agctggagga gtcaggggct gaattggcaa gacctggggc ctcagtgaag atgtcctgca      600
```

| | |
|---|---|
| aggcttctgg ctacaccttt acaacctaca cgatgcactg ggtaaaacag aggcctggac | 660 |
| agggtctgga atggattgga tacattaatc ctagtagtgg ttatactaat tacaatcaaa | 720 |
| agttcaaaga caaggccaca ttgactgcaa acaaatcctc cagtatcggc tacatgcagc | 780 |
| tgagcagcct aacatctgag gattctgcac tttattattg tttaagaagg ccttataggt | 840 |
| cccacggggg ctggttcttc gatgtctggg gcgcagggac cacggtcacc gtctcctctg | 900 |
| tagaacccaa atcttgcgac aaaactcaca catgcccacc gtgcccagca cctgaactcc | 960 |
| tgggggacc gtcagtcttc ctcttccccc caaaacccaa ggacaccctc atgatctccc | 1020 |
| ggacccctga ggtcacatgc gtggtggtgg acgtgagcca cgaagaccct gaggtcaagt | 1080 |
| tcaactggta cgtggacggc gtggaggtgc ataatgccaa gacaaagccg cgggaggagc | 1140 |
| agtacaacag cacgtaccgt gtggtcagcg tcctcaccgt cctgcaccag gactggctga | 1200 |
| atggcaagga gtacaagtgc aaggtctcca acaaagccct cccagccccc atcgagaaaa | 1260 |
| ccatctccaa agccaagggg cagccccgag aaccacaggt gtacaccctg ccaccatcac | 1320 |
| gagatgagct gaccaagaac caggtcagcc tgacctgcct ggtcaaaggc ttctatccca | 1380 |
| gcgacatcgc cgtggagtgg gagagcaatg ggcagccgga gaacaactac aagaccacgc | 1440 |
| ctcccgtgct ggactccgac ggctccttct tcctctacag caagctcacc gtggacaaga | 1500 |
| gcaggtggca gcaggggaac gtcttctcat gctccgtgat gcatgaggct ctgcacaacc | 1560 |
| actacacgca gaagagcctc tctctgtctc ccgggaaata ggaattcatt gatcataatc | 1620 |
| agccatacca catttgtaga ggttttactt gctttaaaaa acctcccaca cctcccctg | 1680 |
| aacctgaaac ataaaatgaa | 1700 |

<210> SEQ ID NO 33
<211> LENGTH: 1700
<212> TYPE: DNA
<213> ORGANISM: Artificial Sequence
<220> FEATURE:
<223> OTHER INFORMATION: VL-GS15-VH-Fc scFv and surrounding pEE12.4
    vector sequence (Reverse complement DNA)

<400> SEQUENCE: 33

| | |
|---|---|
| ttcattttat gtttcaggtt caggggagg tgtgggaggt ttttaaagc aagtaaaacc | 60 |
| tctacaaatg tggtatggct gattatgatc aatgaattcc tatttcccgg gagacagaga | 120 |
| gaggctcttc tgcgtgtagt ggttgtgcag agcctcatgc atcacggagc atgagaagac | 180 |
| gttcccctgc tgccacctgc tcttgtccac ggtgagcttg ctgtagagga agaaggagcc | 240 |
| gtcggagtcc agcacgggag gcgtggtctt gtagttgttc tccggctgcc cattgctctc | 300 |
| ccactccacg gcgatgtcgc tgggatagaa gcctttgacc aggcaggtca ggctgacctg | 360 |
| gttcttggtc agctcatctc gtgatggtgg caggtgtac acctgtggtt ctcggggctg | 420 |
| cccttggct ttggagatgg ttttctcgat gggggctggg agggctttgt ggagaccttt | 480 |
| gcacttgtac tccttgccat tcagccagtc ctggtgcagg acggtgagga cgctgaccac | 540 |
| acggtacgtg ctgttgtact gctcctcccg cggctttgtc ttggcattat gcacctccac | 600 |
| gccgtccacg taccagttga acttgacctc agggtcttcg tggctcacgt ccaccaccac | 660 |
| gcatgtgacc tcaggggtcc gggagatcat gagggtgtcc ttgggttttg ggggaagag | 720 |
| gaagactgac ggtccccca ggagttcagg tgctgggcac ggtgggcatg tgtgagtttt | 780 |
| gtcgcaagat ttgggttcta cagaggagac ggtgaccgtg gtcctgcgc ccagacatc | 840 |
| gaagaaccag ccccgtggg acctataagg ccttcttaaa caataataaa gtgcagaatc | 900 |

```
ctcagatgtt aggctgctca gctgcatgta gccgatactg gaggatttgt ttgcagtcaa      960
tgtggccttg tctttgaact tttgattgta attagtataa ccactactag gattaatgta     1020
tccaatccat tccagaccct gtccaggcct ctgttttacc cagtgcatcg tgtaggttgt     1080
aaaggtgtag ccagaagcct tgcaggacat cttcactgag gccccaggtc ttgccaattc     1140
agcccctgac tcctccagct ggacctcgct agcagaacca ccaccaccag aaccaccacc     1200
accagaacca ccaccaccac tagcctgcag agccatggct ttcagctcca gcttggtccc     1260
agcaccgaac gtgagcggat aggtgttata ttgctgacag aaatactctg ccaagtcttc     1320
agactgcaca ttgttgatgg tgagagtgaa atctgtccca gatccactgc ctgtgaagcg     1380
atcagggact ccactggtcc ggaaggatgc cgagtaaatc agtgctttag gagattgccc     1440
tagtttctgt tgataccagg ctacattagt ctctacattc tgactggcct tgcaggtgac     1500
gctgaccctg tctcctactg atgtggacat gaattttga gactgggtca tcacaatgtc     1560
gcctgtagat cctggcaccc acagcagcag cacccacagc agcagggtgt cggtttccat     1620
ggtggcggca agcttcgtgt caaggacggt gactgcagaa aagacccatg aaaggaaca     1680 gtctgttagt ctgtcagcta                                                 1700
```

<210> SEQ ID NO 34
<211> LENGTH: 1700
<212> TYPE: DNA
<213> ORGANISM: Artificial Sequence
<220> FEATURE:
<223> OTHER INFORMATION: VH-GS15-VL-Fc scFv and surrounding pEE12.4
      vector sequence

<400> SEQUENCE: 34

```
tagctgacag actaacagac tgttcctttc catgggtctt ttctgcagtc accgtccttg       60
acacgaagct tgccgccacc atggaaaccg acaccctgct gctgtgggtg ctgctgctgt      120
gggtgccagg atctacaggc gaggtccagc tggaggagtc aggggctgaa ttggcaagac      180
ctggggcctc agtgaagatg tcctgcaagg cttctggcta cacctttaca acctacacga      240
tgcactgggt aaaacagagg cctggacagg gtctggaatg gattggatac attaatccta      300
gtagtggtta ctaattac aatcaaaagt tcaaagacaa ggccacattg actgcaaaca      360
aatcctccag tatcggctac atgcagctga gcagcctaac atctgaggat tctgcacttt      420
attattgttt aagaaggcct tataggtccc acggggctg gttcttcgat gtctggggcg      480
cagggaccac ggtcaccgtc tcctcagcca tggctctgca ggctagtggt ggtggtggtt      540
ctggtggtgg tggttctggt ggtggtggtt ctgctagcga cattgtgatg cccagtctc      600 aaaaattcat gtccacatca gtaggagaca gggtcagcgt cacctgcaag gccagtcaga      660
atgtagagac taatgtagcc tggtatcaac agaaactagg gcaatctcct aaagcactga      720
tttactcggc atccttccgg accagtggag tccctgatcg cttcacaggc agtggatctg      780
ggacagattt cactctcacc atcaacaatg tgcagtctga agacttggca gagtattct      840 gtcagcaata taacacctat ccgctcacgt tcggtgctgg gaccaagctg gagctgaaag      900
tagaacccaa atcttgcgac aaaactcaca catgcccacc gtgcccagca cctgaactcc      960 tgggggggacc gtcagtcttc ctcttcccc caaaacccaa ggacaccctc atgatctccc     1020 ggaccctga ggtcacatgc gtggtggtgg acgtgagcca cgaagaccct gaggtcaagt     1080
tcaactggta cgtggacggc gtggaggtgc ataatgccaa gacaaagccg cgggaggagc     1140
agtacaacag cacgtaccgt gtggtcagcg tcctcaccgt cctgcaccag gactggctga     1200
```

| | |
|---|---|
| atggcaagga gtacaagtgc aaggtctcca acaaagccct cccagccccc atcgagaaaa | 1260 |
| ccatctccaa agccaaaggg cagccccgag aaccacaggt gtacaccctg cccccatccc | 1320 |
| gggatgagct gaccaagaac caggtcagcc tgacctgcct ggtcaaaggc ttctatccca | 1380 |
| gcgacatcgc cgtggagtgg gagagcaatg ggcagccgga gaacaactac aagaccacgc | 1440 |
| ctcccgtgct ggactccgac ggctccttct tcctctacag caagctcacc gtggacaaga | 1500 |
| gcaggtggca gcaggggaac gtcttctcat gctccgtgat gcatgaggct ctgcacaacc | 1560 |
| actacacgca gaagagcctc tctctgtctc ccgggaaata ggaattcatt gatcataatc | 1620 |
| agccatacca catttgtaga ggttttactt gctttaaaaa acctcccaca cctcccccctg | 1680 |
| aacctgaaac ataaaatgaa | 1700 |

<210> SEQ ID NO 35
<211> LENGTH: 1700
<212> TYPE: DNA
<213> ORGANISM: Artificial Sequence
<220> FEATURE:
<223> OTHER INFORMATION: VH-GS15-VL-Fc scFv and surrounding pEE12.4
    vector sequence (Reverse complement DNA)

<400> SEQUENCE: 35

| | |
|---|---|
| ttcattttat gtttcaggtt cagggggagg tgtgggaggt tttttaaagc aagtaaaacc | 60 |
| tctacaaatg tggtatggct gattatgatc aatgaattcc tatttcccgg gagacagaga | 120 |
| gaggctcttc tgcgtgtagt ggttgtgcag agcctcatgc atcacggagc atgagaagac | 180 |
| gttcccctgc tgccacctgc tcttgtccac ggtgagcttg ctgtagagga agaaggagcc | 240 |
| gtcggagtcc agcacgggag gcgtggtctt gtagttgttc tccggctgcc cattgctctc | 300 |
| ccactccacg gcgatgtcgc tgggatagaa gcctttgacc aggcaggtca ggctgacctg | 360 |
| gttcttggtc agctcatccc gggatggggg cagggtgtac acctgtggtt ctcggggctg | 420 |
| ccctttggct ttggagatgg ttttctcgat gggggctggg agggctttgt tggagacctt | 480 |
| gcacttgtac tccttgccat tcagccagtc ctggtgcagg acggtgagga cgctgaccac | 540 |
| acggtacgtg ctgttgtact gctcctcccg cggctttgtc ttggcattat gcacctccac | 600 |
| gccgtccacg taccagttga acttgacctc agggtcttcg tggctcacgt ccaccaccac | 660 |
| gcatgtgacc tcaggggtcc gggagatcat gagggtgtcc ttgggttttg ggggaagag | 720 |
| gaagactgac ggtcccccca ggagttcagg tgctgggcac ggtgggcatg tgtgagtttt | 780 |
| gtcgcaagat ttgggttcta ctttcagctc cagcttggtc ccagcaccga acgtgagcgg | 840 |
| ataggtgtta tattgctgac agaaatactc tgccaagtct tcagactgca cattgttgat | 900 |
| ggtgagagtg aaatctgtcc cagatccact gcctgtgaag cgatcaggga ctccactggt | 960 |
| ccggaaggat gccgagtaaa tcagtgcttt aggagattgc cctagtttct gttgatacca | 1020 |
| ggctacatta gtctctacat tctgactggc cttgcaggtg acgctgaccc tgtctcctac | 1080 |
| tgatgtggac atgaatttt gagactgggt catcacaatg tcgctagcag aaccaccacc | 1140 |
| accagaacca ccaccaccag aaccaccacc accactagcc tgcagagcca tggctgagga | 1200 |
| gacggtgacc gtggtccctg cgccccagac atcgaagaac cagccccgt gggacctata | 1260 |
| aggccttctt aaacaataat aaagtgcaga atcctcagat gttaggctgc tcagctgcat | 1320 |
| gtagccgata ctggaggatt tgtttgcagt caatgtggcc ttgtctttga acttttgatt | 1380 |
| gtaattagta taaccactac taggattaat gtatccaatc cattccagac cctgtccagg | 1440 |
| cctctgtttt acccagtgca tcgtgtaggt tgtaaaggtg tagccagaag ccttgcagga | 1500 |

```
catcttcact gaggccccag gtcttgccaa ttcagcccct gactcctcca gctggacctc    1560
gcctgtagat cctggcaccc acagcagcag cacccacagc agcagggtgt cggtttccat    1620
ggtggcggca agcttcgtgt caaggacggt gactgcagaa aagacccatg gaaaggaaca    1680
gtctgttagt ctgtcagcta                                                1700
```

```
<210> SEQ ID NO 36
<211> LENGTH: 5
<212> TYPE: PRT
<213> ORGANISM: Artificial Sequence
<220> FEATURE:
<223> OTHER INFORMATION: motif

<400> SEQUENCE: 36

His Arg Leu Tyr His
1               5

<210> SEQ ID NO 37
<211> LENGTH: 5
<212> TYPE: PRT
<213> ORGANISM: Artificial Sequence
<220> FEATURE:
<223> OTHER INFORMATION: motif
<220> FEATURE:
<221> NAME/KEY: misc_feature
<222> LOCATION: (3)..(4)
<223> OTHER INFORMATION: Xaa can be any naturally occurring amino acid

<400> SEQUENCE: 37

His Glu Xaa Xaa His
1               5

<210> SEQ ID NO 38
<211> LENGTH: 5
<212> TYPE: PRT
<213> ORGANISM: Artificial Sequence
<220> FEATURE:
<223> OTHER INFORMATION: motif

<400> SEQUENCE: 38

Phe Ser Ala Leu Lys
1               5

<210> SEQ ID NO 39
<211> LENGTH: 31
<212> TYPE: PRT
<213> ORGANISM: Aspergillus fumigatus
<220> FEATURE:
<221> NAME/KEY: MISC_FEATURE
<223> OTHER INFORMATION: Asp f2 signal peptide

<400> SEQUENCE: 39

Met Ala Ala Leu Leu Arg Leu Ala Val Leu Leu Pro Leu Ala Ala Pro
1               5                   10                  15

Leu Val Ala Thr Leu Pro Thr Ser Pro Val Pro Ile Ala Ala Arg
                20                  25                  30
```

US 11,726,087 B2

METHODS, COMPOSITIONS, AND KITS FOR DETECTION OF ASPERGILLOSIS

RELATED APPLICATIONS

The present application is a continuation of U.S. application Ser. No. 15/236,988, filed Aug. 15, 2016, which is a continuation of U.S. application Ser. No. 14/217,004, filed Mar. 17, 2014, issued as U.S. Pat. No. 9,416,395, which claims priority to U.S. Provisional Application No. 61/798,640, filed Mar. 15, 2013, the disclosures of which are incorporated by reference herein in their entirety, including drawings and sequence listing.

STATEMENT OF GOVERNMENT INTEREST

This invention was made with government support under Grant Number RO1 AI075230, awarded by the National Institutes of Health. The government has certain rights in the invention.

SEQUENCE LISTING

This disclosure includes a sequence listing, which is submitted in ASCII format via EFS-Web, and is hereby incorporated by reference in its entirety. The ASCII copy, created on Mar. 26, 2020, is named 8128US03_SequenceListing.txt and is 52 kilobytes in size.

BACKGROUND

*Aspergillus fumigatus* is one of the most common *Aspergillus* species known to cause disease in humans. *A. fumigatus* is the most frequent cause of invasive fungal infection in immunosuppressed individuals, which include patients receiving immunosuppressive therapy for autoimmune or neoplastic disease, organ transplant recipients, and AIDS patients. *A. fumigatus* primarily causes invasive infection in the lung and represents a major cause of morbidity and mortality in these individuals. Additionally, *A. fumigatus* can cause chronic pulmonary infections or allergic disease in immunocompetent hosts. An *A. fumigatus* infection most commonly manifests as invasive pulmonary aspergillosis.

Only a few molecular assays exist for the detection of invasive fungal infections, including galactomannan and beta-glucan as well as DNA-based assays (e.g., PCR). The galactomannan and beta-glucan assays have limitations in terms of specificity and sensitivity. For example, antifungal medication is known to interfere with the galactomannan assay. *A. fumigatus* does not release much DNA into the circulation, which limits the utility of DNA-based assays. Therefore, there is a need for a sensitive assay to detect the presence of *A. fumigatus* in a sample from an infected patient.

SUMMARY

Provided herein are novel methods for detecting the presence of an *Aspergillus* protease such as Asp f2 in a sample and for diagnosing and treating a subject with aspergillosis caused by *Aspergillus* using this detection method. Also provided herein are kits for performing these methods, as well as antibodies specific to *Aspergillus* proteases such as Asp f2 and compositions, formulations, and kits comprising these antibodies.

Provided herein in certain embodiments are methods for detecting the presence of an *Aspergillus* protease in a biological sample comprising contacting the sample with a protease substrate comprising one or more *Aspergillus* protease cleavage sites, wherein cleavage of the protease substrate indicates the presence of the *Aspergillus* protease in the sample. In certain embodiments, the *Aspergillus* protease is Asp f2 or a homologue thereof. In certain embodiments, the biological sample is from a subject suspected of suffering from aspergillosis or previously diagnosed with aspergillosis. In certain embodiments, the sample is enriched for the *Aspergillus* protease prior to contact with the protease substrate, and in certain of these embodiments enrichment is carried out using an *Aspergillus* protease-specific antibody that is free in solution or immobilized to an enrichment matrix. In certain embodiments, the protease substrate is a protein or peptide comprising the amino acid sequence of SEQ ID NO: 5, an elastin protein or peptide, or a collagen protein or peptide. In certain embodiments, the protease substrate comprises one or more fluorophores, and in certain embodiments the protease substrate further comprises one or more acceptors. In certain of these embodiments, the fluorophore and/or acceptor is conjugated to the protease substrate via a peptide bond. In certain embodiments, the protease substrate is FluHSA2.

Provided herein in certain embodiments are methods for diagnosing aspergillosis in a subject comprising obtaining a biological sample from the subject, contacting the sample with a protease substrate comprising one or more *Aspergillus* protease cleavage sites, wherein cleavage of the protease substrate indicates the presence of the *Aspergillus* protease in the sample, and diagnosing the subject with aspergillosis if the *Aspergillus* protease is present in the sample. In certain embodiments, the *Aspergillus* protease is Asp f2 or a homologue thereof. In certain embodiments, the subject is suspected of suffering from aspergillosis or has been previously diagnosed with aspergillosis. In certain embodiments, the methods further comprise administering one or more therapeutic agents for treating aspergillosis. In certain embodiments, the sample is enriched for the *Aspergillus* protease prior to contact with the protease substrate, and in certain of these embodiments enrichment is carried out using an *Aspergillus* protease-specific antibody that is free in solution or immobilized to an enrichment matrix. In certain embodiments, the protease substrate is a protein or peptide comprising the amino acid sequence of SEQ ID NO:5, an elastin protein or peptide, or a collagen protein or peptide. In certain embodiments, the protease substrate comprises one or more fluorophores, and in certain embodiments the protease substrate further comprises one or more acceptors. In certain of these embodiments, the fluorophore and/or acceptor is conjugated to the protease substrate via a peptide bond. In certain embodiments, the protease substrate is FluHSA2.

Provided herein in certain embodiments are methods for treating aspergillosis in a subject comprising obtaining a biological sample from the subject, contacting the sample with a protease substrate comprising one or more *Aspergillus* protease cleavage sites, wherein cleavage of the protease substrate indicates the presence of the *Aspergillus* protease in the sample, and administering one or more therapeutic agents to the subject if the *Aspergillus* protease is determined to be present in the sample. In certain embodiments, the *Aspergillus* protease is Asp f2 or a homologue thereof. In certain embodiments, the therapeutic agent is a therapeutic agent that has not previously been administered to the subject. In other embodiments, the therapeutic agent is an agent that was previously administered to the subject, but administered at a higher dosage. In certain embodiments, the sample is enriched for the *Aspergillus* protease prior to contact with the protease substrate, and in certain of these embodiments enrichment is carried out using an *Aspergillus* protease-specific antibody or antigen binding fragment that is free in solution or immobilized to an enrichment matrix. In certain embodiments, the protease substrate is a protein or peptide comprising the amino acid sequence of SEQ ID NO:5, an elastin protein or peptide, or a collagen protein or peptide. In certain embodiments, the protease substrate comprises one or more fluorophores, and in certain embodiments the protease substrate further comprises one or more acceptors. In certain of these embodiments, the fluorophore and/or acceptor is conjugated to the protease substrate via a peptide bond. In certain embodiments, the protease substrate is FluHSA2.

Provided herein in certain embodiments are kits for use in detecting an *Aspergillus* protease in a sample, diagnosing a subject with aspergillosis based on the presence of an *Aspergillus* protease in a sample, or treating aspergillosis in a subject. In certain embodiments, the kits comprise instructions for use. In certain embodiments, the *Aspergillus* protease is Asp f2 or a homologue thereof. In certain embodiments, the kits provided herein comprise one or more antibodies or antigen binding fragments thereof that specifically bind an *Aspergillus* protease. In certain of these embodiments, the antibodies or antigen binding fragments thereof come pre-loaded on an enrichment matrix. In other embodiments, the antibodies or antigen binding fragments are not pre-loaded on an enrichment matrix. In certain of these embodiments, the kits may further comprise an enrichment matrix or components thereof on which a user may load the antibodies or antigen fragments thereof, such as beads to which the antibodies or antigen binding fragments may be immobilized. In certain embodiments, the kits comprise a protease substrate, and in certain of these embodiments the protease substrate is a protein or peptide comprising the amino acid sequence of SEQ ID NO: 5, an elastin protein or peptide, or a collagen protein or peptide. In certain embodiments, the protease substrate comprises one or more fluorophores, and in certain embodiments the protease substrate further comprises one or more acceptors. In certain of these embodiments, the fluorophore and/or acceptor is conjugated to the protease substrate via a peptide bond. In certain embodiments, the protease substrate is FluHSA2.

Provided herein in certain embodiments are antibodies or antigen binding fragments thereof that specifically bind an *Aspergillus* protease. In certain of these embodiments, the *Aspergillus* protease is Asp f2 or a homologue thereof. In certain embodiments, these antibodies or antigen binding fragments thereof comprise one or more CDR sequences comprising the amino acid sequences set forth in SEQ ID NOs: 8, 10, 12, 14, 16, or 18 or a combination thereof, and in certain of these embodiments the antibodies or antigen binding fragments thereof comprise a light chain variable region comprising the amino acid sequence of SEQ ID NO: 2 and/or a heavy chain variable region comprising the amino acid sequence of SEQ ID NO: 1. In other embodiments, the antibodies or antigen binding fragments thereof comprise the amino acid sequence of SEQ ID NO: 20 and/or 22. In certain embodiments, the antibodies are monoclonal, chimeric, or humanized antibodies, and in certain embodiments wherein the antibodies are monoclonal the antibodies are 5D7A1. In certain embodiments, the antigen binding fragments thereof is an scFv, F(ab')2, Fab, Fab' or Fv.

Provided herein in certain embodiments are methods for detecting the presence of an *Aspergillus* protease in a sample and for determining whether a subject is suffering from aspergillosis. The methods include the steps of exposing the sample containing the *Aspergillus* protease to an enrichment matrix comprising an *Aspergillus* protease-specific antibody that binds the *Aspergillus* protease and to a substrate composition comprising a protease substrate capable of eliciting a detectable fluorescence signal when modified by the *Aspergillus* protease, and measuring the level of change in the detectable fluorescence signal and detecting the presence of the *Aspergillus* protease when the level of change in the detectable fluorescence signal in the sample is elevated. When the level of change in the detectable fluorescence signal in the sample is elevated, the subject is treated for aspergillosis.

Provided herein in certain embodiments are methods for detecting the presence of an *Aspergillus* protease in a sample comprising (a) exposing the sample to an enrichment matrix comprising an *Aspergillus* protease-specific antibody or antigen-binding fragment thereof that specifically binds the *Aspergillus* protease, (b) exposing the sample to a protease substrate capable of eliciting a detectable fluorescence signal when modified by the *Aspergillus* protease, wherein the protease substrate comprises one or more *Aspergillus* protease cleavage sites, (c) measuring the level of change in the detectable fluorescence signal; and (d) detecting the presence of the *Aspergillus* protease when the level of change in the detectable fluorescence signal in the sample is elevated. In certain embodiments, the sample is exposed to the enrichment matrix prior to exposure to the protease substrate. In other embodiments, exposure to the enrichment matrix and the protease substrate occurs simultaneously. In certain of these embodiments, the *Aspergillus* protease is Asp f2 or a homologue thereof, and in certain of these embodiments the antibody or antigen binding fragment thereof specifically binds Asp f2 or a homologue thereof. In certain embodiments, the protease substrate is a circular substrate. In certain embodiments, the protease substrate is a protein or peptide comprising the amino acid sequence of SEQ ID NO: 5, an elastin protein or peptide, or a collagen protein or peptide, and in certain embodiments the protease substrate is FluHSA2. In certain embodiments, the protease substrate comprises at least one fluorophore conjugated via a peptide bond at or near the N-terminus and at least one acceptor conjugated at or near the C-terminus. In certain of these embodiments, the acceptor is a dark quencher. In certain embodiments, the step of exposure to the enrichment matrix and/or protease substrate occurs under conditions permitting binding of the *Aspergillus* protease to the antibody or antigen binding fragment thereof and modification of the protease substrate by the *Aspergillus* protease. In certain embodiments, the antibody or antigen binding fragment thereof comprises one or more CDRs selected from the group consisting of SEQ ID NOs: 8, 10, 12, 14, 16, and 18, and in certain embodiments the antibody or antigen binding fragments thereof comprises a variable heavy chain comprising the amino acid sequence of SEQ ID NO: 1 and/or a variable light chain comprising the amino acid sequence of SEQ ID NO: 2. In certain embodiments, the antibody is the monoclonal antibody 5D7A1. In certain embodiments, the level of change in the detectable fluorescence signal is elevated if it is significantly greater than the level of change in the detectable fluorescence signal from a negative control sample. In certain embodiments, the enrichment matrix further comprises a protease substrate-specific antibody or antigen binding fragment thereof that binds the protease substrate. In certain of these embodiments, the protease substrate-specific antibody or antigen binding fragment binds a protein or peptide component of the protease substrate. In other embodiments, the antibody or fragment thereof binds a fluorophore component of the protease substrate (e.g., an anti-fluorescein antibody) or an acceptor component of the protease substrate (e.g., an anti-DABCYL antibody). In certain embodiments, the enrichment matrix is an immunosorbent support comprised of loose beads or a fixed column.

Provided herein in certain embodiments are methods for determining whether a subject is suffering from aspergillosis comprising (a) exposing a biological sample from the subject to an enrichment matrix comprising an *Aspergillus* protease-specific antibody that binds an *Aspergillus* protease, (b) exposing the sample to a protease substrate capable of eliciting a detectable fluorescence signal when modified by the *Aspergillus* protease, wherein the protease substrate comprises one or more *Aspergillus* protease cleavage sites; and (c) measuring the level of change in the detectable fluorescence signal, wherein the subject is determined to be suffering from aspergillosis when the change in the detectable fluorescence signal in the sample is elevated. In certain embodiments, the methods further comprise (d) administering one or more therapeutic agents for treating aspergillosis. In certain embodiments, the sample is exposed to the enrichment matrix prior to exposure to the protease substrate. In other embodiments, exposure to the enrichment matrix and the protease substrate occurs simultaneously. In certain of these embodiments, the *Aspergillus* protease is Asp f2 or a homologue thereof, and in certain of these embodiments the antibody or antigen binding fragment thereof specifically binds Asp f2 or a homologue thereof. In certain embodiments, the protease substrate is a circular substrate. In certain embodiments, the protease substrate is a protein or peptide comprising the amino acid sequence of SEQ ID NO: 5, an elastin protein or peptide, or a collagen protein or peptide, and in certain embodiments the protease substrate is FluHSA2. In certain embodiments, the protease substrate comprises at least one fluorophore conjugated via a peptide bond at or near the N-terminus and at least one acceptor conjugated at or near the C-terminus. In certain of these embodiments, the acceptor is a dark quencher. In certain embodiments, the step of exposure to the enrichment matrix and/or protease substrate occurs under conditions permitting binding of the *Aspergillus* protease to the antibody or antigen binding fragment thereof and modification of the protease substrate by the *Aspergillus* protease. In certain embodiments, the antibody or antigen binding fragment thereof comprises one or more CDRs selected from the group consisting of SEQ ID NOs: 8, 10, 12, 14, 16, and 18, and in certain embodiments the antibody or antigen binding fragments thereof comprises a variable heavy chain comprising the amino acid sequence of SEQ ID NO: 1 and/or a variable light chain comprising the amino acid sequence of SEQ ID NO: 2. In certain embodiments, the antibody is the monoclonal antibody 5D7A1. In certain embodiments, the level of change in the detectable fluorescence signal is elevated if it is significantly greater than the level of change in the detectable fluorescence signal from a negative control sample. In certain embodiments, the enrichment matrix further comprises a protease substrate-specific antibody or antigen binding fragment thereof that binds the protease substrate. In certain of these embodiments, the protease substrate-specific antibody or antigen binding fragment binds a protein or peptide component of the protease substrate. In other embodiments, the antibody or fragment thereof binds a fluorophyl component of the protease substrate (e.g., an anti-fluorescein antibody) or an acceptor component of the protease substrate (e.g., an anti-DABCYL antibody). In certain embodiments, the enrichment matrix is an immunosorbent support comprised of loose beads or a fixed column.

Provided herein in certain embodiments is a protease substrate comprising a donor fluorophore, an acceptor having an absorbance spectrum overlapping the emission spectrum of the donor fluorophore, and one or more *Aspergillus* protease cleavage sites. In certain of these embodiments, the protease substrate comprises one or more cleavage sites for Asp f2 or a homologue thereof. In certain embodiments, the protease substrate is a circular substrate. In certain embodiments, the protease substrate is a protein or peptide comprising the amino acid sequence of SEQ ID NO: 5, an elastin protein or peptide, or a collagen protein or peptide, and in certain embodiments the protease substrate is FluHSA2. In certain embodiments, the fluorophore is conjugated to a protein or peptide component of the protease substrate via a peptide bond at or near the N-terminus, and in certain embodiments the acceptor is conjugated to a protein or peptide component of the protease substrate via a peptide bond at or near the C-terminus. In certain of these embodiments, the acceptor is a dark quencher.

Provided herein in certain embodiments are kits for detecting an *Aspergillus* protease. In some embodiments, the detection kit may be an enrichment matrix comprised of one or more immunoaffinity beads to which at least one *Aspergillus* protease specific antibody is bound and at least one substrate, where a detectable fluorescent signal is produced upon interaction of the substrate with the *Aspergillus* protease.

Provided herein in certain embodiments are kits for detecting an *Aspergillus* protease in a sample comprising (a) an enrichment matrix comprising one or more immunoaffinity beads to which at least one *Aspergillus* protease-specific antibody or antigen binding fragment is bound and (b) at least one protease substrate, wherein a detectable fluorescent signal is produced upon interaction of the protease substrate with the *Aspergillus* protease. In certain embodiments, the *Aspergillus* protease is Asp f2 or a homologue thereof, and in certain of these embodiments the antibody or antigen binding fragment thereof specifically binds Asp f2 or a homologue thereof. In certain embodiments, the antibody or antigen binding fragment thereof comprises one or more CDRs selected from the group consisting of SEQ ID NOs: 8, 10, 12, 14, 16, and 18, and in certain embodiments the antibody or antigen binding fragments thereof comprises a variable heavy chain comprising the amino acid sequence of SEQ ID NO: 1 and/or a variable light chain comprising the amino acid sequence of SEQ ID NO: 2. In certain embodiments, the antibody is the monoclonal antibody 5D7A1. In certain embodiments, the protease substrate is a circular substrate. In certain embodiments, the protease substrate is a protein or peptide comprising the amino acid sequence of SEQ ID NO: 5, an elastin protein or peptide, or a collagen protein or peptide, and in certain embodiments the protease substrate is FluHSA2. In certain embodiments, the protease substrate comprises at least one fluorophore conjugated via a peptide bond at or near the N-terminus and at least one acceptor conjugated at or near the C-terminus. In certain of these embodiments, the acceptor is a dark quencher. Also provided herein is the use of the kits provided herein for detecting an *Aspergillus* protease in a sample.

Provided herein in certain embodiments are antibodies and antigen binding fragments thereof that specifically bind an *Aspergillus* protease. In certain of these embodiments, the *Aspergillus* protease is Asp f2 or a homologue thereof, and in certain embodiments the Asp f2 or homologue thereof is glycosylated. In certain embodiments, the antibody or antigen binding fragment thereof comprises one or more CDRs selected from the group consisting of SEQ ID NOs: 8, 10, 12, 14, 16, and 18, and in certain embodiments the antibody or antigen binding fragments thereof comprises a variable heavy chain comprising the amino acid sequence of SEQ ID NO: 1 and/or a variable light chain comprising the amino acid sequence of SEQ ID NO: 2. In certain embodiments, the antibody is the monoclonal antibody 5D7A1. In certain embodiments, the antibody is a monoclonal antibody, a chimeric antibody, a humanized antibody, an affinity matured antibody, a human antibody, or a bispecific antibody. Also provided herein are compositions and formulations that comprise the antibodies and antigen binding fragments disclosed herein, as well as the use of these antibodies and fragments thereof, compositions, and formulations in methods and kits for detecting an *Aspergillus* protease in a sample.

BRIEF DESCRIPTION OF THE DRAWINGS

FIG. 2 shows the amino acid sequences of the VH chain (SEQ ID NO: 1) and VL chain (SEQ ID NO: 2) of the monoclonal antibody 5D7A1.

FIG. 3 shows DNA sequences encoding the VH chain (SEQ ID NO: 3) and VL chain (SEQ ID NO: 4) of the monoclonal antibody 5D7A1.

FIG. 4 shows the amino acid sequence of the FluHSA2 peptide (SEQ ID NO: 5). The sequence contains a fluorophore and a quencher. The 5-carboxyfluorescein (5-Fam) fluorophore is conjugated to the epsilon-amino group of threonine at the N-terminus and the 4-((4-(dimethylamino) phenyl)azo)benzoic acid (DABCYL) quencher is conjugated to the epsilon amino group of the lysine side chain at the C-terminus of the peptide.

FIG. 6 illustrates the bead-based Asp f2 activity measured in bronchoalveolar lavage fluid (BALF) samples from City of Hope patients with either probable or proven aspergillosis, other mold infections, or no infection. The level of significance between patients with probable or proven aspergillosis and those that had other mold infections or were negative was $p<0.0001$. Statistical evaluation was performed by ANOVA. ****=significant, ns=non-significant.

FIG. 7 shows the amino acid sequence alignment of Asp f2 from *A. fumigatus* (gi|8300352) (SEQ ID NO: 27, marked with squares) and the deuterolysin from *Aspergillus oryzae* RIB340 (gi|94730401) (SEQ ID NO: 26, marked with circles). Identity between the sequences is 24% and homology is 35%.

FIG. 8 shows the amino acid sequence alignment of the Asp f2 from *A. fumigatus* (gi|83300352) (SEQ ID NO:29, marked with squares) and putative metalloprotease MEP20 from *A. fumigatus* (gi|780794) (SEQ ID NO:28, marked with circles). Identity between the sequences is 25% and homology is 39%.

FIG. 12 shows the full length amino acid sequence (1-310) of recombinant Asp f2 (SEQ ID NO: 30) and the analysis of Asp f2 histidines. Histidines H138, H186, H190, and H201 were mutated to alanine. H186 and H190 are located in the HRLYH motif.

Figure 15:
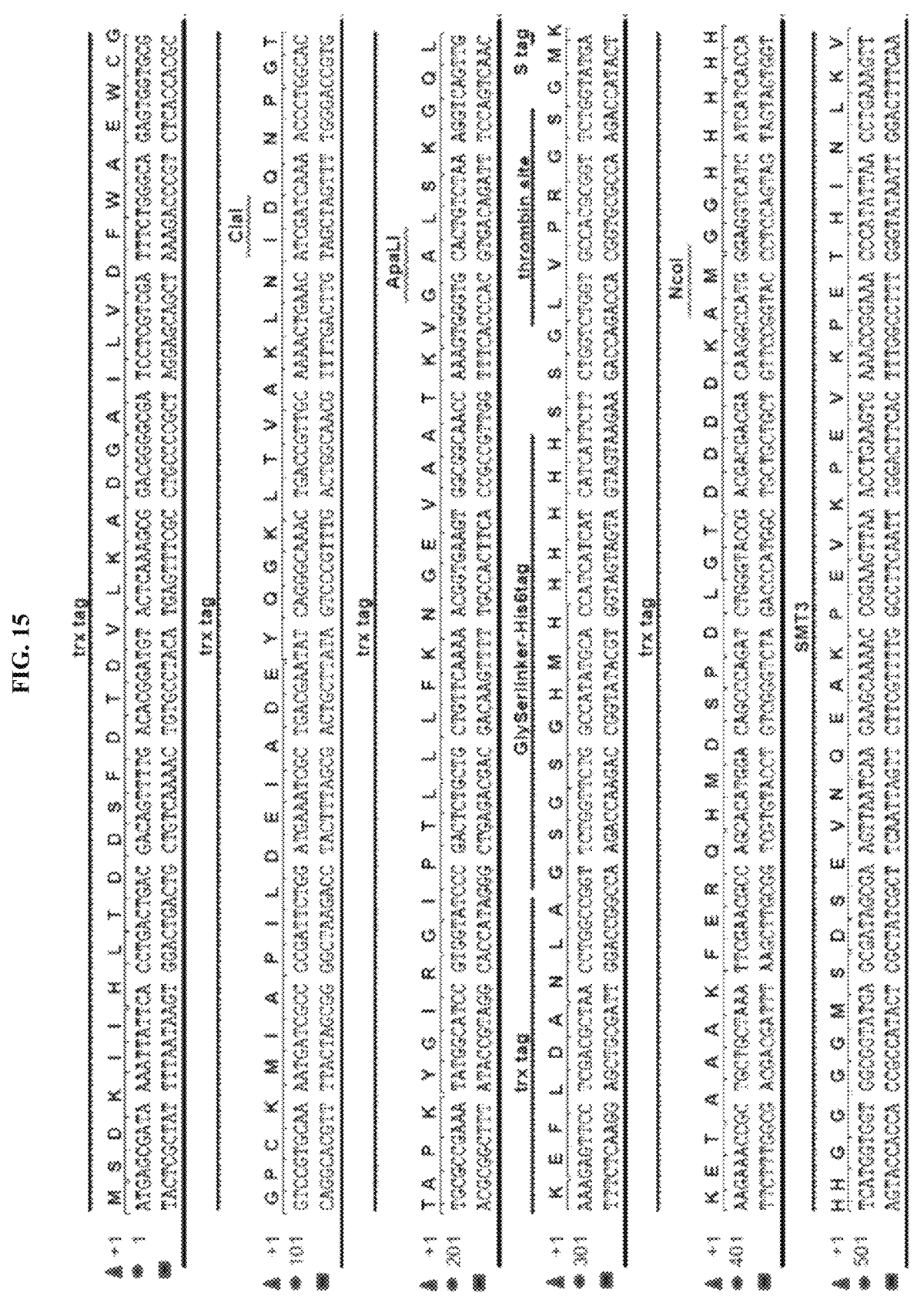
Figure 15:
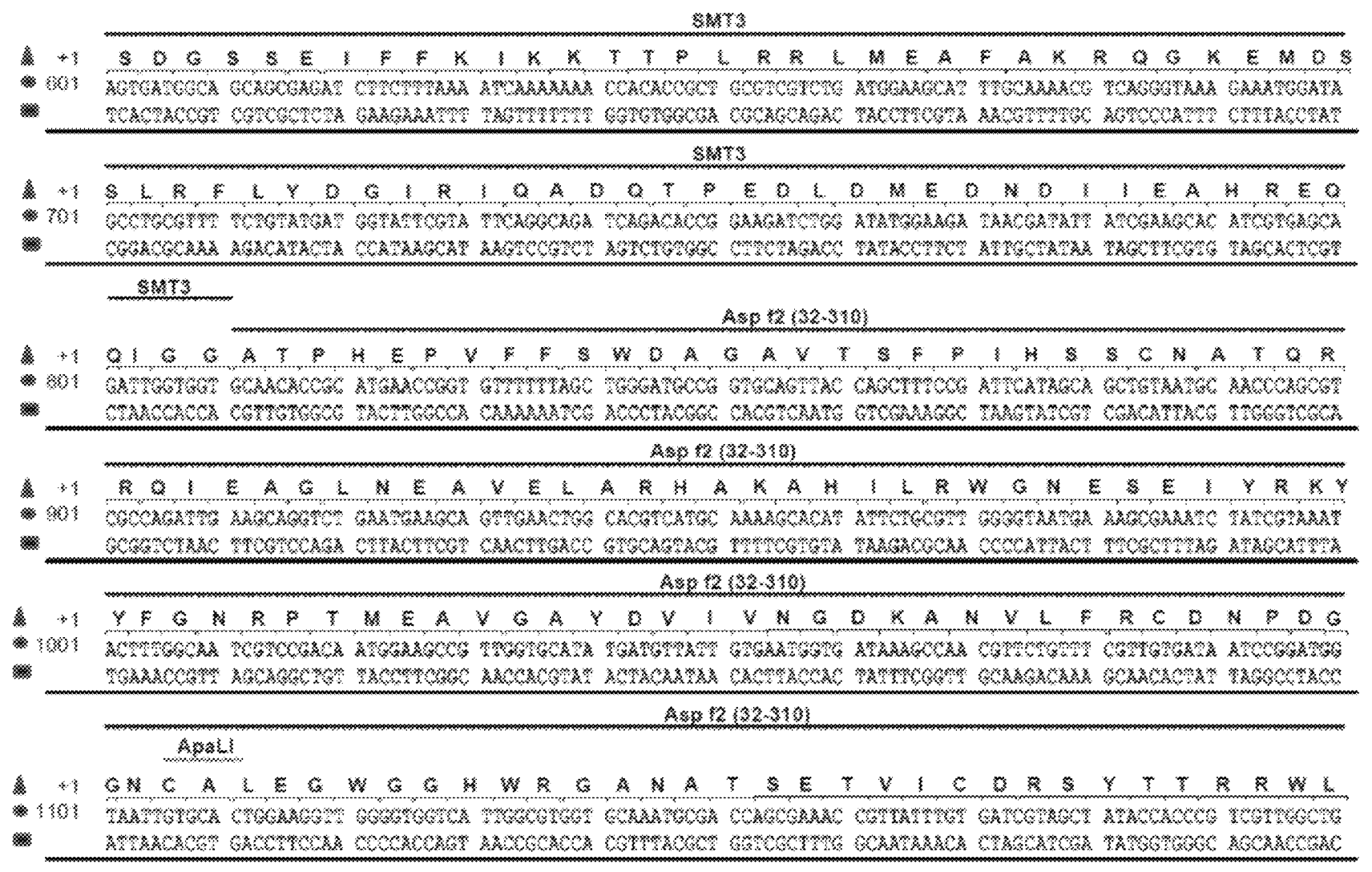
Figure 15:
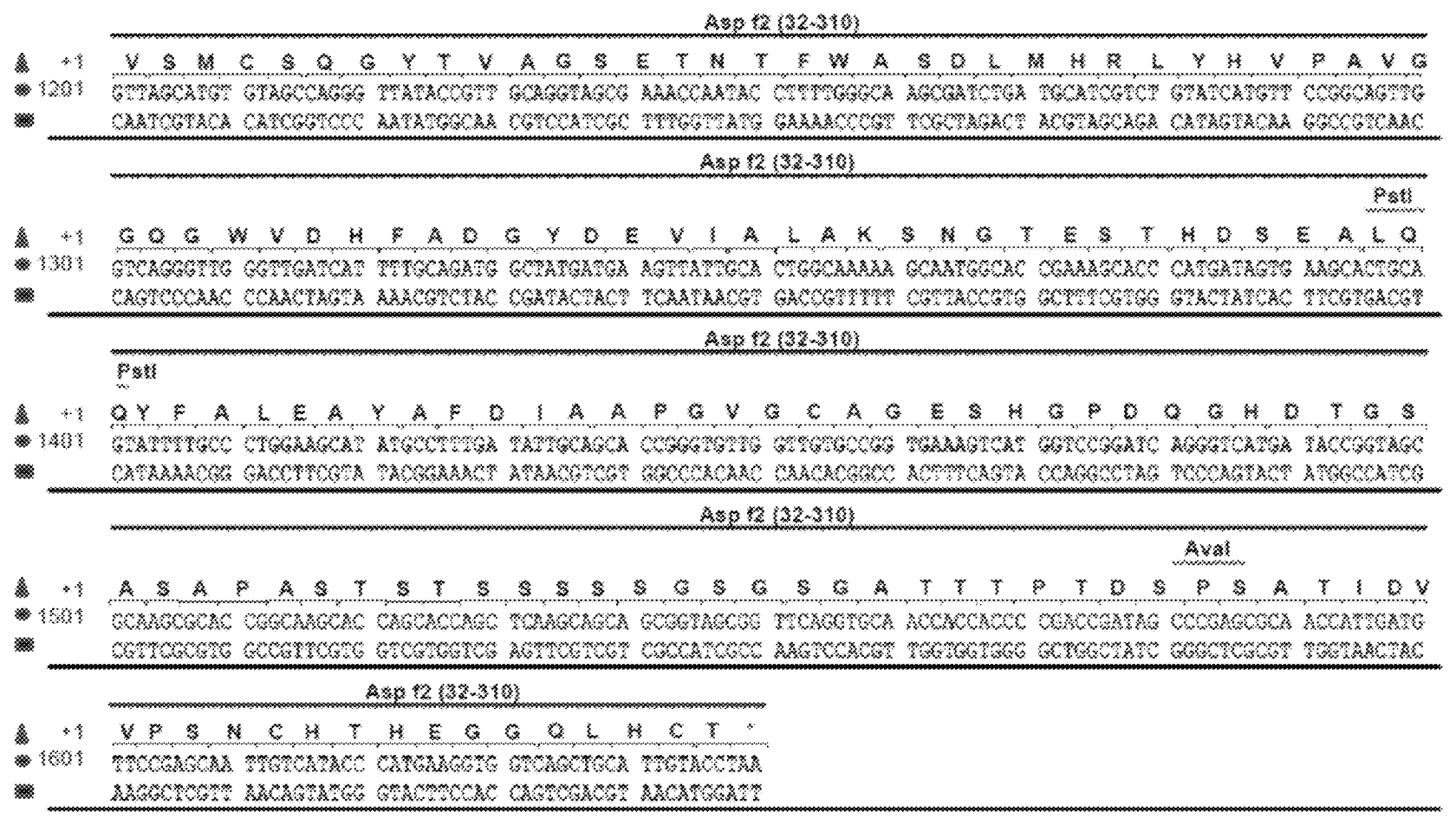

FIG. 15 shows the amino acid and DNA sequence (5'-3' and 3'-5 of the fusion protein construct, Trx-SMT3-Asp f2 [aa 32-310]. The amino acid sequence of Trx-SMT3-Asp f2 is marked with triangles (SEQ ID NO: 6). The 5'-3' DNA sequence of Trx-SMT3-Asp f2 is marked with circles (SEQ ID NO: 7) and the 3'-5' complementary sequence strand is marked with squares (SEQ ID NO: 31). Note that although the figure shows the 3'-5' complementary DNA strand (see squares), SEQ ID NO: 31 in the sequence listing represents the reverse (i.e., 5'-3') complement of SEQ ID NO: 7.

FIG. 16 shows the amino acid sequence and the DNA sequence of the fusion protein construct, Trx-SMT3-Asp f2 [aa 32-310] (SEQ ID NOS: 6 and 7, respectively).

FIG. 22 shows the amino acid and DNA sequences of the variable heavy (VH) and variable light (VL) complementarity determining region (CDR) 1 regions of the monoclonal antibody, 5D7A1: VH CDR1 amino acid sequence (SEQ ID NO: 8); VH CDR1 DNA sequence (SEQ ID NO: 9); VL CDR1 amino acid sequence (SEQ ID NO: 10); and VL CDR1 DNA sequence (SEQ ID NO: 11).

FIG. 23 shows the amino acid and DNA sequences of the VH and VL CDR2 regions of the monoclonal antibody, 5D7A1: VH CDR2 amino acid sequence (SEQ ID NO: 12); VH CDR2 DNA sequence (SEQ ID NO: 13); VL CDR2 amino acid sequence (SEQ ID NO: 14); and VL CDR2 DNA sequence (SEQ ID NO: 15).

FIG. 24 shows the amino acid and DNA sequences of the VH and VL CDR3 regions of the monoclonal antibody, 5D7A1: VH CDR3 amino acid sequence (SEQ ID NO: 16); VH CDR3 DNA sequence (SEQ ID NO: 17); VL CDR3 amino acid sequence (SEQ ID NO: 18); and VL CDR3 DNA sequence (SEQ ID NO: 19).

FIG. 28 shows the amino acid of the $V_L$-GS15-$V_H$-Fc scFv and the DNA sequence of the scFv in the pEE12.4 vector.

FIG. 30 shows the amino acid of the $V_H$-GS15-$V_L$-Fc scFv and the DNA sequence of the scFv in the pEE12.4 vector.

DETAILED DESCRIPTION

Figure 1:
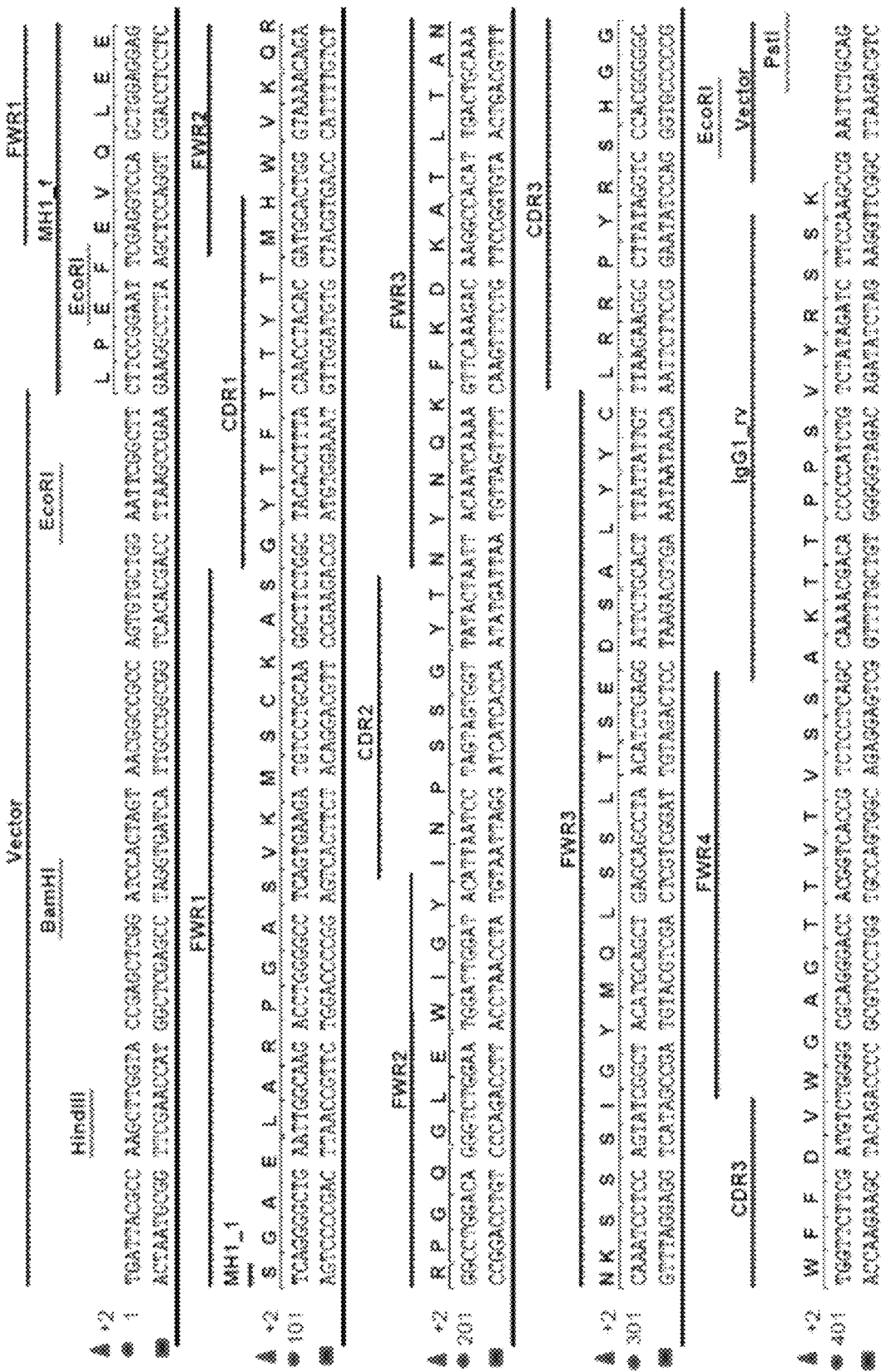
FIG. 1 shows the amino acid sequence and 5'-3' and 3'-5' DNA sequences of the variable heavy (VH) and variable light (VL) chains of the Asp f2-specific monoclonal antibody 5D7A1 that binds the native, glycosylated form of *A. fumigatus* Asp f2. The amino acid sequence of the variable heavy chain of 5D7A1 is marked with triangles (SEQ ID NO: 1) and the amino acid sequence of the variable light chain of 5D7A1 is marked with stars (SEQ ID NO: 2). The 5'-3' DNA sequence of 5D7A1 and surrounding vector region is marked with circles (SEQ ID NO: 24) and the 3'-5' complementary DNA strand is marked with squares (SEQ ID NO: 25). Note that although the figure shows the 3'-5' complementary DNA strand (see squares), SEQ ID NO: 25 in the sequence listing represents the reverse (i.e., 5'-3') complement of SEQ ID NO: 24. The DNA sequence was confirmed by mass spectrometric analysis of trypsin and chymotrypsin-derived peptides of the monoclonal antibody.

As disclosed herein, the *Aspergillus* allergen Asp f2 has unexpectedly been found to possess zinc metalloprotease activity. Based on this finding, a novel activity-based method is provided herein for detecting *Aspergillus* proteases in a sample by contacting the sample with a protease substrate comprising one or more protease cleavage sites. Cleavage of the substrate indicates the presence of *Aspergillus* protease in the sample. In certain embodiments, this method can be used to diagnose a subject with aspergillosis caused by an *Aspergillus* infection by detecting the presence of a *Aspergillus* proteases in a biological sample from the subject. In other embodiments, this detection method can be incorporated into a method of treating aspergillosis caused by an *Aspergillus* infection. For example, detection of the presence of an *Aspergillus* protease in a biological sample from a subject can be used to determine whether to administer or re-administer a therapeutic agent, or to help determine an effective dosage for administering such an agent. Also provided herein are kits for carrying out the detection, diagnosis, and treatment methods disclosed herein. The methods and kits provided herein are superior to previously developed methods, in part because they provide equal or greater sensitivity with reduced time and cost. The methods disclosed herein may be performed in either a manual or automated format.

In certain embodiments, the methods and kits provided herein may be used to detect the presence of *Aspergillus* protease Asp f2. In other embodiments, the methods and kits provided herein may be used to detect the presence of other *Aspergillus* proteases, including but not limited to *Aspergillus* proteases comprising the amino acid motifs HRLYH (SEQ ID NO: 36) or HEXXH (SEQ ID NO: 37), or an amino acid sequence with significant sequence identity to these motifs. In certain of these embodiments, an amino acid sequence with significant sequence identity to these motifs comprises one or more conservative substitutions versus the motif.

In certain embodiments, the methods and kits provided herein may be used to detect an *Aspergillus* protease from *Aspergillus fumigatus*, including but not limited to Asp f2. In other embodiments, the methods and kits may be used to detect *Aspergillus* proteases such as Asp f2 or homologues thereof from other *Aspergillus* species, including for example *A. nidulans, A. versicolor, A. niger*, and *A. terreus*. Accordingly, the methods and kits disclosed herein may be used to diagnose a subject with aspergillosis caused by infection with *A. fumigatus, A. nidulans, A. versicolor, A. niger*, or *A. terreus*, or to treat aspergillosis caused by infection with *A. fumigatus, A. nidulans, A. versicolor, A. niger*, or *A. terreus*. In certain embodiments, the *Aspergillus* protease being detected is glycosylated at one or more locations within the protein. For example, in certain embodiments the methods and kits provided herein detect glycosylated Asp f2.

In certain embodiments of the methods and kits provided herein, a sample is enriched for an *Aspergillus* protease prior to or at the same time as contact with the protease substrate. In certain of these embodiments, enrichment is achieved by contacting the sample with one or more protease-specific antibodies or antigen binding fragments thereof. For example, where the *Aspergillus* protease is Asp f2, the sample may be contacted with one or more Asp f2-specific antibodies or antigen binding fragments thereof. In these embodiments, the antibodies or antigen binding fragments thereof may be monoclonal antibodies, chimeric antibodies, humanized antibodies, affinity matured antibodies, human antibodies, bispecific antibodies, or any antigen binding fragment thereof such as an scFv, F(ab')2, Fab, Fab' or Fv. In certain embodiments, the *Aspergillus* protease-specific antibody or antigen binding fragment thereof binds the *Aspergillus* protease in such a way such that the protease retains its catalytic activity after binding.

Provided herein in certain embodiments are *Aspergillus* protease-specific antibodies or antigen binding fragments thereof, as well as compositions, formulations, and kits comprising these antibodies or antigen binding fragments thereof and the use of these antibodies or antigen binding fragments thereof in the detection, diagnosis, and treatment methods disclosed herein. As discussed in the Examples below, the novel monoclonal antibody 5D7A1 was used to bind Asp f2 in a bead-based assay. Accordingly, in certain embodiments compositions, formulations, and kits are provided that comprise 5D7A1 alone or in combination with other components. In certain embodiments, the antibodies or antigen binding fragments thereof provided herein comprise the complete variable light or variable heavy chain of 5D7A1 or homologues thereof. In these embodiments, the antibodies or antigen binding fragments thereof comprise a light chain comprising the amino acid sequence of SEQ ID NO: 2, a heavy chain comprising the amino acid sequence of SEQ ID NO: 1, or a combination thereof. In other embodiments, the antibodies or antigen binding fragments thereof provided herein comprise a portion of the variable light or variable heavy chain of 5D7A1. In certain of these embodiments, the antibodies or antigen binding fragments thereof comprise one or more CDRs selected from the group consisting of SEQ ID NOs: 8, 10, 12, 14, 16, and 18 (FIGS. 22-24), or any combination thereof. In certain embodiments, an antigen binding fragment thereof as provided herein is an scFv, and in certain of these embodiments the scFv comprises the amino acid sequence of SEQ ID NO: 20 or 22 or one or more CDRs set forth therein (FIGS. 28, 30).

In certain embodiments where a sample is enriched for an *Aspergillus* protease using an *Aspergillus* protease-specific antibody or antigen binding fragment thereof, the antibody or antigen binding fragment thereof may be free in solution. In these embodiments, the *Aspergillus* protease-antibody conjugate resulting from binding may be removed from solution for testing with a protease substrate using methods well known in the art. In other embodiments, the antibody or antigen binding fragment thereof may be attached to or immobilized on an enrichment matrix such as an immunosorbent support of loose beads or a fixed column. In these embodiments, the enrichment matrix may comprise immunoaffinity beads including cyanogen-bromide (CNBr) activated Sepharose beads, protein-A, protein-G, or protein A/G conjugated Sepharose, agarose, or magnetic beads coupled and cross-linked to *Aspergillus* protease-specific antibodies or antigen binding fragments thereof.

In those embodiments of the methods and kits disclosed herein that utilize an enrichment matrix, formation of the *Aspergillus* protease-antibody conjugate results in the *Aspergillus* protease being attached to or immobilized on the enrichment matrix. For example, where a sample is being tested for the presence of Asp f2, the sample may be contacted with an enrichment matrix comprising one or more Asp f2-specific antibodies that bind Asp f2 to form an Asp f2-antibody conjugate. During or after formation of the *Aspergillus* protease-antibody conjugate, the enrichment matrix is contacted with the protease substrate. In certain embodiments, the enrichment matrix may comprise the protease substrate prior to addition of the sample. In other embodiments, the protease substrate may be added to the enrichment matrix after sample addition. In certain of these embodiments, the enrichment matrix may be washed prior to contact with the protease substrate in order to remove unbound *Aspergillus* protease and/or other proteins and molecules. If the *Aspergillus* protease is present in the enrichment matrix, the protease substrate will be cleaved upon contact with the enrichment matrix.

In certain embodiments of the methods disclosed herein, exposure of a sample to an enrichment matrix and to a protease substrate occurs under conditions permitting binding of *Aspergillus* protease to an antibody or antigen binding fragment thereof on the enrichment matrix and modification of the protease substrate by the *Aspergillus* protease. In certain embodiments, one or more of these steps may be carried out in the dark.

A protease substrate for use in the methods and kits disclosed herein can be any chemical, biochemical, or biological species or compound that reacts with or is capable of being modified by an *Aspergillus* protease. In certain embodiments, the protease substrate comprises one or more *Aspergillus* protease cleavage sites, and in certain of these embodiments the protease substrate may comprise one, two, three, four, or five or more cleavage sites. For example, where the *Aspergillus* protease is Asp f, the protease substrate comprises one or more Asp f2 cleavage sites. In certain of these embodiments, the Asp f2 cleavage site comprises the amino acid sequence FSALK (SEQ ID NO: 38). As disclosed in the Examples below, Asp f2 is a protease that cleaves and/or degrades certain protein or peptide substrates, including the peptide of SEQ ID NO:5, collagen, and elastin. In certain embodiments of the methods and kits provided herein wherein the *Aspergillus* protease is Asp f, the Asp f2 protease substrate is a peptide comprising the amino acid sequence FSALK (SEQ ID NO: 38), the amino acid sequence of SEQ ID NO: 5, a human serum albumin protein or portion thereof (e.g., a peptide), an elastin protein or portion thereof (e.g., a peptide), or a collagen protein or portion thereof (e.g., a peptide). In certain embodiments, the protease substrate is a circular substrate, which can increase the stability of the peptide by enhancing protection against digestion by other proteases. In certain of these embodiments, the circular substrate is formed through a disulfide bond between two cysteines located within the peptide. In other embodiments, the substrate may be circularized through amino acids other than cysteines. For example, a glutamic acid residue may be positioned at a location 5' of the protease cleavage site, and the peptide may be circularized via an N-terminus to glutamate side chain peptide bond. In other embodiments, the protease substrate is non-circular.

Cleavage or other modification of a protease substrate may be detected in a variety of ways well known in the art. For example, the protease substrate may be removed from solution or from an enrichment matrix and run on a gel to detect changes in size. In other embodiments, the protease substrate may be capable of eliciting a detectable fluorescent signal when modified by an *Aspergillus* protease. In these embodiments, cleavage may be detected based on this fluorescent signal. For example, in certain embodiments the protease substrate may comprise a donor fluorophore such as 5-carboxyfluorescein (5-Fam) or 4-methylumbelliferone (4-Mu) and an acceptor having an absorbance spectrum overlapping the emission spectrum of the donor fluorophore, including for example a dark quencher such as 4-(dimethylaminoazo)benzene-4-carboxy (DABCYL). In certain embodiments, the one or more fluorophores may be conjugated to the peptide or protein component of the protease substrate at or near the N-terminus of the peptide or protein. As used herein, "near the N-terminus" refers to any position on the peptide or protein component of the protease substrate that is within five amino acids of the N-terminus of the peptide or protein, while "near the C-terminus" refers to any position on the peptide or protein component of the protease substrate that is within five amino acids of the C-terminus of the peptide or protein. In certain of these embodiments, the fluorophore (e.g., 5-FAM) is conjugated to an alpha-amino group of an N-terminal amino acid, and in certain of these embodiments the N-terminal amino acid is a threonine residue. In other embodiments, the fluorophore may be conjugated to an epsilon-amino group of an N-terminal amino acid. Similarly, in certain embodiments the acceptor may be conjugated to the peptide or protein component at or near the C-terminus of the peptide or protein. In certain of these embodiments, the acceptor (e.g., DABCYL) is conjugated to an epsilon-amino group of a C-terminal amino acid, and in certain of these embodiments the C-terminal amino acid is a lysine residue.

In those embodiments where the fluorophore and/or acceptor are conjugated to the peptide or protein component of the protease substrate, conjugation may be via a peptide bond, which enhances the stability of the substrate. In certain embodiments wherein a protease substrate comprises a fluorophore and an acceptor, the acceptor (e.g., DABCYL) suppresses the fluorescence emission of the fluorophore when the protease substrate is intact and the acceptor and fluorophore remain close together. When the substrate is cleaved by the *Aspergillus* protease, the fluorophore and acceptor are separated and the fluorophore emits light energy upon excitation. Thus, protease substrate cleavage (and hence the presence of *Aspergillus* protease) is detected by contacting the protease substrate with an excitatory wavelength of light. If the protease substrate is cleaved (i.e., if the *Aspergillus* protease is present), the fluorophore will emit fluorescence upon excitation. If the protease substrate remains intact, the acceptor will suppress fluorescent emission. The protease substrate may be contacted with the excitatory wavelength in solution, on an enrichment matrix, or after removal or elution from an enrichment matrix. In certain embodiments, the protease substrate is part of a substrate composition comprising the protease substrate plus one or more additional components.

Detection of a fluorescent signal in conjunction with the methods disclosed herein may be performed using a handheld ultraviolet (UV) light, a fluorescence excitation and/or detecting tool, or any suitable commercially available fluorometer. In some embodiments, a Victor X2 multilabel plate reader (Perkin Elmer, Shelton, Conn.) may be used to detect fluorescence. In some embodiments, the level of the change in the detectable fluorescence signal is calculated as a change in relative fluorescence unit (RFU). In certain embodiments, the level of the change in the fluorescence signal may be classified as elevated (i.e., *Aspergillus* protease is present) when the level of the change in the signal is greater than or equal to a predetermined level of background fluorescence. In some embodiments, the predetermined level of background fluorescence may be the fluorescent level of an *Aspergillus* protease-free control sample. In some embodiments, the level of the change in the detectable fluorescence signal is elevated when the level is significantly greater than the level of change in detectable fluorescence signal from a negative control sample. As described herein, a "negative control" sample comprises a sample that does not comprise *Aspergillus* protease, for example a biological sample from a subject that is known to not be infected with *Aspergillus*. In other embodiments, the negative control sample may be treated with a metalloprotease inhibitor.

In certain embodiments, an enrichment matrix may comprise beads coupled and cross-linked to antibodies or antigen binding fragments thereof that bind a fluorophore and/or acceptor conjugated to the *Aspergillus* protease substrate. For example, cyanogen-bromide (CNBr)-activated Sepharose beads may be coupled and cross linked to anti-FITC antibodies that bind a fluorescent 5-Fam label conjugated to the *Aspergillus* protease substrate. In another example, the enrichment matrix comprises CNBr-activated Sepharose beads coupled and cross-linked to anti-DABCYL antibodies or antigen binding fragments thereof that bind DABCYL conjugated to the *Aspergillus* protease substrate. In certain embodiments, the enrichment matrix may further comprise anti-protease substrate specific antibodies or antigen binding fragments thereof. In certain embodiments, the anti-protease substrate specific antibodies or antigen binding fragments thereof may bind a portion of the protease substrate including a fluorophore or acceptor or amino acids of the peptide or protein component of the substrate sequence.

In certain embodiments, the enrichment matrix may comprise a double affinity matrix comprising beads coupled and cross-linked to antibodies or antigen binding fragments thereof that specifically bind the *Aspergillus* protease as described herein and beads coupled and cross-linked to antibodies or antigen binding fragments thereof that specifically bind the *Aspergillus* protease substrate or fluorophore and/or acceptors conjugated to the *Aspergillus* protease substrate as described herein.

In certain embodiments wherein the *Aspergillus* protease being detected is Asp f2, the protease substrate may consist of or comprise FluHSA2 (see Example 1 below). In these embodiments, the FluHSA2 protease substrate may be circular or non-circular. In certain of these embodiments, the methods and kits and utilize an enrichment matrix comprising CNBr-activated Sepharose beads coupled and cross linked to antibodies or antigen binding fragments thereof that bind a portion of FluHSA2.

In certain embodiments of the diagnosis and treatment methods provided herein, the methods are used to determine if a subject is currently suffering from aspergillosis caused by an *Aspergillus* infection. In other embodiments, the methods may be used to determine whether a subject has suffered from aspergillosis previously, or to predict whether a subject is likely to develop aspergillosis. In certain embodiments, a subject is suspected of suffering from aspergillosis due to the presence of one or more symptoms associated with aspergillosis. In certain embodiments, a subject has been previously diagnosed with aspergillosis.

In certain embodiments of the treatment methods provided herein, the steps of detecting *Aspergillus* protease are repeated at various timepoints following administration of a therapeutic agent or an increased dosage of a therapeutic agent. In this manner, the diagnostic methods disclosed herein can be used to monitor the efficacy of the therapeutic agent and/or to make adjustments to dosage. In certain embodiments, the steps of detecting *Aspergillus* protease are repeated at specific intervals until a specific therapeutic endpoint is reached, and in certain embodiments this therapeutic endpoint is the absence of detectable *Aspergillus* protease in a biological sample from the subject.

In certain embodiments of the methods and kits disclosed herein, a sample to be evaluated for the presence of Asp f2 is a biological sample, including but not limited to BALF, blood, serum, urine, saliva, or any other suitable biological sample that may contain Asp f2 in the presence of aspergillosis.

In certain embodiments of the kits provided herein, the kits comprise a protease substrate and instructions for carrying out the methods disclosed herein. In certain embodiments, the kits further comprise one or more *Aspergillus* protease-specific antibodies or antigen binding fragments thereof, and in certain of these embodiments the *Aspergillus* protease-specific antibodies or antigen binding fragments thereof are Asp f2-specific antibodies or antigen binding fragments thereof as disclosed herein. In certain embodiments, the kits comprise one or more *Aspergillus* protease substrate-specific antibodies or antigen binding fragments thereof, and in certain of these embodiments the *Aspergillus* protease substrate-specific antibodies or antigen binding fragments thereof are Asp f2-substrate specific antibodies or antigen binding fragments thereof as disclosed herein. In certain embodiments, the kits comprise a double affinity matrix as described herein. In certain embodiments, the kits comprise an enrichment matrix and instructions for use thereof. In certain of these embodiments, the enrichment matrix may be pre-loaded onto a solid column.

An example of an embodiment using an enrichment matrix is set forth in Example 1 below. 125 bronchoalveolar lavage fluid (BALF) samples from patients suspected of having an aspergillosis infection or another form of pulmonary mycosis were tested for the presence of Asp f2 using a bead-based assay. The Asp f2 antibody 5D7A1 was immobilized on beads, then contacted with the BALF samples. The presence of immobilized Asp f2-antibody complex on the beads was detected by contacting the beads with the novel fluorogenic peptide FluHSA2. The results of this experiment demonstrated that Asp f2 detection using the bead-based assay correlated with the clinical diagnosis of invasive aspergillosis, and confirmed that the presently disclosed methods are robust, inexpensive, and can be executed in a short timeframe (e.g., a few hours or less).

Provided herein in certain embodiments are detection and diagnosis methods that utilize the bead-based assay set forth in Example 1 or variations thereof (for example, using different fluorophores or protease substrates), as well as kits for carrying out such methods. In certain embodiments, these methods comprise obtaining a sample suspected of containing Asp f2 (e.g., a biological sample from a subject suspected of having aspergillosis due to *Aspergillus* infection), contacting the sample with an enrichment matrix comprising 5D7A1 or an Asp f2-binding fragment thereof immobilized on beads, contacting the enrichment matrix with the protease substrate such as FluHSA2, and measuring fluorescence at Excitation (Ex) 485 nm/Emission (Em) 535 nm. Also provided herein are treatment methods further comprising administering one or more aspergillosis therapeutic agents, or an increased dosage of a previously administered therapeutic agent, to a subject determined to have aspergillosis due to *Aspergillus* infection. In certain of these embodiments, the therapeutic agent may be selected from one or more antifungal medicines including, but not limited to, voriconazole, amphotericin B, echinocandins, and/or itraconazole, or immunosuppressive drugs. In other embodiments, the subject may be treated by undergoing surgery.

In certain embodiments of the kits provided herein, the kits comprise one or more components of the bead-based assay described in Example 1. In certain of these embodiments, the kits comprise an enrichment matrix comprised of one or more immunoaffinity beads to which at least one *Aspergillus* protease-specific antibody or antigen binding fragment thereof is bound and at least one protease substrate, wherein after interaction of the protease substrate with an *Aspergillus* protease a detectable fluorescent signal is produced. In certain embodiments, the immunoaffinity beads comprising *Aspergillus* protease-specific antibody may be lyophilized (freeze-dried) to allow for storage at 4° C. for several months without loss of binding affinity. These ready-made beads reduce the time necessary to execute the assay provided by the kit. In some embodiments, the immunoaffinity beads may be lyophilized in the presence of 0.1 M ammonium bicarbonate buffer. In certain embodiments, the kit may include a control substrate that cannot be cleaved by the *Aspergillus* protease. In some embodiments, the kit may include an inhibitor of metalloprotease activity (e.g., the Zn metalloprotease inhibitor TPEN) as a control. In certain embodiments, the kit may include a positive control. For example, the kit may include a recombinant Asp f2 protein that may be used to test cleavage of the *Aspergillus* protease substrate provided in the kit. In certain embodiments, the Asp f2 protein may be glycosylated. In certain embodiments, the recombinant Asp f2 protein may be in an inactive form. In certain embodiments, the recombinant Asp f2 protein may comprise a fusion protein that may be activated after cleavage of an inactivating linker. For example, in certain embodiments, the Asp f2 protein may comprise SEQ ID NO: 6 as discussed in Example 2 or fragments or homologous proteins thereof. In certain of these embodiments, the inactive recombinant Asp f2 protein may be activated by cleaving the thioredoxin (Trx)-SMT3 N-terminal linker using ubiquitin-like specific protease (ULP1). In other embodiments, other enzymes may be used to cleave the inactivating linker such as thrombin or enterokinase. In certain embodiments, the kit may include recombinant Asp f2 protein in an active form. In certain embodiments, the recombinant Asp f2 protein used as a positive control in the kit comprises residues 32-310 of Asp f2 (see FIG. 12) or fragments or homologous proteins thereof.

According to some embodiments, the methods or kits provided herein may be used in a manual or automated format. In certain embodiments, the methods or kits may be used as a high-throughput detection system. In some embodiments, the methods or kits may be used as a high-throughput detection system for inhibitors of *Aspergillus* protease enzymatic activity. Such high-throughput detection systems are preferably automated for large-scale detection and testing, such as may be used in a diagnostic medical laboratory or in a manufacturing facility.

As used herein, a "subject" refers to a human or animal, including all mammals such as primates (particularly higher primates), sheep, dogs, rodents (e.g., mouse or rat), birds, guinea pigs, goats, pigs, cats, rabbits, and cows. In one embodiment, the subject is a penguin. In some embodiments, the subject is a human. In some embodiments, the subject is a patient.

As used herein the term "homologous" is used to refer to any amino acid or nucleotide sequence that displays at least 90% similarity with an amino acid or nucleotide sequence wherein the resulting protein still retains its desired functional properties.

As used herein, the term "significantly" or "significant" refers to a result that is statistically significant. In certain embodiments, statistical significance may be determined using any known test used to determine statistical significance. For example, a paired Student's t-test may be used to determine statistical significance. As described herein, a calculated p-value with a threshold of $p<0.05$ is considered statistically significant. In some embodiments, a calculated p-value with a threshold of $p<0.0001$ is considered statistically significant. In other embodiments, the term "significantly" or "significant" may be used to refer to a relative comparison between two or more experimental groups that are of interest. For example, if the results (i.e., change in detectable fluorescence signal or other measurable result) obtained from two experimental groups are found to be different by a factor of more than one, then this difference may be referred to as significant. In some embodiments, two or more groups may be significantly different if their experimental results are different by a factor of 2, 3, 4, 5, 6, 7, 8, 9, 10, or greater than 10.

The following examples are intended to illustrate various embodiments of the disclosure. As such, the specific embodiments discussed are not to be construed as limitations on the scope of the invention. It will be apparent to one skilled in the art that various equivalents, changes, and modifications may be made without departing from the scope of the disclosure, and it is understood that such equivalent embodiments are to be included herein. Further, all references cited in the disclosure are hereby incorporated by reference in their entirety, as if fully set forth herein.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLES

Example 1: Detection of Proteolytic Activity of Asp f2 in Bronchoalveolar Lavage Fluid A novel bead-based assay was developed for detecting Asp f2 proteolytic activity. An immobilization bead-based immuno-affinity matrix was prepared using the novel anti-Asp f2 monoclonal antibody 5D7A1 (FIGS. 1-3, SEQ ID NOS: 1-4). As demonstrated below, 5D7A1 binds the native, glycosylated form of Asp f2. Cyanogen bromide (CNBr)-activated sepharose beads were swelled in ice-cold HCl (1 mM). Beads (1.0 g) were incubated with 3.0 mg of 5D7A1 in Coupling Buffer (NaHCO$_3$, 0.1 M and NaCl, 0.5 M, pH 8.3-8.5) and rotated for two hours at 22° C. or for 16 hours at 4° C. Beads were blocked with 0.1 M ethanolamine, pH 8.0, then washed with buffers of alternating pH (first with Coupling Buffer, pH 8.5, then with a low pH buffer (sodium acetate, 0.1 M, NaCl, 0.5 M, pH 4.0)). These dual washes were repeated four times. Lastly, beads were resuspended in ammonium bicarbonate (100 mM), lyophilized and stored at 4° C.

125 bronchoalveolar lavage fluid (BALF) samples from patients at City of Hope suspected of having an aspergillosis infection or another form of pulmonary mycosis were lyophilized to dryness and then re-dissolved in water in one tenth of the original BALF volume. Re-dissolved BALF (0.5 mL) was combined with 0.5 mL of Immunoprecipitation (IP) Binding Buffer (Tris base, 0.025 M, NaCl, 0.15M, NP-40, 1%, glycerol, 5%; pH 7.4). To immunoenrich active Asp f 2, antibody-coupled beads (200 µL) were transferred into each tube of BALF/IP Binding Buffer or BALF-negative controls (0.9% NaCl:IP Binding Buffer, 1:1). Samples were rotated for 1 hour at 22° C. followed by 16 hours rotation at 4° C. The beads were washed twice with IP Binding buffer, three times with TBS (Tris base, 25 mM, NaCl, 150 mM, pH 7.2), once with NaCl (0.2 M), and finally three times with protease-free H2O. Beads were re-dissolved in H$_2$O (2×100 µL for duplicate or 3×100 µL for triplicate measurements).

Figure 5:
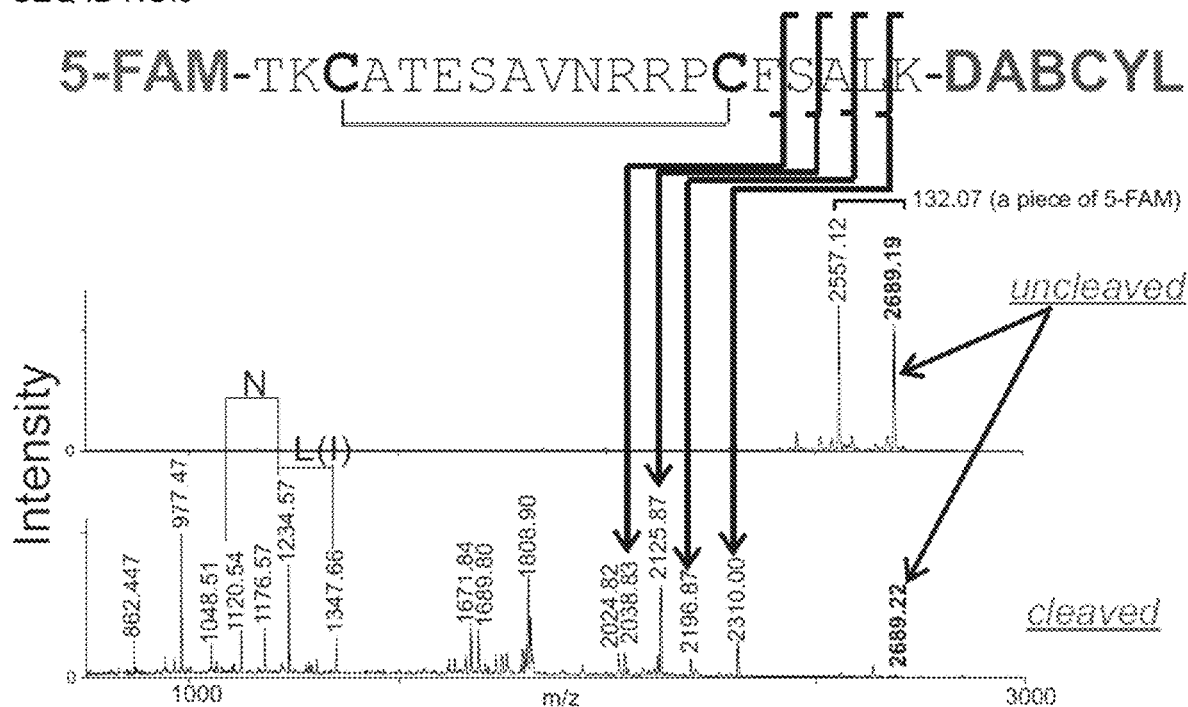
FIG. 5 illustrates the mass spectrometric analysis (MALDI spectra) and primary structure of the FluHSA2 substrate (SEQ ID NO: 5) and its cleavage products produced by reaction with native Asp f2. The FluHSA2 was cleaved at four sites near the C-terminus of the peptide. In bold are the cysteine residues (represented by C) that form a disulfide bond which results in circularization of the substrate.
Figure 9:
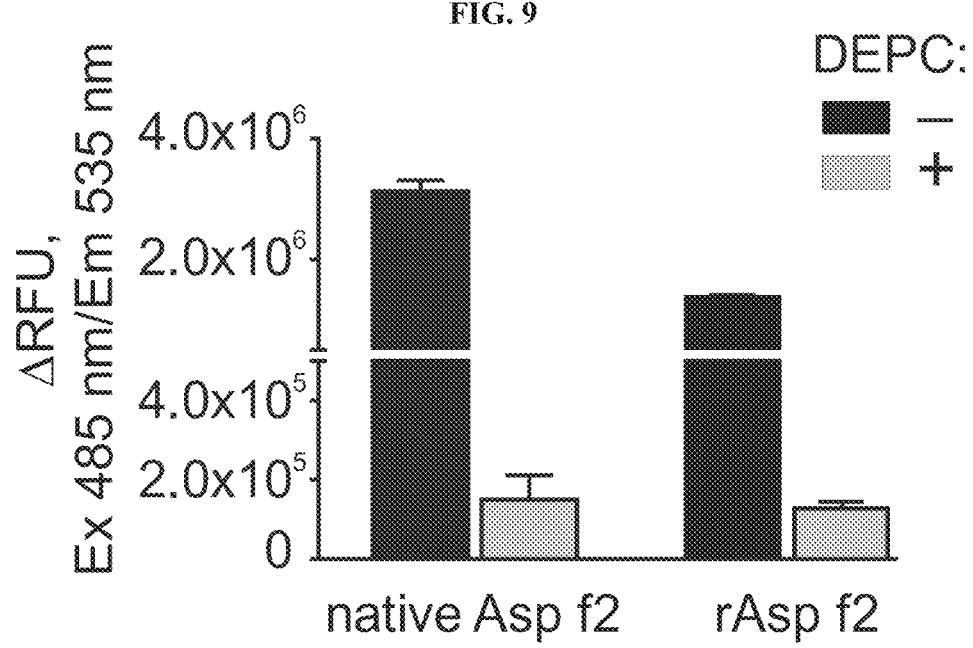
FIG. 9 shows the effect of diethylpyrocarbonate (DEPC) on proteolytic activity of native and recombinant forms of Asp f2. After one hour incubation with DEPC at 22° C., Asp f2 protease activity is inhibited. Treatment without DEPC is indicated by the black bar and treatment with DEPC is indicated by the grey bar.
Figure 10:
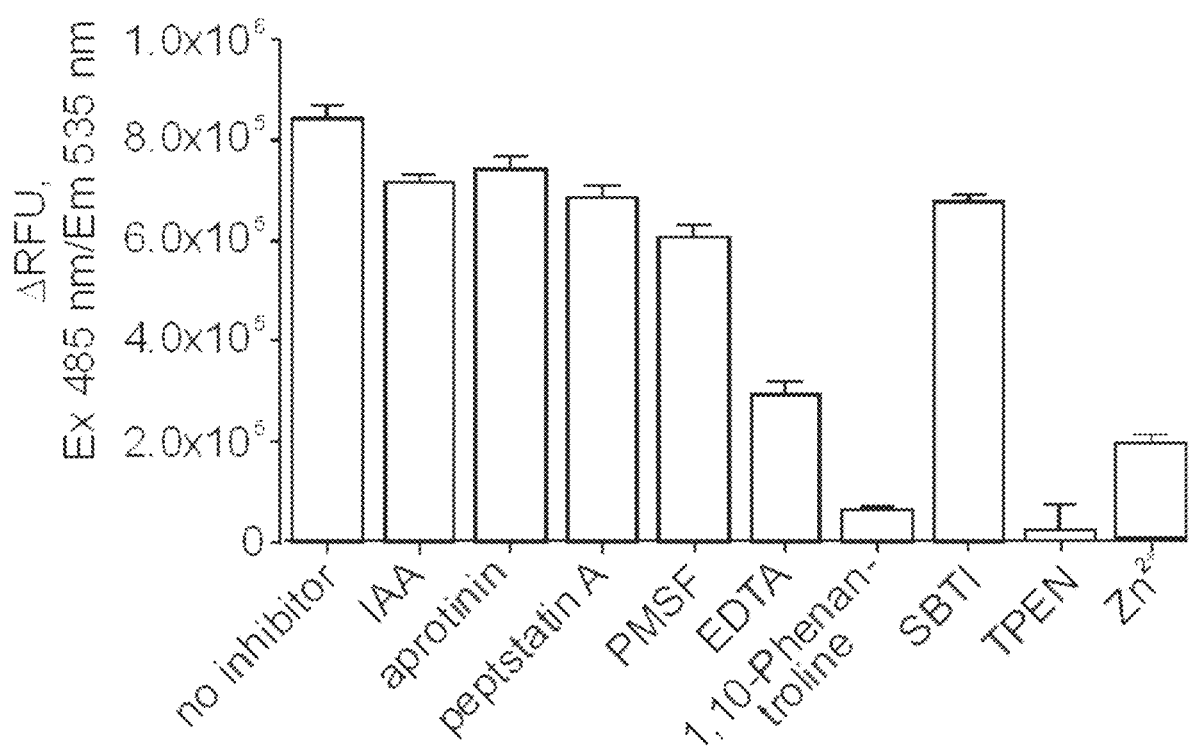
FIG. 10 shows the effects of various protease inhibitors and $Zn^{2+}$ ions on proteolytic activity of native Asp f2. Samples were treated as indicated with iodoacetamide (IAA), aprotinin, pepstatin A, phenylmethanesulfonylfluoride (PMSF), ethylenediaminetetraacetic acid, disodium salt (EDTA), 1-10-phenantroline, soybean trypsin inhibitor (SBTI), tetrakis-(2-pyridylmethyl) ethylenediamine (TPEN), or $Zn^{2+}$.
Figure 11:
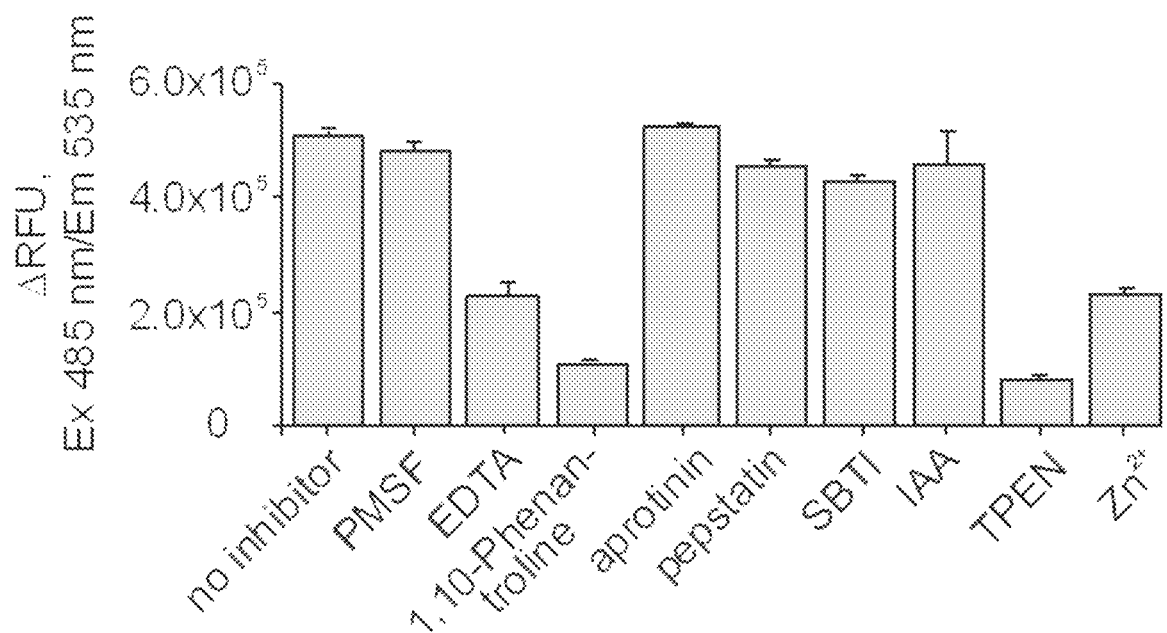
FIG. 11 shows the effects of various inhibitors and $Zn^{2+}$ ions on proteolytic activity of recombinant Asp f2. Samples were treated as indicated with phenylmethanesulfonylfluoride (PMSF), ethylenediaminetetraacetic acid, disodium salt (EDTA), 1-10-phenantroline, aprotinin, pepstatin A, soybean trypsin inhibitor (SBTI), iodoacetamide (IAA), tetrakis-(2-pyridylmethyl) ethylenediamine (TPEN), or $Zn^{2+}$.
Figure 13:
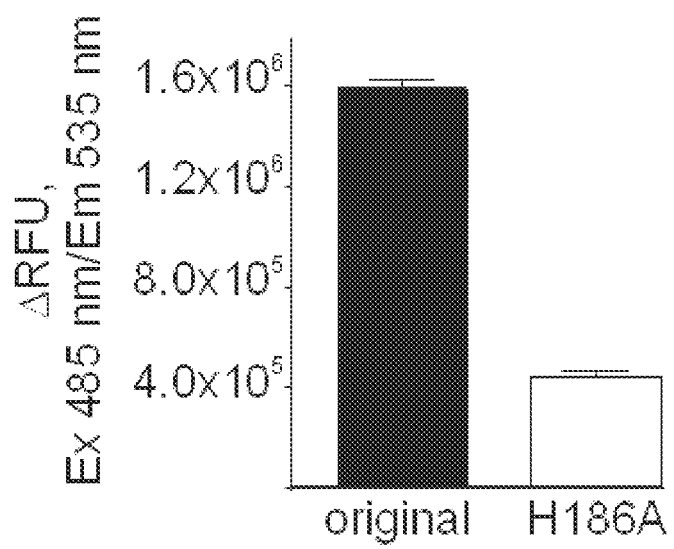
FIG. 13 shows that the H186A Asp f2 mutant (white bar) displays significantly lower proteolytic activity with FluHSA2 compared to the original wild type Asp f2 construct (black bar).
Figure 14:
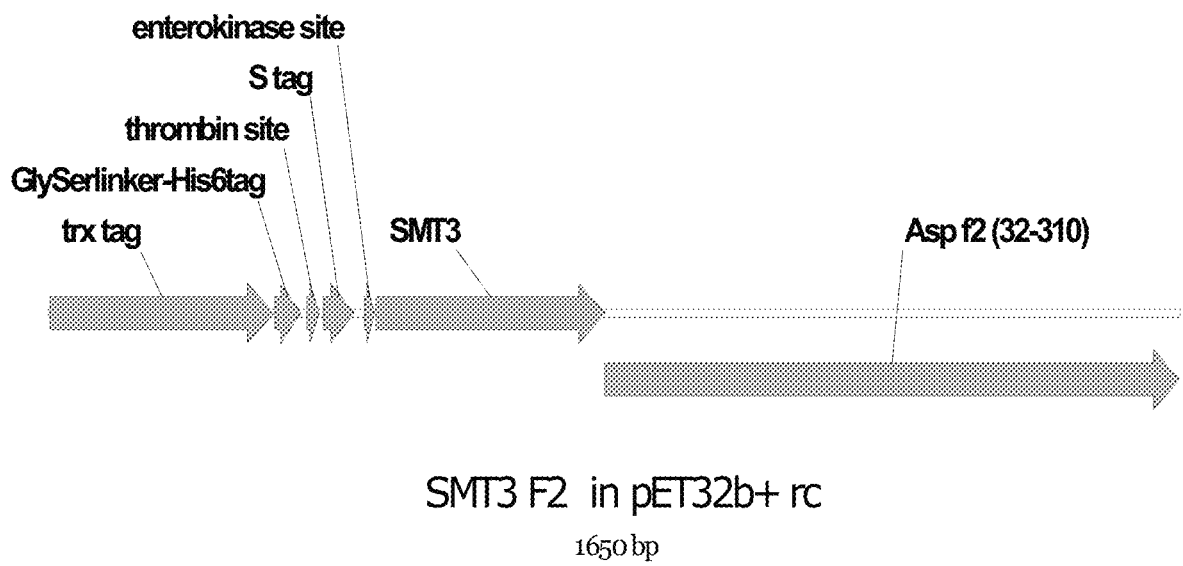
FIG. 14 shows the fusion protein construct for Trx-SMT3-Asp f2 [aa 32-310] (where aa is amino acids). The Trx-SMT3 N-terminal linker contained the following from N- to C-terminus: Thioredoxin (Trx)-(glycine-serine-linker-His$_6$)-(thrombin site)-(S-tag)-(enterokinase site)-(SMT3) and Asp f2 [aa 32-310]. Thioredoxin (Trx) was added to improve solubility of the construct and a yeast SUMO (Smt3) was added to help enhance expression and promote solubility of Asp f2.
Figure 17:
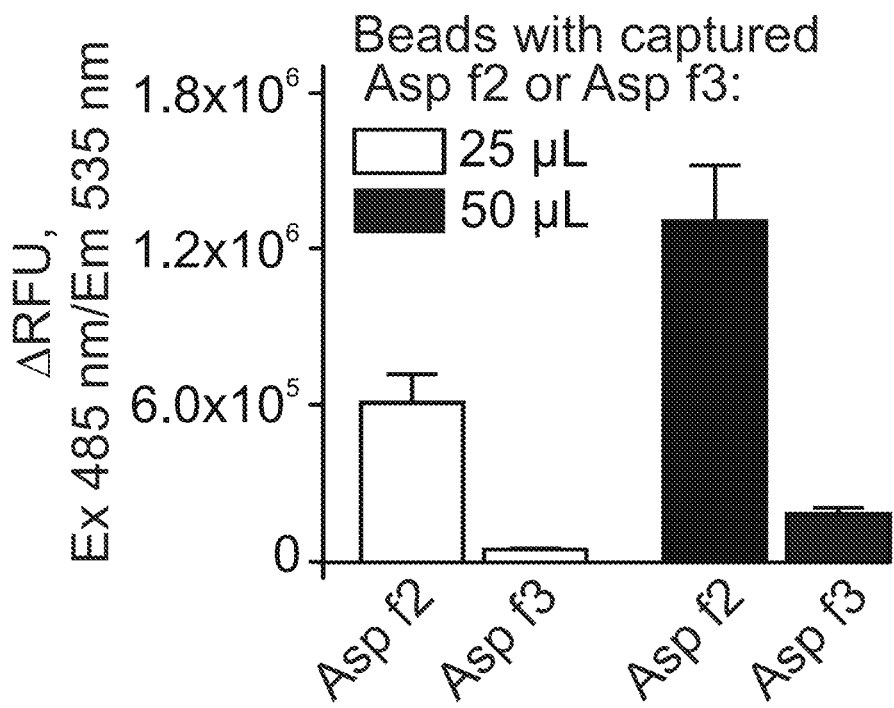
FIG. 17 illustrates the proteolytic activity of native Asp f2 and native Asp f3. Native Asp f2 and native Asp f3 were both tested with 25 µl (white bars) and 50 µl (black bars).
Figure 18:
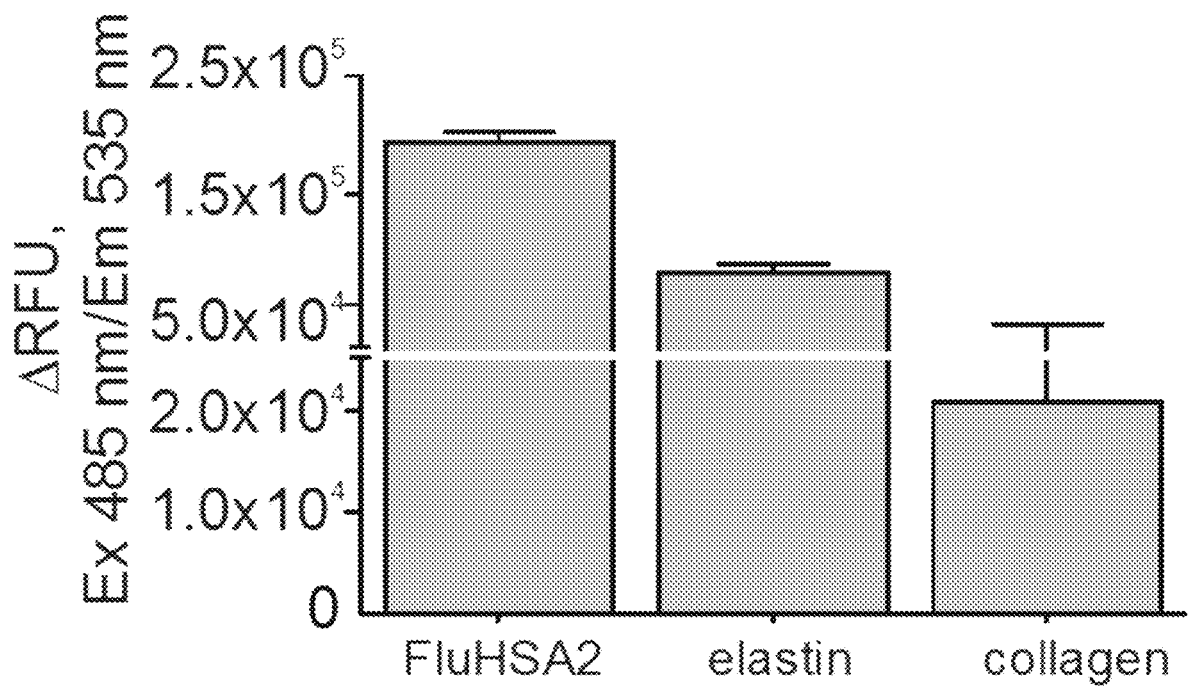
FIG. 18 illustrates the proteolytic activity of Asp f2 with different substrates including fluorogenic versions of elastin and collagen.

The enzymatic activity of immobilized Asp f2 was determined by cleavage of a novel fluorogenic peptide, FluHSA2 (FIGS. 4-5; [5-Fam]-TKCATESAVNRRPCFSALK-[DABCYL] SEQ ID NO: 5). FluHSA2 comprises the peptide of SEQ ID NO:5 conjugated to 5-Fam at the alpha-amino group of the threonine at the N-terminus of the peptide and to DABCYL at the epsilon amino group of the lysine side chain at the C-terminus of the peptide. Upon excitation, the DABCYL suppresses the fluorescence emission of the 5-Fam labeled peptides when the peptides are not cleaved and the fluorescent label and DABCYL remain close together. However, when the peptide is cleaved by Asp f2, the fluorescent label and DABCYL are separated and the fluorescent label emits light energy upon excitation. For each replicate (including negative controls), 100 µL of the antibody coupled bead suspension was transferred into 0.5 mL reaction buffer (FluHSA2 (FIG. 4-5; SEQ ID NO: 5), 10 in sodium phosphate, 25 mM, NaCl, 100 mM, pH 7.2. Tubes were incubated in the dark for two hours at 37° C. or for 16 hours at 22° C. on a rotary shaker at 250 rpm. Fluorescence was measured at Excitation (Ex) 485 nm/Emission (Em) 535 nm in a black 96-well micro titer plate.

Results indicated that the FluHSA2 peptide was cleaved in samples from patients suspected of having aspergillosis, but remained uncleaved in samples from patients that had other mold infections or no infection (FIG. 6; $p<0.0001$). Thus, the novel antibody 5D7A1 is highly specific for the detection of aspergillosis. As such, this assay provides a useful tool for the clinical diagnosis of aspergillosis.

Example 2: Characterization of Zinc Metalloprotease Activity of Asp f2

Previous studies have not detected Asp f2 proteolytic activity, and Asp f2 has not previously been classified as a metalloprotease because it has very low (~15%) sequence identity to the metalloproteases of the Zincin-like family and lacks the HEXXH (SEQ ID NO: 37) signature that characterizes all metalloproteases (Amich et al., 2010). However, a sequence alignment of Asp f2 with deuterolysin from *Aspergillus oryzae* and the putative metalloprotease MEP20 from *Aspergillus fumigatus* shows that Asp f2 contains a motif similar to the HEXXH (SEQ ID NO: 37) motif, [186]HRLYH (SEQ ID NO: 36) (FIGS. 7 and 8, respectively). To investigate whether Asp f2 is a zinc metalloprotease, the bead-based assay described in Example 1 was used to evaluate Asp f2 protease activity in the presence of histidine modifiers and various chelators, as well as the activity of an Asp f2 with a mutation in the histidine residue of the HRLYH (SEQ ID NO: 36) motif. These experiments led to the unexpected finding that Asp f2 possesses zinc metalloproteolytic activity.

It was not possible to express proteolytically active Asp f2 directly in *Escherichia coli* bacteria because "active" Asp f2 lacks the signal peptide MAALLRLAVLLPLAAPL-VATLPTSPVPIAAR (SEQ ID NO:39, residues 1-31) and kills the bacteria. Accordingly, active recombinant Asp f2 was generated using a fusion protein that expresses inactive recombinant Asp f2, which can then be activated after purification (FIGS. 14-16; SEQ ID NOS: 6 and 7). The fusion protein comprised an N-terminal linker (Trx-SMT3 N-terminal linker) region fused to Asp f2 residues 32-310 (codon optimized for expression in *E. coli*; FIG. 14) via a Ubiquitin-like-specific protease 1 (ULP1) cleavage site located between SMT3 and Asp f2. The Trx-SMT3 N-terminal linker contained the following from N- to C-terminus: thioredoxin (Trx)-glycine-serine-linker-$His_6$-tag-linkers-another $His_6$-tag-SMT3. Trx was added to improve solubility of the construct and a yeast SUMO (Smt3) was added to help enhance expression and promote solubility of Asp f2. Following purification using a $His_6$-tag specific nickel-NTA column, Asp f2 was activated by cleaving the Trx-SMT3 N-terminal linker off using UPL1. This process yielded active recombinant Asp f2. The different cleavage sites in the linker region of the fusion protein construct can be used for cleavage by other enzymes (FIG. 14).

Diethylpyrocarbonate (DEPC) derivatization of histidines results in the chemical modification of histidines in proteins and is used to study the importance of histidyl residues in enzymes. Using the materials and methods described in Example 1, anti-Asp f2 (5D7A1)-bound beads were incubated with native or recombinant Asp f2 in the presence or absence of DEPC (30 μM) and incubated for one hour at 22° C. prior to reaction with FluHSA2. Samples were then incubated with 10 μM of FluHSA2 for 16 hours at 22° C. and fluorescence was measured as described above. Cleavage of FluHSA2 was detected in the presence or absence of DEPC to test the proteolytic activity of native and recombinant Asp f2. Results show that both native and recombinant Asp f2 cleave the FluHSA2 substrate, but are inactive in the presence of DEPC (FIG. 9). This result indicates that at least one histidine residue may be necessary for Asp f2 proteolytic activity, indicating that Asp f2 may be a metalloprotease.

To further investigate whether Asp f2 possesses zinc metalloprotease activity, a variety of protease inhibitors and zinc ions were tested to investigate their effects on native and recombinant Asp f2 activity (FIGS. 10 and 11, respectively). Anti-Asp f2 (5D7A1)-bound beads were incubated with native or recombinant Asp f2 in the presence or absence of 0.5 mM zinc chloride or 50 μM of various inhibitors. Samples were incubated with FluHSA2 and fluorescence was measured as described above. Treatment with the zinc chelator, N,N,N',N'-tetrakis (2-pyridylmethyl) ethylenediamine (TPEN), the inhibitor of metallopeptidases, 1-10-phenanthroline, and the metal ion chelator, ethylenediaminetetraacetic acid (EDTA), suppressed both native and recombinant Asp f2 metalloprotease activity (FIGS. 10 and 11, respectively). Other protease inhibitors that are known to inhibit different families of proteases (e.g. cysteine peptidases (IAA), trypsin proteases (aprotinin and SBTI), aspartyl proteases (pepstatin A), and serine proteases (PMSF)), did not inhibit native or recombinant Asp f2 (FIGS. 10 and 11, respectively). These results further demonstrate that Asp f2 possesses zinc metalloprotease activity. Various Asp f2 histidine residues, including those located in the $^{186}$HRLYH motif, were mutated to alanine (FIG. 12; H186A and H190A are located in the HRLYH motif), and mutant or wild-type Asp f2 was incubated with anti-Asp f2 (5D7A1)-bound beads as described above, followed by incubation with FluHSA2. Mutation of histidine 186 to alanine significantly decreased the proteolytic activity of Asp f2 compared with wild-type Asp f2 (FIG. 13).

Example 3: Characterization of Asp 2 Substrates

Cleavage specificity of the novel FluHSA peptide was tested using Asp f2 and another *Aspergillus* protein, Asp f3. CNBr-activated sepharose beads were prepared as described in Example 1 and incubated with either the anti-Asp f2 monoclonal antibody 5D7A1 or an anti-Asp f3 rabbit polyclonal antibody. Anti-Asp f2-immobilized beads were incubated with native Asp f2 and anti-Asp f3-immobilized beads were incubated with native Asp f3. Samples were incubated with FluHSA2 (10 μM) for 16 hours at 22° C. Fluorescence was measured at Ex 485 nm/Em 535 nm in a black 96-well micro titer plate as described above. FluHSA2 was found to exhibit high specificity for cleavage by Asp f2 compared with Asp f3 (FIG. 17). This demonstrates the remarkable specificity that the FluHSA2 peptide has for the *Aspergillus* glycoprotein Asp f2.

The cleavage products of FluHSA2 after reaction with native Asp f2 were investigated by mass spectrometric analysis (MALDI spectra) (FIG. 5). Cleavage by Asp f2 occurred in the C-terminal linear tail section of the peptide resulting in at least 5 cleavage products (FIG. 5).

Peptides other than FluHSA2 were tested for cleavage by Asp f2. Anti-Asp f2 (5D7A1)-bound beads were incubated with native Asp f2, then incubated with either FluHSA2 (10 fluorescent labeled elastin protein (5-Fam-QXL520 labeled-elastin; SensoLyteGreen Elastase assay kit, #72178, Anaspec, Freemont, Calif., USA) or FITC conjugated collagen (#85111, Anaspec, Freemont, Calif., USA) (15 μg/mL). Fluorescence was measured at Ex 485 nm/Em 535 nm in a black 96-well micro titer plate as described above. Results showed that native Asp f2 is also capable of degrading the human proteins collagen and elastin (FIG. 18). This demonstrates that active Asp f2 enriched on beads with 5D7A1 can cleave both fluorogenic elastin and collagen.

Example 4: Characterization of Asp f2 and Anti-Asp f2 Antibody Binding

The specificity of binding between Asp f2 and the anti-Asp f2 antibody 5D7A1 was further investigated using 5D7A1 and a variety of other antibodies known to bind *Aspergillus* Asp proteins other than Asp f2 (anti-Asp f1 (specific for Asp f1) and anti-Asp f3 (specific for Asp f3)) and proteases (4E17.1 (specific for botulinum neurotoxin serotype A heavy chain)) in the bead-based protease activity assay as described above. Polyclonal Rabbit IgG antibody was used as a non-specific IgG control. Antibodies were incubated with culture filtrate from *A. fumigatus*, and protease activity was detected using the 5-FAM-labeled elastin protein or FITC-conjugated collagen protein described above in Example 3. Fluorescence was measured at Ex 485 nm/Em 535 nm in a black 96-well micro titer plate as described above.

Figure 19:
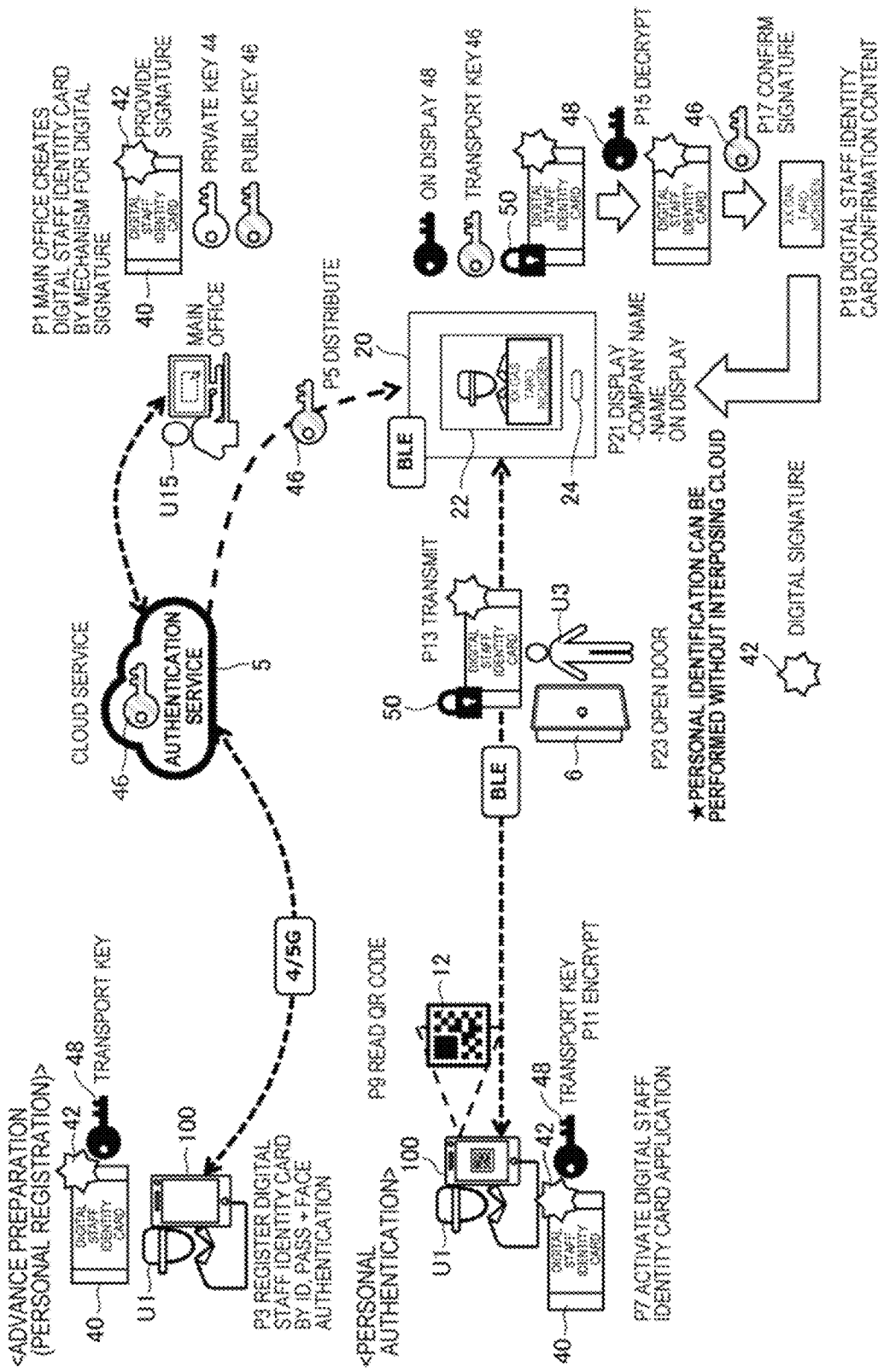
FIG. 19 shows a bead-based assay using different antibodies as indicated to assess Asp f2 proteolytic cleavage of the FITC-collagen substrate. Asp f2 showed the most robust proteolytic activity with the anti-Asp f2 antibody, 5D7A1, compared with other antibodies that are non-Asp f2 specific antibodies (4E17.1, anti-Asp f1, anti-Asp f3, and rabbit IgG).
Figure 20:
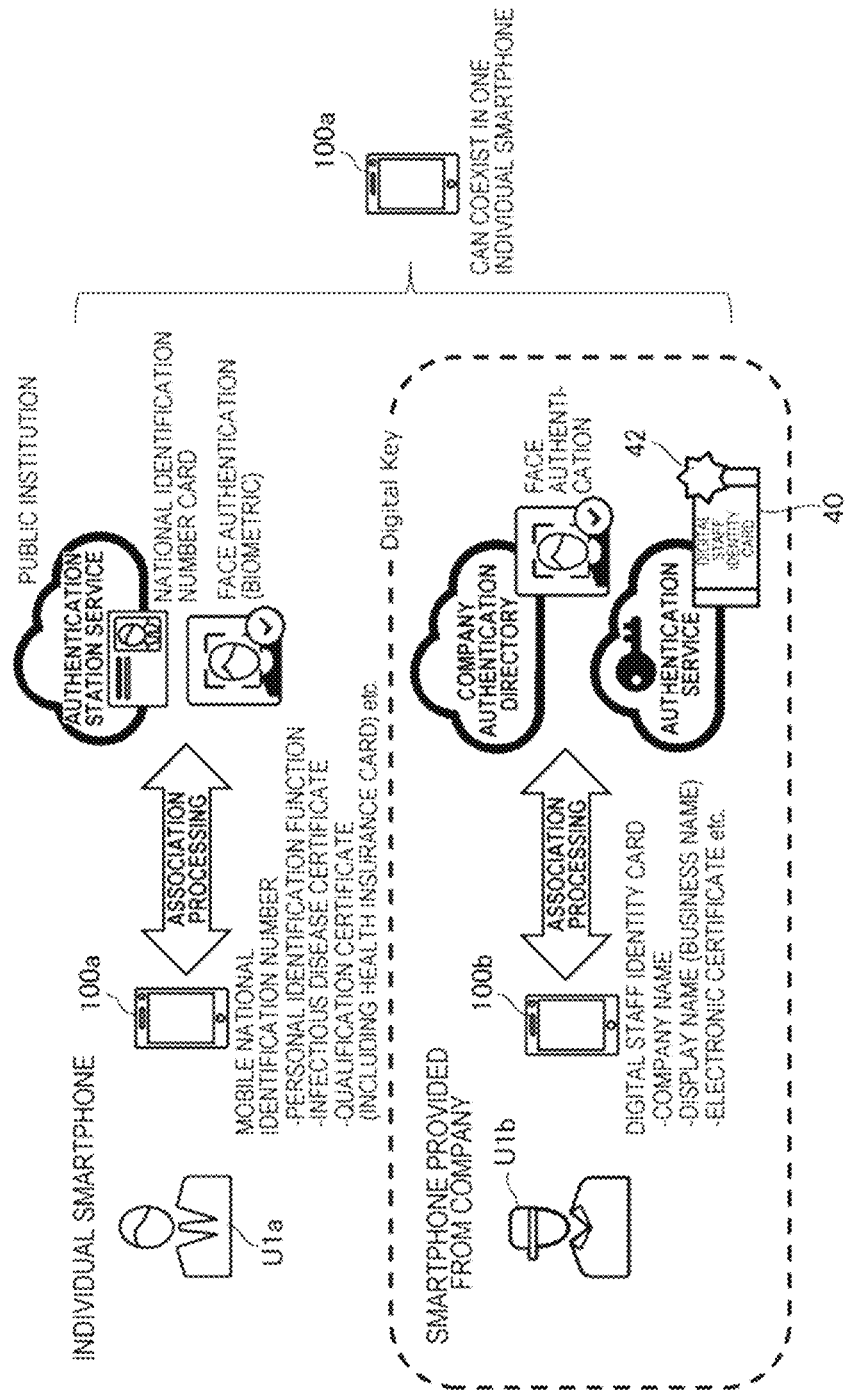
FIG. 20 shows a bead-based assay using different antibodies as indicated to assess Asp f2 proteolytic cleavage of the 5-Fam-elastin substrate. Asp f2 showed the most robust proteolytic activity with the anti-Asp f2 antibody, 5D7A1 compared with other antibodies that are non-Asp f2 specific antibodies (4E17.1, anti-Asp f1, anti-Asp f3, and rabbit IgG).

Results demonstrated that robust Asp f2 cleavage of the collagen and elastin substrates was detected in only those samples containing the anti-Asp f2 antibody 5D7A1 (FIG. 19, FITC-collagen substrate; FIG. 20, 5-Fam elastin substrate). Little to no activity was observed in samples containing antibodies that are non-Asp f2 specific antibodies (FIGS. 19 and 20). This assay demonstrates that Asp f2 and 5D7A1 bind each other specifically.

Example 5: Asp f2 Proteolytic Activity in Aspergillosis Patients

Figure 21:
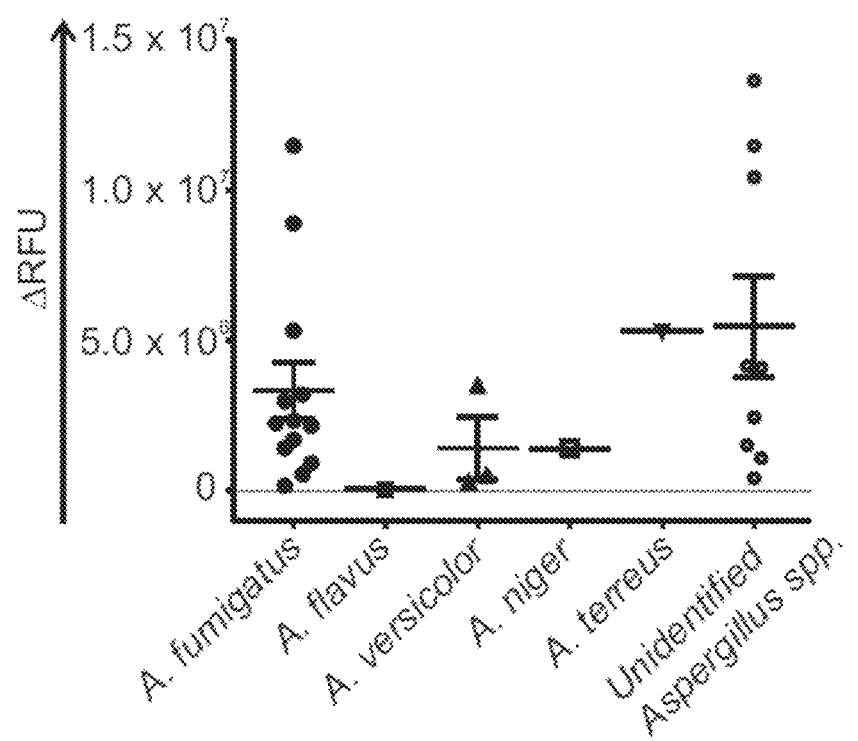
FIG. 21 shows Asp f2 proteolytic activity in aspergillosis patients for which *Aspergillus* species were identified as indicated by the clinical Microbiology lab at City of Hope. ●=*A. fumigatus*, ■=*A. flavus*, ▲=*A. versicolor*, □=*A. niger*, ▼=*A. terreus*, ○=unidentified *Aspergillus* species.

Most aspergillosis is caused by *A. fumigatus*, but there are other aspergilli that can cause the disease. Proteolytic activity of Asp f2 was investigated in BALF samples from aspergillosis patients for which *Aspergillus* species were identified as indicated by the clinical Microbiology lab at City of Hope. The different species identified were *A. fumigatus, A. flavus, A. versicolor, A. niger, A. terreus*, and other unidentified *Aspergillus* species. Results demonstrate that Asp f2 proteolytic activity may be useful for detecting other *Aspergillus* species as well (FIG. 21).

Example 6: Sensitivity, Specificity, and Cut-Off Values of Asp f2 Assay

Figure 25:
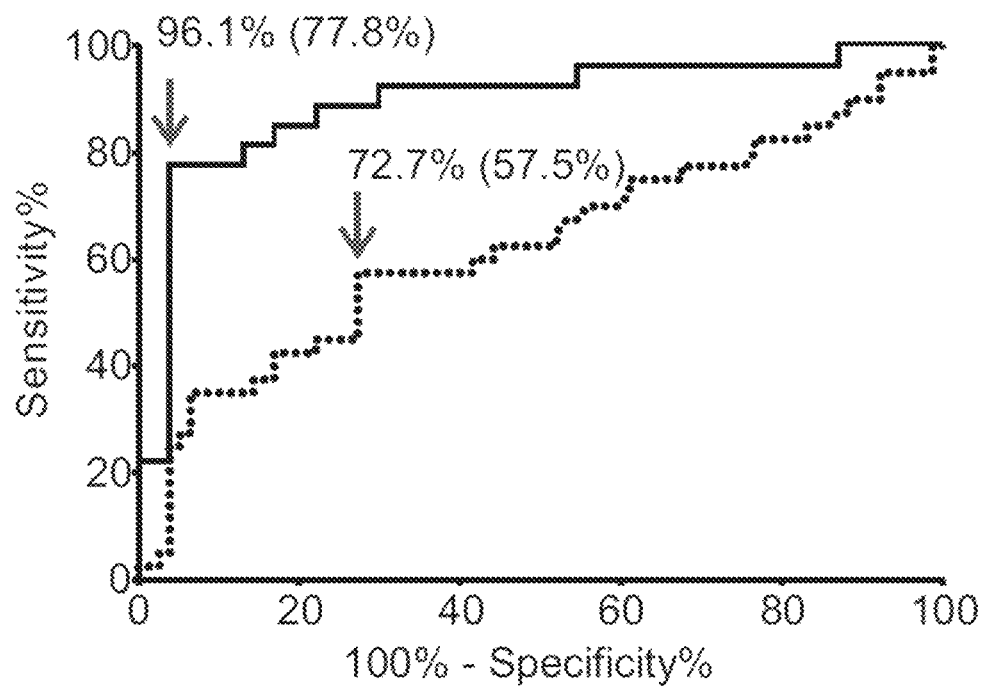
FIG. 25 shows a ROC curve illustrating the sensitivity, specificity, and appropriate cut-off values for the presently disclosed Asp f2 activity assay. Solid line=aspergillosis, dotted line=all other mold infections.

A receiver operating characteristic (ROC) curve was generated to determine the sensitivity, specificity, and appropriate cut off values of the bead-based Asp f2 assay described herein (FIG. 25). The ROC analysis included clinical diagnostic data from a total of 144 patients, of which 27 had aspergillosis, 40 had other mold infections, and 77 were diagnosed negative for fungal infections. The ROC curve was used to determine the cutoff value for positive Asp f2 activity assay values. This cutoff value is $\Delta RFU=8.8\times10^5$, which corresponds to approximately 280 pmol/mL substrate (HSA2 peptide) cleaved by Asp f2 in 16 hours. The assay was found to have a specificity of 96.1% at a sensitivity of 77.8% for cases of aspergillosis versus a specificity of 72.7% at 57.5% sensitivity for all other mold infections, indicating that the assay is highly specific and sensitive for aspergillosis, and less specific and sensitive for other mold infections.

Figure 26A:
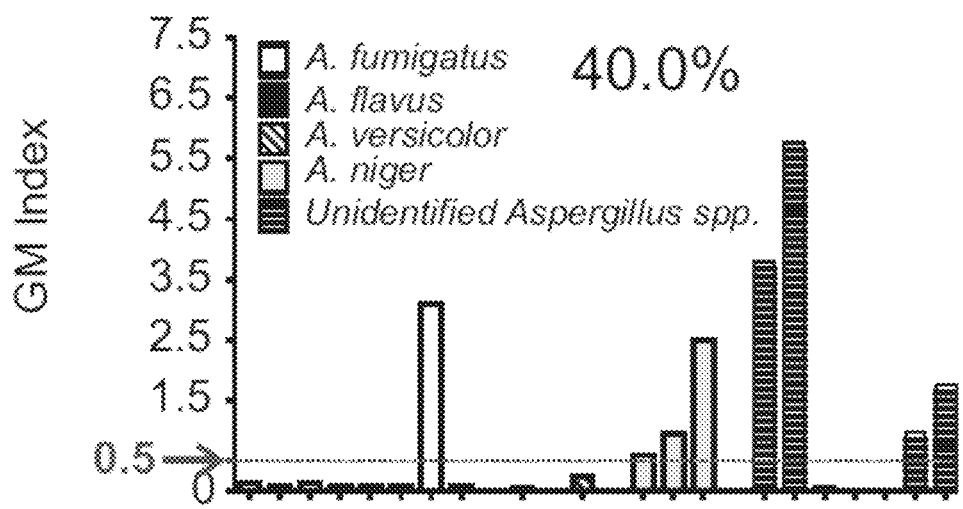
FIG. 26A shows clinical galactomannan (GM) test results for diagnosis of aspergillosis infection.
Figure 26B:
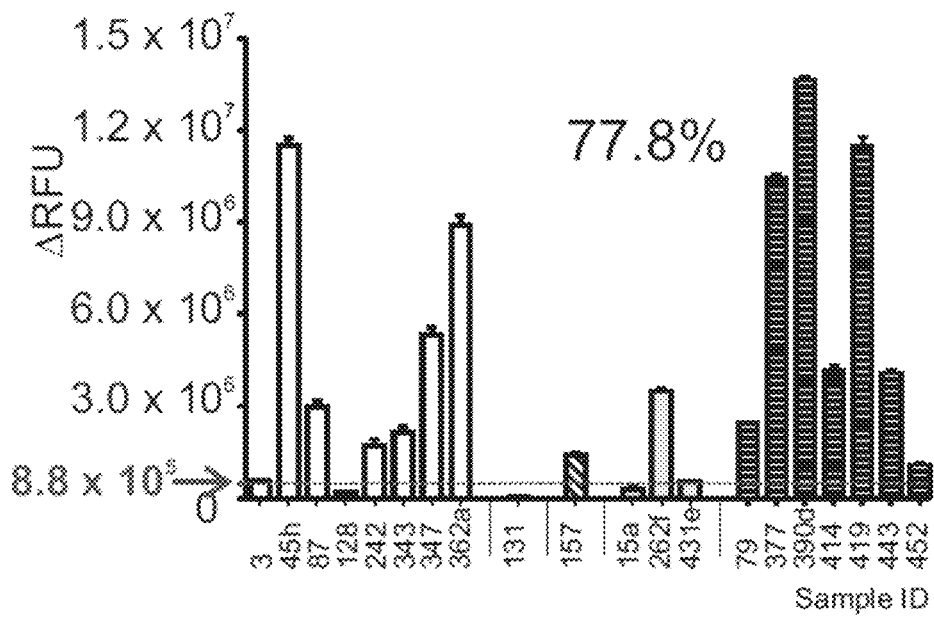
FIG. 26B shows the presently disclosed Asp f2 activity assay for diagnosis of aspergillosis infection.

Example 7: Comparison of Asp f2 Activity Assay and Clinical Galactomannan (GM) Test Results The Asp f2 activity assay disclosed herein was compared to clinical galactomannan (GM) test results. Clinical diagnosis was based on the EORTC/MSG criteria for probable and proven aspergillosis (DePauw 2008), including cytological, pathological, and microbiological examination of the patients by infectious disease physicians. The GM assay was performed by a clinical laboratory. A GM index cut off of >0.5 for patients positive with fungal infections was used in accordance with clinical practice. The GM assay had only 40% sensitivity in the sample group of City of Hope aspergillosis patients (FIG. 26A), while the Asp f2 activity assay achieved 77.8% sensitivity in the same group of patients (FIG. 26B). A cut-off value of $>\Delta RFU=8.8\times10^5$ (equivalent to 280 pmol/mL converted substrate in 16 hours) was used to determine aspergillosis positive samples.

Example 8: Generation of Recombinant Antibodies Based on 5D7A1 Variable Chain Sequences A molecular cloning approach was used to generate single-chain variable fragments (scFvs) from the sequenced $V_L$ and $V_H$ chains of 5D7A1. Two types of scFvs were generated. In the first, the C-terminus of the $V_L$ chain is linked to the N-terminus of the $V_H$ chain via a glycine-serine linker (GS15). In the second, the sequential order of the V chains is reversed such that the C-terminus of the $V_H$ chain is linked to the N-terminus of the $V_L$ chain using the same GS15 linker.

Figure 27:
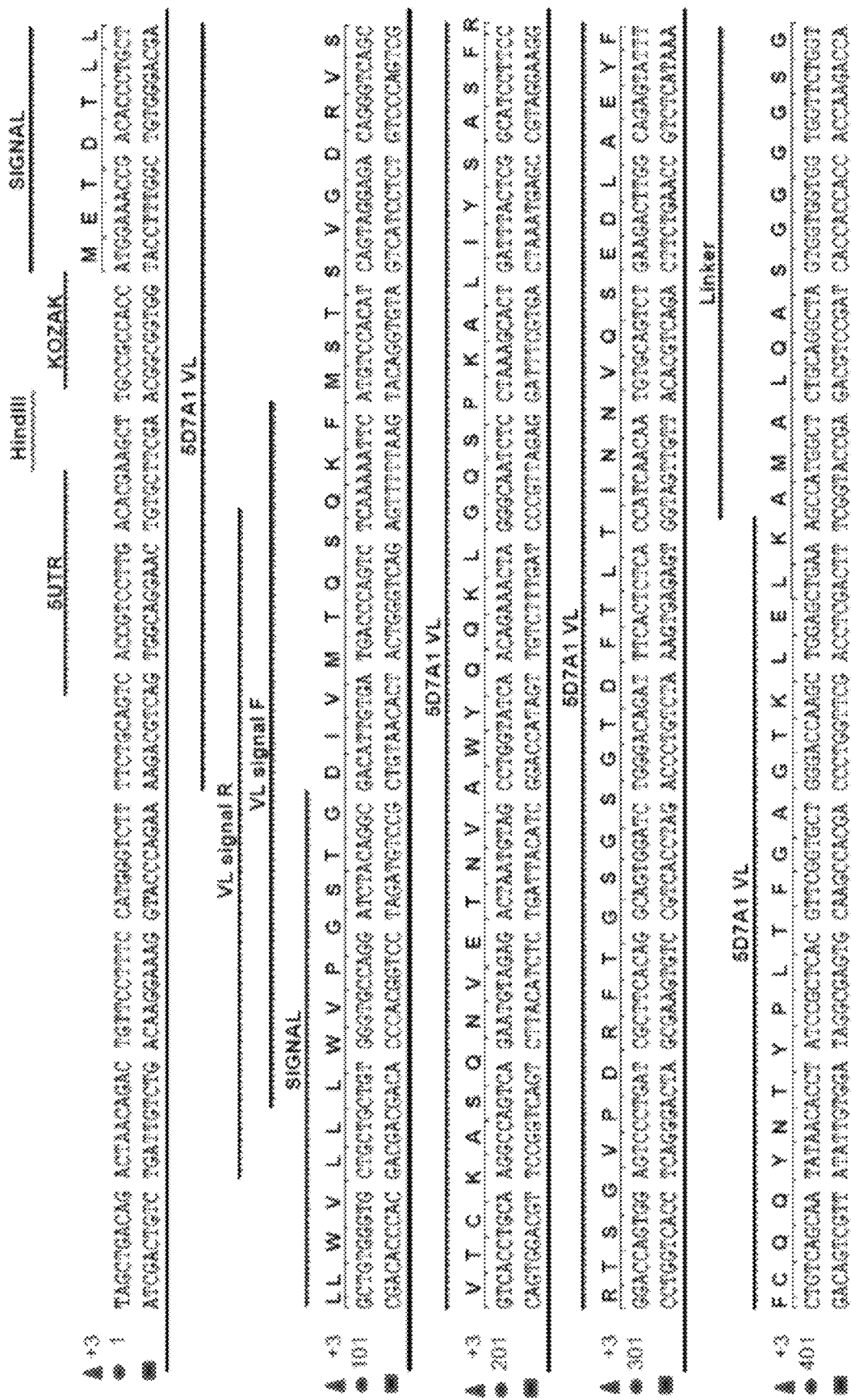
FIG. 27 shows the amino acid sequence of VL-GS15-VH-Fc scFv and the DNA sequence of the VL-GS15-VH-Fc scFv in the pEE12.4 vector. The amino acid sequence of VL-GS15-VH-Fc scFv is marked with triangles (SEQ ID NO: 20). The 5'-3' DNA sequence of the VL-GS15-VH-Fc scFv and surrounding pEE12.4 vector region is marked with circles (SEQ ID NO: 32) and the 3'-5' complementary strand is marked with squares (SEQ ID NO: 33). Note that although the figure shows the 3'-5' complementary DNA strand (see squares), SEQ ID NO: 33 in the sequence listing represents the reverse (i.e., 5'-3') complement of SEQ ID NO: 32.
Figure 29:
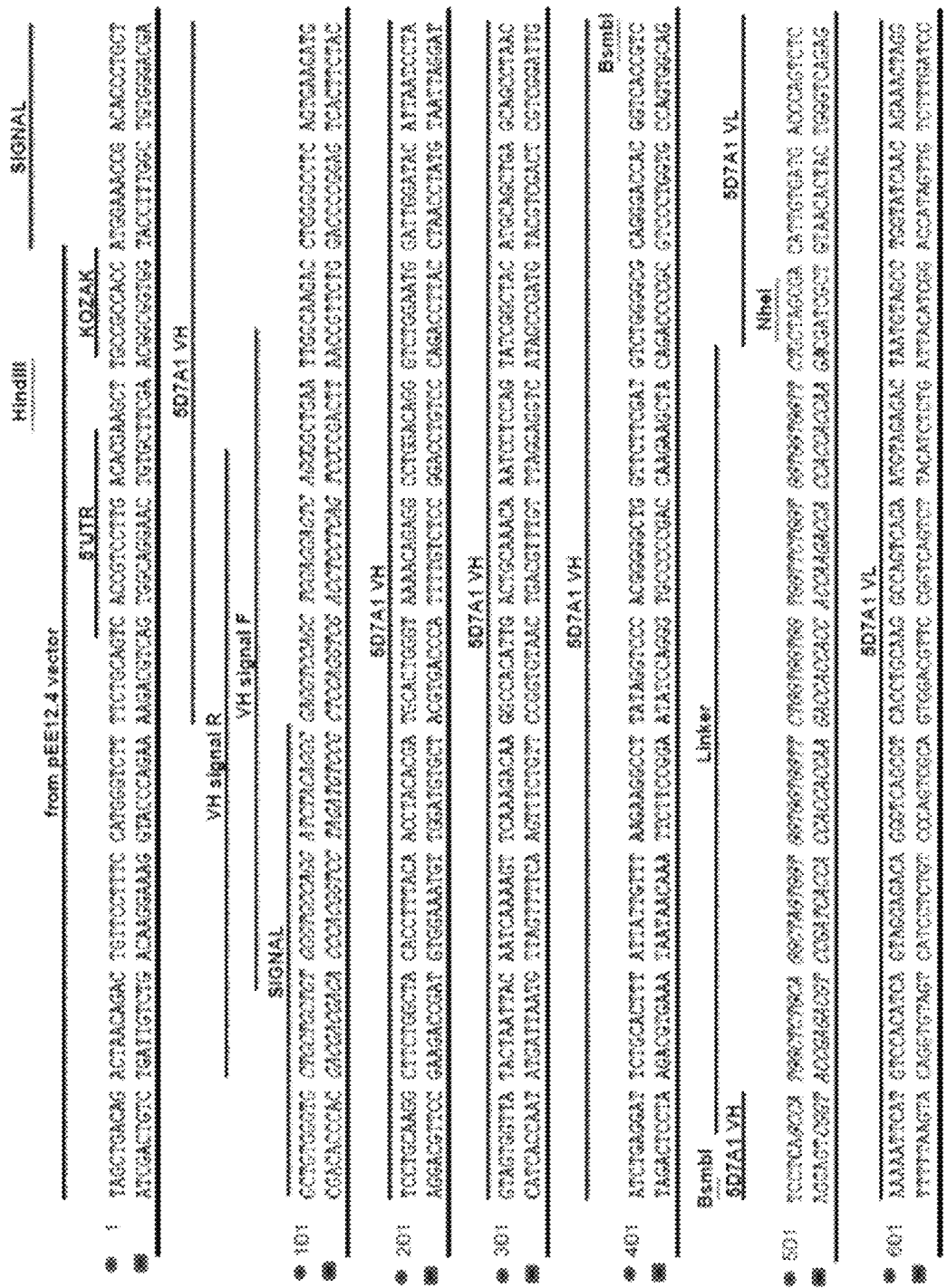
FIG. 29 shows the DNA sequence of the VH-GS15-VL-Fc scFv in the pEE12.4 vector. The 5'-3' DNA sequence of the VH-GS15-VL-Fc scFv and surrounding pEE12.4 vector region is marked with circles (SEQ ID NO: 34) and the 3'-5' complementary strand is marked with squares (SEQ ID NO: 35). Note that although the figure shows the 3'-5' complementary DNA strand (see squares), SEQ ID NO: 35 in the sequence listing represents the reverse (i.e., 5'-3') complement of SEQ ID NO: 34.
Figure 29:
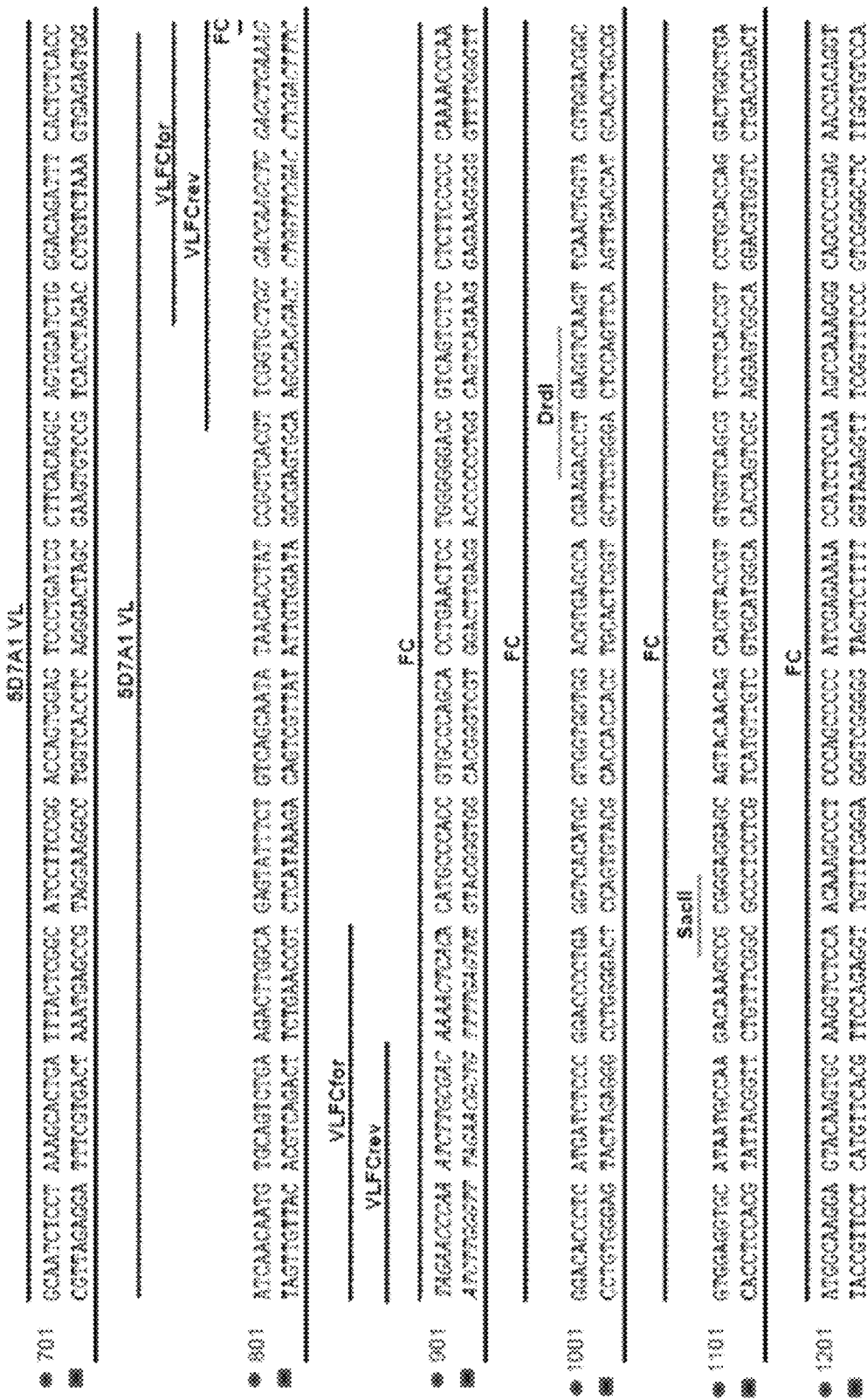

Initial attempts at scFv expression resulted in insoluble products. To overcome this, scFvs were fused to a human Fc domain of IgG, and a human antibody signal peptide was added. The resultant DNA construct was cloned into a pEE12.4 vector (GS Gene Expression System; see WO06/111387) and expressed in Expi293F cells (derived from 293 cells, primary embryonic human kidney; Gibco, Life technologies) in Expi293 expression medium (Gibco, Life technologies). The resulting single chain monovalent antibody homologues were soluble and exhibited Asp f2 specific binding affinities. The DNA and amino acid sequences of the $V_L$-GS15-$V_H$-Fc scFv are set forth in FIGS. 27-28 and SEQ ID NOs: 20-21, and the sequences of the $V_H$-G-515-$V_L$-Fc scFv are set forth in FIGS. 29-30 and SEQ ID NOs: 22-23.

Example 9: Immunoaffinity Analysis of Recombinant scFvs

Figure 31A:
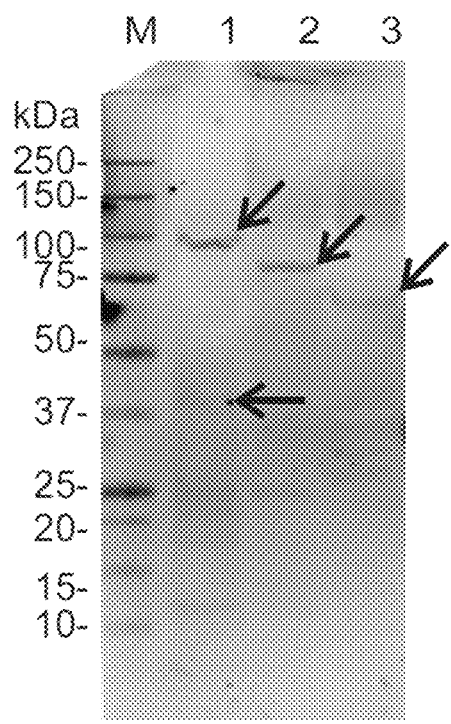
FIG. 31A shows a Western blots for $V_H$-GS15-$V_L$-FC scFv binding to Asp f2. Asp f2-specific bands are marked by asterisks (*) as indicated by the arrows as shown. The following protein samples were loaded. M: molecular weight marker; 1: *A. fumigatus* culture filtrate of a 9-day culture; 2: *A. fumigatus* culture filtrate of another, shorter culture; 3: recombinant (r)SMT3-Asp f2. The strong band at ~40 kDa represents unglycosylated Asp f2 that yields a stronger signal with 5D7A1 than with $V_H$-GS15-$V_L$-FC scFv.
Figure 31B:
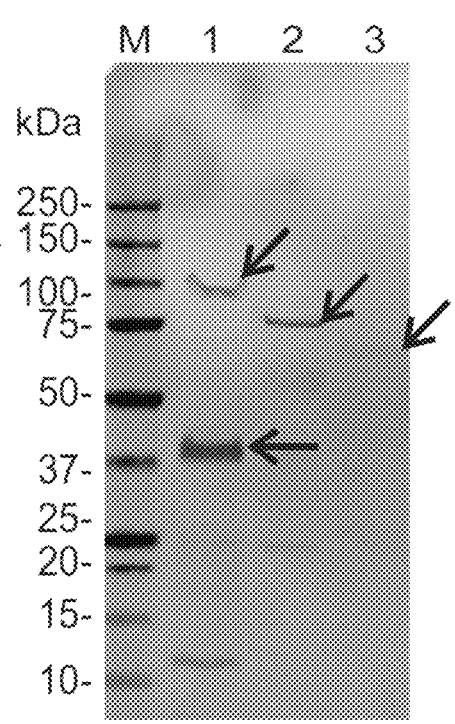
FIG. 31B shows a Western blot for 5D7A1 binding to Asp f2. Asp f2-specific bands are marked by asterisks (*) as indicated by the arrows as shown. The following protein samples were loaded. M: molecular weight marker; 1: *A. fumigatus* culture filtrate of a 9-day culture; 2: *A. fumigatus* culture filtrate of another, shorter culture; 3: recombinant (r)SMT3-Asp f2. The strong band at ~40 kDa represents unglycosylated Asp f2 that yields a stronger signal with 5D7A1 than with $V_H$-GS15-$V_L$-FC scFv.

Western blots were performed to compare the binding specificity of 5D7A1 and the recombinant scFvs generated in Example 8. 5D7A1 and $V_H$-G-515-$V_L$-Fc scFv both bound native Asp f2 independent of the different glycosylation states responsible for the different gel migration patterns in lanes 1 and 2, and weakly bound recombinant SMT3-Asp f2 (FIG. 31). Unglycosylated Asp f2 showed a stronger signal for 5D7A1 than for the scFv.

As stated above, the foregoing are merely intended to illustrate the various embodiments of the present invention. As such, the specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Amich Eukaryot Cell 9:424-437 (2010)
2. DePauw Clin Infect Dis 46:1813-1821 (2008)

What is claimed is:

1. A method for detecting *Aspergillus* Asp f2 in a biological sample comprising contacting the sample with an Asp f2 protease substrate that can be cleaved by Asp f2, wherein cleavage of the protease substrate indicates the presence of Asp f2 in the sample; and wherein the protease substrate comprises the amino acid sequence of SEQ ID NO:38.

2. The method of claim 1, wherein the sample is enriched for Asp f2 prior to contact with the Asp f2 protease substrate by contacting the sample with an Asp f2-specific antibody or antigen binding fragment comprising an amino acid sequence selected from the group consisting of SEQ ID NOs: 1, 2, 8, 10, 12, 14, 16, 18, 20, and 22.

3. The method of claim 2, wherein the Asp f2-specific antibody is immobilized on an enrichment matrix.

4. The method of claim 1, wherein the protease substrate is conjugated to one or more fluorophores.

5. A method for diagnosing aspergillosis in a subject comprising:
(a) obtaining a biological sample from the subject;
(b) detecting the presence of *Aspergillus* Asp f2 in the sample by contacting the sample with an Asp f2 protease substrate that can be cleaved by Asp f2, wherein cleavage of the protease substrate indicates the presence of Asp f2 in the sample; and
(c) diagnosing the subject with aspergillosis if Asp f2 is present in the sample,
wherein the protease substrate comprises the amino acid sequence of SEQ ID NO:38, and wherein the protease substrate is conjugated to one or more fluorophores.

6. The method of claim 5, further comprising (d) administering one or more therapeutic agents for the treatment of aspergillosis.

7. The method of claim 6, wherein the sample is enriched for Asp f2 prior to contact with the Asp f2 protease substrate by contacting the sample with an Asp f2-specific antibody or antigen binding fragment comprising an amino acid sequence selected from the group consisting of SEQ ID NOs: 1, 2, 8, 10, 12, 14, 16, 18, 20, and 22.

8. The method of claim 7, wherein the Asp f2-specific antibody is immobilized on an enrichment matrix.

9. The method of claim 5, wherein the aspergillosis is the result of infection with an *Aspergillus* species selected from the group consisting of *A. fumigatus, A. flavus, A. versicolor, A. niger*, and *A. terreus*.

10. A method for the treatment of aspergillosis in a subject in need thereof comprising:
(a) obtaining a biological sample from the subject;
(b) detecting the presence of *Aspergillus* Asp f2 in the sample by contacting the sample with an Asp f2 protease substrate that can be cleaved by Asp f2, wherein cleavage of the protease substrate indicates the presence of Asp f2 in the sample; and
(c) administering one or more therapeutic agents for the treatment of aspergillosis if Asp f2 is detected in the sample, and
wherein the protease substrate comprises the amino acid sequence of SEQ ID NO:38.

11. The method of claim 10, wherein the sample is enriched for Asp f2 prior to contact with the Asp f2 protease substrate by contacting the sample with an Asp f2-specific antibody or antigen binding fragment comprising an amino acid sequence selected from the group consisting of SEQ ID NOs: 1, 2, 8, 10, 12, 14, 16, 18, 20, and 22.

12. The method of claim 11, wherein the Asp f2-specific antibody is immobilized on an enrichment matrix.

13. The method of claim 10, wherein the protease substrate is conjugated to one or more fluorophores.

14. The method of claim 10, wherein the aspergillosis is the result of infection with an *Aspergillus* species selected from the group consisting of *A. fumigatus, A. flavus, A. versicolor, A. niger*, and *A. terreus*.

* * * * *